(12) United States Patent
Gnerre et al.

(10) Patent No.: US 11,866,777 B2
(45) Date of Patent: *Jan. 9, 2024

(54) ERROR SUPPRESSION IN SEQUENCED DNA FRAGMENTS USING REDUNDANT READS WITH UNIQUE MOLECULAR INDICES (UMIS)

(71) Applicant: Illumina, Inc., San Diego, CA (US)

(72) Inventors: Sante Gnerre, Mountain View, CA (US); Byoungsok Jung, Atherton, CA (US); Emrah Kostem, Redwood City, CA (US); Alex Aravanis, San Mateo, CA (US); Alex So, San Diego, CA (US); Xuyu Cai, Natick, MA (US); Zhihong Zhang, San Diego, CA (US); Frank J. Steemers, Encinitas, CA (US)

(73) Assignee: Illumina, Inc., San Diego, CA (US)

( * ) Notice: Subject to any disclaimer, the term of this patent is extended or adjusted under 35 U.S.C. 154(b) by 34 days.

This patent is subject to a terminal disclaimer.

(21) Appl. No.: 17/076,715

(22) Filed: Oct. 21, 2020

(65) Prior Publication Data

US 2021/0108262 A1  Apr. 15, 2021

Related U.S. Application Data

(63) Continuation of application No. 15/130,668, filed on Apr. 15, 2016, now Pat. No. 10,844,428.

(60) Provisional application No. 62/269,485, filed on Dec. 18, 2015, provisional application No. 62/193,469, filed on Jul. 16, 2015, provisional application No. 62/153,699, filed on Apr. 28, 2015.

(51) Int. Cl.
| | | |
|---|---|---|
| C12Q 1/6869 | (2018.01) | |
| G16B 30/00 | (2019.01) | |
| C12N 15/10 | (2006.01) | |
| C12Q 1/6806 | (2018.01) | |
| G16B 30/10 | (2019.01) | |
| C12Q 1/6855 | (2018.01) | |

(52) U.S. Cl.
CPC ....... *C12Q 1/6869* (2013.01); *C12N 15/1065* (2013.01); *C12Q 1/6806* (2013.01); *C12Q 1/6855* (2013.01); *G16B 30/00* (2019.02); *G16B 30/10* (2019.02)

(58) Field of Classification Search
CPC ................. C12Q 1/6869; C12Q 1/6855; C12Q 2525/191; C12N 15/1065
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 6,159,736 A | 12/2000 | Reznikoff et al. |
| 7,057,026 B2 | 6/2006 | Barnes et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,405,281 B2 | 7/2008 | Xu et al. |
| 8,822,150 B2 | 9/2014 | Bignell et al. |
| 9,260,745 B2 | 2/2016 | Rava et al. |
| 9,752,188 B2 | 9/2017 | Schmitt et al. |
| 9,845,552 B2 | 12/2017 | Blume et al. |
| 10,287,631 B2 | 5/2019 | Salk et al. |
| 10,370,713 B2 | 8/2019 | Salk et al. |
| 10,385,393 B2 | 8/2019 | Salk et al. |
| 10,570,451 B2 | 2/2020 | Salk et al. |
| 10,604,804 B2 | 3/2020 | Salk et al. |
| 10,689,699 B2 | 6/2020 | Salk et al. |
| 10,689,700 B2 | 6/2020 | Salk et al. |
| 10,711,304 B2 | 7/2020 | Salk et al. |
| 10,752,951 B2 | 8/2020 | Salk et al. |
| 10,760,127 B2 | 9/2020 | Salk et al. |
| 10,844,428 B2 | 11/2020 | Gnerre et al. |
| 10,844,429 B2 | 11/2020 | Wu et al. |
| 11,047,006 B2 | 6/2021 | Salk et al. |
| 11,098,359 B2 | 8/2021 | Salk et al. |
| 11,118,225 B2 | 9/2021 | Salk et al. |
| 11,130,996 B2 | 9/2021 | Salk et al. |
| 11,155,869 B2 | 10/2021 | Salk et al. |
| 11,198,907 B2 | 12/2021 | Salk et al. |

(Continued)

FOREIGN PATENT DOCUMENTS

| | | |
|---|---|---|
| CN | 103154273 A | 6/2013 |
| EP | 3682032 A1 | 7/2020 |

(Continued)

OTHER PUBLICATIONS

US 11,629,382 B2, 04/2023, Salk et al. (withdrawn)
European Notice of Opposition dated Jan. 11, 2021 in EP Application No. 16720269.6.
Canadian First Office Action dated Feb. 2, 2021 in CN Application No. CA 3063750.

(Continued)

*Primary Examiner* — Sahana S Kaup
(74) *Attorney, Agent, or Firm* — Weaver Austin Villeneuve & Sampson LLP

(57) ABSTRACT

The disclosed embodiments concern methods, apparatus, systems and computer program products for determining sequences of interest using unique molecular index (UMI) sequences that are uniquely associable with individual polynucleotide fragments, including sequences with low allele frequencies and long sequence length. In some implementations, the UMIs include both physical UMIs and virtual UMIs. In some implementations, the unique molecular index sequences include non-random sequences. System, apparatus, and computer program products are also provided for determining a sequence of interest implementing the methods disclosed.

14 Claims, 25 Drawing Sheets

Specification includes a Sequence Listing.

(56) References Cited

U.S. PATENT DOCUMENTS

| | | | |
|---|---|---|---|
| 11,242,562 | B2 | 2/2022 | Salk et al. |
| 11,447,818 | B2 | 9/2022 | Zhao et al. |
| 11,549,144 | B2 | 1/2023 | Salk et al. |
| 11,555,220 | B2 | 1/2023 | Salk et al. |
| 11,608,529 | B2 | 3/2023 | Salk et al. |
| 2004/0018520 | A1 | 1/2004 | Thompson |
| 2008/0108082 | A1 | 5/2008 | Rank et al. |
| 2009/0026082 | A1 | 1/2009 | Rothberg et al. |
| 2011/0245085 | A1* | 10/2011 | Rava ............... G16B 20/10 506/2 |
| 2012/0245037 | A1* | 9/2012 | Hogers ............ C12Q 1/6869 435/6.12 |
| 2013/0267428 | A1 | 10/2013 | Van Gelder et al. |
| 2014/0024541 | A1 | 1/2014 | Richards et al. |
| 2014/0329698 | A1 | 11/2014 | Bignell et al. |
| 2015/0044687 | A1 | 2/2015 | Schmitt et al. |
| 2015/0094961 | A1 | 4/2015 | Kermani et al. |
| 2015/0110836 | A1 | 4/2015 | Glanville |
| 2015/0275289 | A1 | 10/2015 | Otwinowski et al. |
| 2016/0319345 | A1 | 11/2016 | Gnerre et al. |
| 2017/0355984 | A1 | 12/2017 | Evans et al. |
| 2018/0037885 | A1 | 2/2018 | Lebofsky et al. |
| 2018/0142293 | A1 | 5/2018 | Schmitt et al. |
| 2018/0201992 | A1 | 7/2018 | Wu et al. |
| 2018/0223350 | A1 | 8/2018 | Galvin et al. |
| 2018/0363051 | A1 | 12/2018 | Schmitt et al. |
| 2018/0363052 | A1 | 12/2018 | Schmitt et al. |
| 2018/0363053 | A1 | 12/2018 | Schmitt et al. |
| 2019/0085384 | A1 | 3/2019 | Zhao et al. |
| 2019/0093160 | A1 | 3/2019 | Schmitt et al. |
| 2019/0093161 | A1 | 3/2019 | Schmitt et al. |
| 2019/0093162 | A1 | 3/2019 | Schmitt et al. |
| 2019/0119748 | A1 | 4/2019 | Schmitt et al. |
| 2019/0119749 | A1 | 4/2019 | Schmitt et al. |
| 2019/0271040 | A1 | 9/2019 | Salk et al. |
| 2019/0284626 | A1 | 9/2019 | Salk et al. |
| 2019/0284627 | A1 | 9/2019 | Salk et al. |
| 2019/0292597 | A1 | 9/2019 | Salk et al. |
| 2019/0323082 | A1 | 10/2019 | Salk et al. |
| 2019/0338358 | A1 | 11/2019 | Salk et al. |
| 2019/0352714 | A1 | 11/2019 | Salk et al. |
| 2020/0318185 | A1 | 10/2020 | Salk et al. |
| 2020/0392580 | A1 | 12/2020 | Salk et al. |
| 2021/0079462 | A1 | 3/2021 | Wu et al. |
| 2021/0324470 | A1 | 10/2021 | Salk et al. |
| 2021/0371920 | A1 | 12/2021 | Salk et al. |
| 2021/0371921 | A1 | 12/2021 | Salk et al. |
| 2021/0371922 | A1 | 12/2021 | Salk et al. |
| 2021/0371923 | A1 | 12/2021 | Salk et al. |
| 2021/0371924 | A1 | 12/2021 | Salk et al. |
| 2021/0381048 | A1 | 12/2021 | Salk et al. |
| 2022/0010376 | A1 | 1/2022 | Salk et al. |
| 2022/0017961 | A1 | 1/2022 | Salk et al. |
| 2022/0195523 | A1 | 6/2022 | Salk et al. |
| 2022/0290231 | A1 | 9/2022 | Salk et al. |

FOREIGN PATENT DOCUMENTS

| | | | |
|---|---|---|---|
| JP | 2018514207 A | | 6/2018 |
| RU | 2565550 C2 | | 10/2015 |
| WO | WO 91/06678 | | 5/1991 |
| WO | WO 95/23875 A1 | | 9/1995 |
| WO | WO 98/044151 | | 10/1998 |
| WO | WO 00/018957 | | 4/2000 |
| WO | WO 2004/018497 A2 | | 3/2004 |
| WO | WO 2005/065814 A1 | | 7/2005 |
| WO | WO 2006/064199 | | 6/2006 |
| WO | WO 2007/010251 A2 | | 1/2007 |
| WO | WO 2007/123744 A2 | | 11/2007 |
| WO | WO-2011139797 A2 | | 11/2011 |
| WO | WO 2012/142213 A2 | | 10/2012 |
| WO | WO 2012/142213 A3 | | 10/2012 |
| WO | WO-2012142213 A2 * | 10/2012 | ............ C12Q 1/6806 |
| WO | WO 2013/009175 A1 | | 1/2013 |
| WO | WO-2013009175 A1 * | 1/2013 | ............ C12Q 1/6827 |
| WO | WO 2013/138510 A9 | | 9/2013 |
| WO | WO 2013/142389 A1 | | 9/2013 |
| WO | WO-2013142389 A1 * | 9/2013 | ............ C12Q 1/6806 |
| WO | WO 2013/173394 A2 | | 11/2013 |
| WO | WO-2013181170 A1 | | 12/2013 |
| WO | WO 2014/142850 A1 | | 9/2014 |
| WO | WO 2014/145820 A2 | | 9/2014 |
| WO | WO 2014/151117 A1 | | 9/2014 |
| WO | WO 2015/058052 A1 | | 4/2015 |
| WO | WO 2015/100427 A1 | | 7/2015 |
| WO | WO 2015/106941 A1 | | 7/2015 |
| WO | WO 2015/179493 A1 | | 11/2015 |
| WO | WO 2016/040901 A1 | | 3/2016 |
| WO | WO 2016/168351 A1 | | 10/2016 |
| WO | WO 2016/0176091 A1 | | 11/2016 |
| WO | WO 2017/100441 A1 | | 6/2017 |
| WO | WO 2017/214557 A1 | | 12/2017 |
| WO | WO-2018136248 A1 | | 7/2018 |
| WO | WO-2018175997 A1 | | 9/2018 |
| WO | WO 2019/055715 | | 3/2019 |
| WO | WO-2019094651 A1 | | 5/2019 |
| WO | WO-2019160998 A1 | | 8/2019 |
| WO | WO-2019178577 A1 | | 9/2019 |
| WO | WO-2019222560 A1 | | 11/2019 |
| WO | WO-2020014693 A1 | | 1/2020 |
| WO | WO-2020081743 A1 | | 4/2020 |
| WO | WO-2021022237 A1 | | 2/2021 |

OTHER PUBLICATIONS

Chinese First Office Action dated Dec. 2, 2020 issued in Application No. CN 201680036120.4.
Mexican First Office Action dated Feb. 8, 2021 issued in Application No. MX/A/2017/013775.
Bystrykh, L., "Generalized DNA Barcode Design Based on Hamming Codes" PLoS ONE 7(5), e36852, May 2012, pp. 1-8. doi:10.1371/journal.pone.0036852.
Shiroguchi, et al., "Digital RNA sequencing minimizes sequence-dependent bias and amplification noise with optimized single-molecule barcodes" PNAS, vol. 109, No. 4, Jan. 24, 20212, pp. 1347-1352.
U.S. Office Action dated Sep. 5, 2017 issued in U.S. Appl. No. 15/130,668.
U.S. Final Office Action dated May 11, 2018 issued in U.S. Appl. No. 15/130,668.
U.S. Office Action dated Apr. 9, 2019 issued in U.S. Appl. No. 15/130,668.
Final Office Action dated Nov. 22, 2019 issued in U.S. Appl. No. 15/130,668.
Notice of Allowance dated Jul. 20, 2020 issued in U.S. Appl. No. 15/130,668.
U.S. Office Action dated Mar. 20, 2020 issued in U.S. Appl. No. 15/863,737.
U.S. Notice of Allowance dated Jul. 16, 2020 issued in U.S. Appl. No. 15/863,737.
International Search Report and Written Opinion dated Jun. 23, 2016 issued in No. PCT/US2016/028430.
International Preliminary Report on Patentabiltiy dated Nov. 9, 2017 issued in No. PCT/US2016/028430.
International Search Report and Written Opinion dated Nov. 7, 2018 issued in No. PCT/US2018/050968.
International Search Report and Written Opinion dated Apr. 5, 2018 issued in No. PCT/US2018/012669.
International Preliminary Report on Patentability dated Aug. 1, 2019 issued in No. PCT/US2018/012669.
European Examination Report dated Oct. 24, 2018 in EP Application No. 16720269.6.
New Zealand First Examination Report dated Jun. 25, 2018 in NZ Application No. 736609.
International Preliminary Report on Patentability dated Nov. 18, 2019 in No. PCT/US2018/050968.
Indian Office Action dated Mar. 3, 2020 issued in Application No. 201717040437.

(56) References Cited

OTHER PUBLICATIONS

Brazilian Office Action and Search Report dated Jan. 7, 2020 issued in No. BR 11 2017 024118.8.
Alcaide et al., "Targeted error-suppressed quantification of circulating tumor DNA using semi-degenerate barcoded adapters and biotinylated baits," Scientific Reports, vol. 7, No. 1, Sep. 2017, pp. 1-19.
Alnemri, et al., "Activation of internucleosomall DNA cleavage in human CEM lymphocytes by glucocorticoid and novobiocin. *Evidence for a non-Ca2(+)-requiring mechanism(s)*", Journal of Biol, Chem., vol. 265, No. 28 (1990) pp. 17323-17333.
Altschul, et al., "Basic Local Alignment Search Tool," J. Mol. Biol. (1990) vol. 215, pp. 403-410.
Bentley, et al., "Accurate whole human genome sequencing using reversible terminator chemistry," Nature, vol. 456, Nov. 2008, pp. 53-59.
Botexatu, et al., "Genetic Analysis of DNA Excreted in Urine: A New Approach for Detecting Specific Genomic DNA Sequences from Cells Dying in an Organism," Clinical Chemistry, vol. 46, No. 8, 2000, pp. 1078-1084.
Burrows-Wheeler Aligner (BWA) [Webpage] pp. 1-2. [retrieved on Feb. 12, 2018] <URL:http://bio-bwa.sourceforge.net/>.
Casbon, et al. "A method for counting PCR template molecules with application to next-generation sequencing," Nucleic Acids Research, vol. 39, No. 12, Apr. 13, 2011, pp. 1-8.
Chen et al., "Microsatellite alterations in plasma DNA of small cell lung cancer patients," Nature Medicine, vol. 2, No. 9, Sep. 1996, pp. 1033-1035.
Craig et al., "Ordering of cosmid clones covering the Herpes simplex virus type I (HSV-I) genome: a test case for fingerprinting by hybridisation" Nucleic Acids Research, vol. 18, pp. 2653-2660 (1990).
Fan et al., "Analysis of the Size Distributions of Fetal and Maternal Cell-Free DNA by Paired-End Sequencing," Clinical Chemistry, vol. 56, No. 8 (2010) pp. 1-8.
Fan et al., "Noninvasive diagnosis of fetal aneuploidy by shotgun sequencing DNA from maternal blood," PNAS, vol. 105, No. 42, Oct. 21, 2008, pp. 16266-16271.
Forshew et al. (2012) "Noninvasive identification and monitoring of cancer mutations by targeted deep sequencing of plasma DNA," Science Translational Medicine, vol. 4 Issue 136, 136ra68.
Genomeweb [webpage] "Stanford team develops two-step error correction method for liquid biopsy assay", Mar. 28, 2016, pp. 1-3. [retrieved on Apr. 13, 2016] <URL:https://www.genomeweb.com/sequencing-technology/stanford-team-develops-two-step-error-correction-method-liquid-biopsy-assay>.
Gregory et al., "Targeted single molecule mutation detection with massively parallel sequencing," Nucleic Acids Research, vol. 44, No. 3, Sep. 17, 2015, pp. 1-11.
Genome [webpage] "Human Genome Browser—hg19 assembly", pp. 1-2. [retrieved on Feb. 12, 2018] <URL:https://genome.ucsc.edu/cgi-bin/hgGateway?db=hg19>.
Genome [webpage] "Human Genome Browser—hg19 assembly", pp. 1-2. [retrieved on Feb. 12, 2018] <URL:https://genome.ucsc.edu/cgi-bin/hgGateway?org=Human&db=hg18&hgsid=166260105>.
Huang et al., [webpage] "ART: a next-generation sequencing read simulator" Bioinformatics, vol. 28, No. 4 (2012) pp. 593-594. [retrieved Feb. 12, 2018] <URL:https://www.niehs.nih.gov/research/resources/software/biostatistics/art/>.
Jabara et al., "Accurate sampling and deep sequencing of the HIV-1 protease gene using a Primer ID," PNAS, vol. 108, No. 50, Dec. 13, 2011, pp. 20166-20171.
Kennedy et al., (2013) "Ultra-sensitive sequencing reveals an age-related increase in somatic mitochondrial mutations that are inconsistent with oxidative damage," PLOS Genetics, vol. 9 Issue 9, e1003794.
Kennedy et al., (2014) "Detecting ultralow-frequency mutations by duplex sequencing," Nature Protocols, Nature America, Inc., vol. 9 No. 11, 2586.
Kinde et al., "Detection and qualification of rare mutations with massively parallel sequencing," PNAS, vol. 108, No. 23, Jun. 7, 2011, pp. 9530-9535.
Kivioja et al., "Counting absolute numbers of molecules using unique molecular identifiers," Nature Methods, vol. 9, No. 1, Jan. 2012, pp. 72-74; and supplementary materials. <doi:10.1038/NMETH.1778>.
Koide et al. "Fragmentation of cell-free fetal DNA in plasma and urine of pregnant women," Prenatal Diagnosis, vol. 25, 2005, pp. 604-607.
Kozarewa et al., "Amplification-free Illumina sequencing-library preparation facilitates improved mapping and assembly of GC-biased genomes," UKPMC Funders Group, Nat. Methods., Apr. 2009, vol. 6, No. 4, pp. 291-295.
Langmead et al., "Ultrafast and memory-efficient alignment of short DNA sequences to the human genome," Genome Biology, vol. 10, No. 3, Article R25, Mar. 4, 2009, pp. 1-10.
Lo et al., "Presence of fetal DNA in maternal plasma and serum," The Lancet, vol. 350, Aug. 1997, pp. 485-487.
Metzker et al., "Sequencing technologies—the next generation," Nature Reviews: Genetics, vol. 11, Jan. 2010, pp. 31-46.
Hannonlab [webpage] "nxCode-DNA Barcode Designer and Decoder for Next-Gen Sequencing" p. 1. [retrieved on Feb. 12, 2018] <URL:http://hannonlab.cshl.edu/nxCode/nxCode/main.html>.
Schmitt et al. (2015) "Sequencing small genomic targets with high efficiency and extreme accuracy," Nature Methods, 12(5): 423-425.
Smith et al., "UMI-tools: Modeling sequencing errors in Unique Molecular Identifiers to improve quantification accuracy," Genome Research, vol. 27, No. 3, Jan. 2017, pp. 491-499.
Su et al., "Human Urine Contains Small, 150 to 250 Nucleotide-Sized, Soluble DNA Devrived from the Circulation and May Be Useful in the Detection of Colorectal Cancer," Journal of Molecular Diagnostics, vol. 6, No. 2, May 2004, pp. 101-107.
Varscan, "http://varscan.sourceforge.net/", Version 2.2.5, Version 2.2.5, Apr. 2011, 13, 77.
Voelkerding et al., "Next-Generation Sequencing: From Basic Research to Diagnostics," Clinical Chemistry, vol. 55, No. 4 (2009) pp. 641-658.
Illumina [webpage] "Data Processing of Nextera Mate Pair Reads on Illumina Sequencing Platforms," Technical Notes: Sequencing, (2012), pp. 1-6. <URLLhttp://illumina.documents/products/technotes/technote_nextera_matepair_data_processing.pdf>.
Extended European Search Report dated Sep. 11, 2020 issued in EP Application No. 20161152.2.
AU Office action dated Jul. 2, 2021, in AU Application No. AU2018331434.
Buschmann, T. et al., "Levenshtein Error-correcting Barcodes for Multiplexed DNA Sequencing," 2013, BioMed Central bioinformatics, vol. 14, Article No. 272, pp. 1-10.
Canadian Office Action dated Feb. 16, 2022 in CA Application No. 3,109,403.
Japanese Office Action dated Nov. 15, 2021 issued in Application No. JP 2019-559268.
U.S. Final Office Action dated Mar. 7, 2022 issued in U.S. Appl. No. 16/129,099.
U.S. Corrected Notice of Allowance dated Jun. 10, 2022, in U.S. Appl. No. 16/129,099.
U.S. Notice of Allowance dated May 18, 2022, in U.S. Appl. No. 16/129,099.
U.S. Office Action dated Aug. 3, 2021 issued in U.S. Appl. No. 16/129,099.
European Office Action dated Sep. 1, 2021 issued in Application No. EP 20161152.2.
Extended European Search Report dated Aug. 17, 2021 issued in Application No. EP 21172159.2.
First Examination Report dated Jun. 2, 2021 issued in Application No. RU 2019122349.
Koning, et al. "Repetitive Elements May Comprise Over Two-Thirds of the Human Genome" PLoS Genetics, vol. 7, No. 12, Dec. 2011, pp. 1-12.
CA Notice of Allowance dated Apr. 14, 2022 in Application No. 3,063,750.

(56) References Cited

OTHER PUBLICATIONS

CN Office Action dated Jan. 3, 2023, in Application No. CN201880046481.6.
CN Office Action dated Oct. 20, 2022 in Application No. CN20188012772.3 with English translation.
EP Office Action dated Aug. 1, 2022, in Application No. EP18779958.
Mir, K. et al., "Short Barcodes for Next Generation Sequencing", PLOS One, vol. 8, No. 12, Dec. 1, 2013, pp. 1-8.
Turner F., "Assessment of Insert Sizes and Adapter Content in Fastq Data From NexteraXT Libraries," Frontiers in Genetics, 2014, vol. 5(5), pp. 1-6.
U.S. Non-Final Office Action dated Dec. 9, 2022 in U.S. Appl. No. 17/073,074.
U.S. Appl. No. 17/890,208, inventors Zhao et al., filed Aug. 17, 2022.
U.S. Non-Final Office Action dated Jun. 6, 2023 in U.S. Appl. No. 17/890,208.
AU Office action dated Mar. 2, 2023, in AU Application No. AU2018210188.
U.S. Notice of Allowance dated May 3, 2023 in U.S. Appl. No. 17/073,074.

\* cited by examiner (i) Standard dual index TruSeq adapter (ii) UMI replacing sample index 1 position (iii) UMIs in both P5 and P7 arms, prior to sample index reading (iv) UMIs in both P5 and P7 arms, behind sample index reading (v) Dual index adapter with a UMI in the double-stranded region (vi) Short adapter with a UMI in the double-stranded region

Figure 4E

| | 0 errors | 1 error, recoverable | 1 error, non-recoverable | 2+ errors/ 1+ indels |
|---|---|---|---|---|
| NA18506-0-4-UMI-a | 98.03% | 0.81% | 0.33% | 0.82% |
| NA18506-0-4-UMI-b | 97.21% | 1% | 0.25% | 1.53% |
| NA18506-0-4-UMI-c | 97.51% | 1.31% | 0.26% | 0.91% |
| Overall | 97.58% | 1.07% | 0.28% | 1.09% |

>98.65% of total UMIs are usable

Many of these could still be usable based on the context

Figure 10

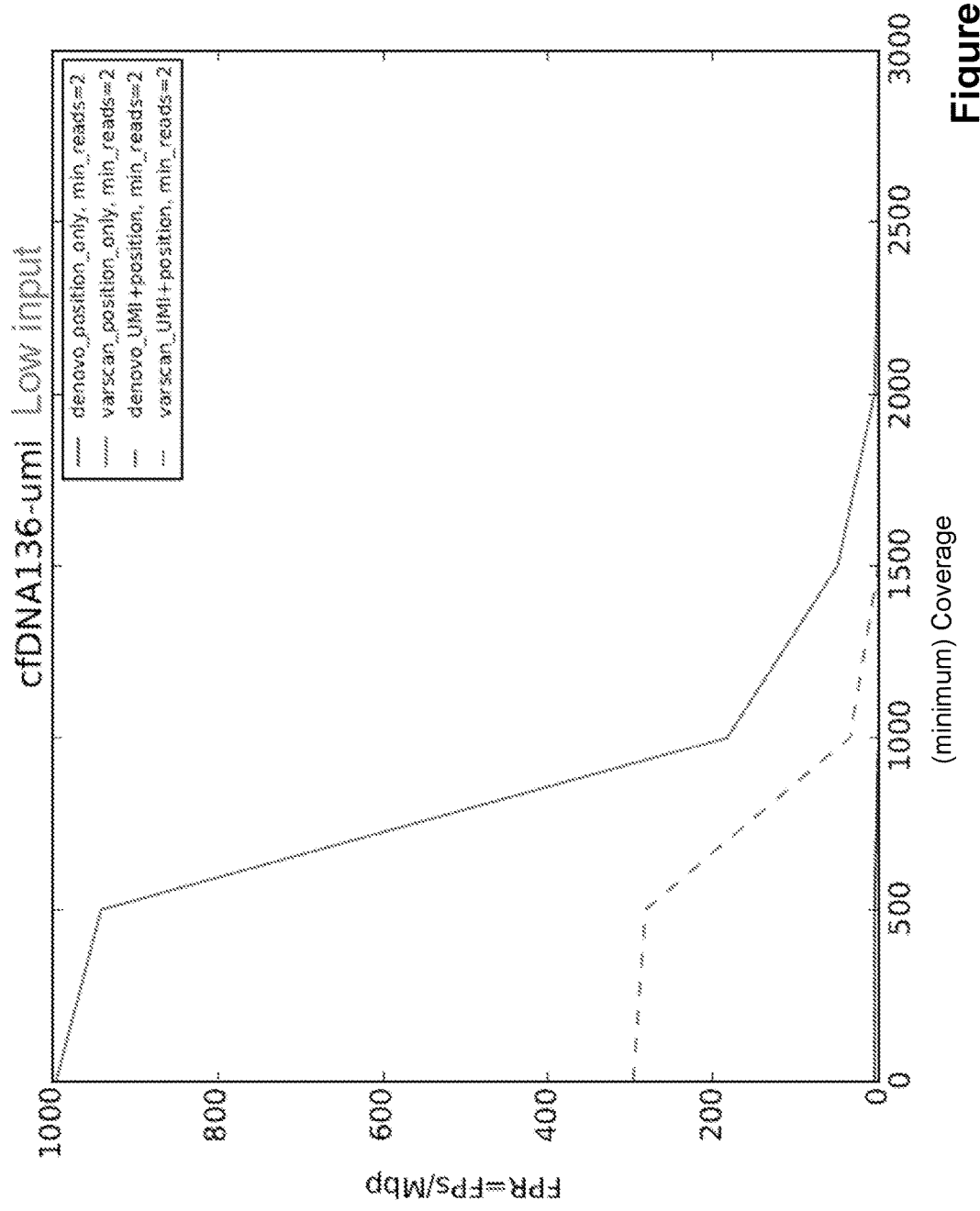

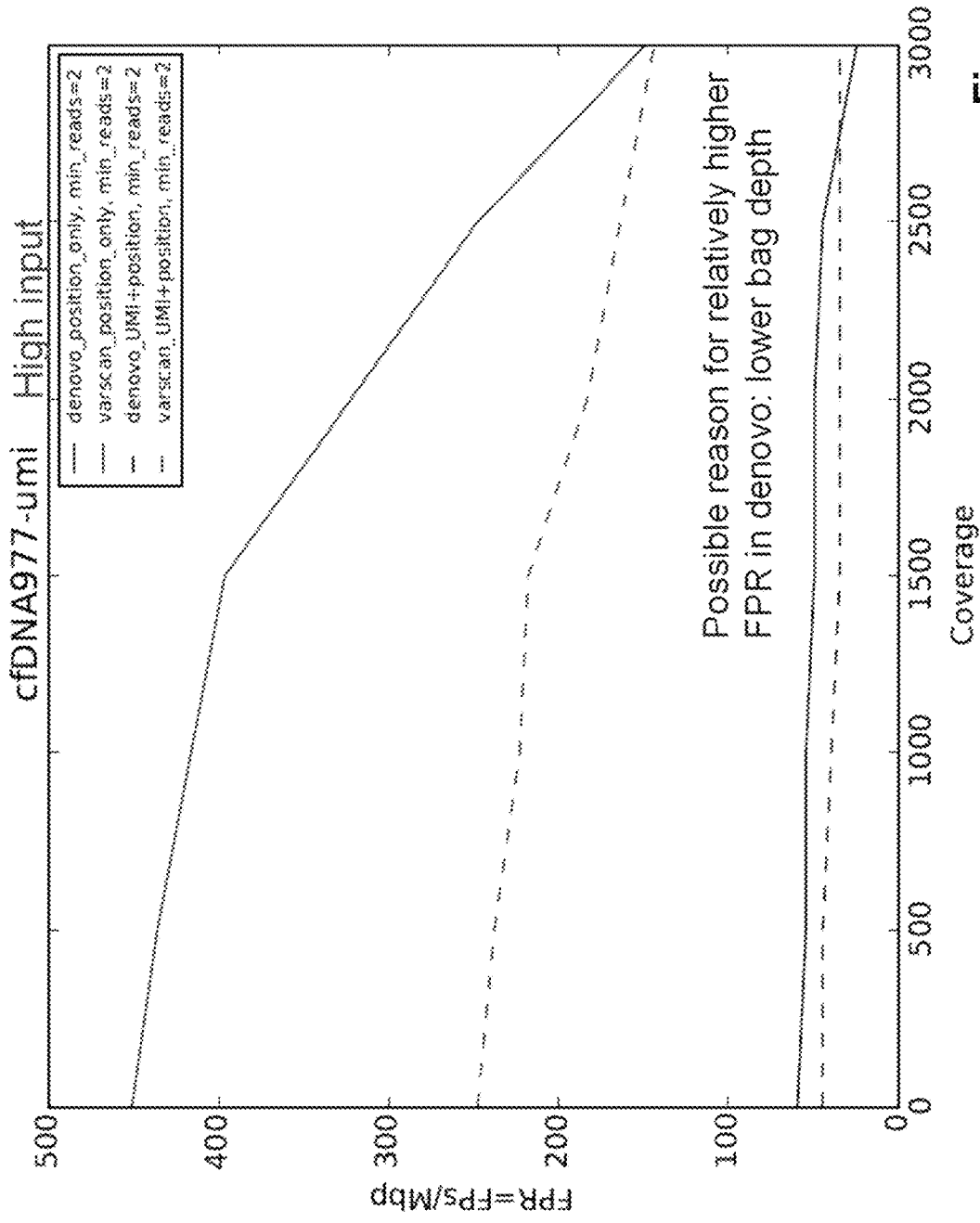

SEQUENCE LISTING

```
<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
```

```
-continued

<223> OTHER INFORMATION: Synthetic polynucleotide
<220> FEATURE:
<221> NAME/KEY: misc_feature
<222> LOCATION: (4)..(7)
<223> OTHER INFORMATION: n is a, c, g, or t
<220> FEATURE:
<221> NAME/KEY: misc_feature
<222> LOCATION: (9)..(12)
<223> OTHER INFORMATION: n is a, c, g, or t

<400> SEQUENCE: 1
ccannnnann nntgg                                                    15

<210> SEQ ID NO 2
<211> LENGTH: 45
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: n is a, c, g, or t

<400> SEQUENCE: 2
nnnntgctcg cagatcggaa gagcacacgt ctgaactcca gtcac                   45

<210> SEQ ID NO 3
<211> LENGTH: 44
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (40)..(43)
<223> OTHER INFORMATION: n is a, c, g, or t

<400> SEQUENCE: 3
cactctttcc ctacacgacg ctcttccgat ctgcgaccan nnnt                    44
```

ERROR SUPPRESSION IN SEQUENCED DNA FRAGMENTS USING REDUNDANT READS WITH UNIQUE MOLECULAR INDICES (UMIS)

CROSS REFERENCE TO RELATED APPLICATIONS

An Application Data Sheet is filed concurrently with this specification as part of the present application. Each application that the present application claims benefit of or priority to as identified in the concurrently filed Application Data Sheet is incorporated by reference herein in its entirety and for all purposes.

SEQUENCE LISTING

The instant application contains a Sequence Listing which is submitted electronically in ASCII format and is hereby incorporated by reference in its entirety. Said ASCII copy, created on Oct. 21, 2020, is named 2020-10-21_ILMNP008D1_ST25.txt and is 2 KB in size.

BACKGROUND

Next generation sequencing technology is providing increasingly high speed of sequencing, allowing larger sequencing depth. However, because sequencing accuracy and sensitivity are affected by errors and noise from various sources, e.g., sample defects, PCR during library preparation, enrichment, clustering, and sequencing, increasing depth of sequencing alone cannot ensure detection of sequences of very low allele frequency, such as in fetal cell-free DNA (cfDNA) in maternal plasma, circulating tumor DNA (ctDNA), sub-clonal mutations in pathogens. Therefore, it is desirable to develop methods for determining sequences of DNA molecules in small quantity and/or low allele frequency while suppressing sequencing inaccuracy due to various sources of errors.

SUMMARY

The disclosed implementations concern methods, apparatus, systems, and computer program products for determining nucleic acid fragment sequences using unique molecular indices (UMIs). In various implementations, sequencing methods determine the sequences of nucleic acid fragments from both strands of the nucleic acid fragments. In some implementations, the methods employ physical UMIs located on one or both strands of sequencing adapters. In some implementations, the methods also employ virtual UMIs located on both strands of the nucleic acid fragments.

One aspect of the disclosure relates to a method for sequencing nucleic acid molecules from a sample using unique molecular indices (UMIs). Each unique molecular index (UMI) is an oligonucleotide sequence that can be used to identify an individual molecule of a double-stranded DNA fragment in the sample. The method include: (a) applying adapters to both ends of double-stranded DNA fragments in the sample, wherein the adapters each include a double-stranded hybridized region, a single-stranded 5' arm, a single-stranded 3' arm, and a physical UMI on one strand or each strand of the adapters, thereby obtaining DNA-adapter products; (b) amplifying both strands of the DNA-adapter products to obtain a plurality of amplified polynucleotides; (c) sequencing the plurality of amplified polynucleotides, thereby obtaining a plurality of reads each associated with a physical UMI; (d) identifying a plurality of physical UMIs associated with the plurality of reads; (e) identifying a plurality of virtual UMIs associated with the plurality of reads, wherein each virtual UMI is a sequence found in a DNA fragment in the sample; and (f) determining sequences of the double-stranded DNA fragments in the sample using the plurality of reads obtained in (c), the plurality of physical UMIs identified in (d), and the plurality of virtual UMIs identified in (e). In some implementations, the method include operation (f) includes: (i) combining, for each of one or more of the double-stranded DNA fragments in the sample, (1) reads having a first physical UMI and at least one virtual UMI in the 5' to 3' direction and (2) reads having a second physical UMI and the at least one virtual UMI in the 5' to 3' direction to determine a consensus nucleotide sequence; and (ii) determining, for each of the one or more of the double-stranded DNA fragments in the sample, a sequence using the consensus nucleotide sequence.

In some implementations, the plurality of physical UMIs includes random UMIs. In some implementations, the plurality of physical UMIs includes nonrandom UMIs. In some implementations, every nonrandom UMI differs from every other nonrandom UMI of the adapters by at least two nucleotides at corresponding sequence positions of the nonrandom UMIs. In some implementations, the plurality of physical UMIs includes no more than about 10,000, about 1,000, about 500, or about 100 unique nonrandom UMIs. In some implementations, the plurality of physical UMIs includes about 96 unique nonrandom UMIs.

In some implementations of the methods above, applying adapters to both ends of double-stranded DNA fragments includes ligating the adapters to both ends of the double stranded DNA fragments. In some implementations, operation (f) includes using reads sharing a common physical UMI and a common virtual UMI to determine a sequence of a DNA fragment of the sample.

In some implementations of the methods above, the plurality of physical UMIs includes fewer than 12 nucleotides. In some implementations, the plurality of UMIs includes no more than 6 nucleotides. In some implementations, the plurality of UMIs includes no more than 4 nucleotides.

In some implementations, the adapters each include a physical UMI on each strand of the adapters in the double-stranded hybridized region. In some implementations, the physical UMI is at an end of the double-stranded hybridized region, said end of the double-stranded hybridized region being opposite from the 3' arm or the 5' arm, or is one nucleotide away from said end of the double-stranded hybridized region. In some implementations, the adapters each include a 5'-TGG-3' trinucleotide or a 3'-ACC-5' trinucleotide on the double-stranded hybridized region adjacent to a physical UMI. In some implementations, the adapters each include a read primer sequence on each strand of the double-stranded hybridized region.

In some implementations, the adapters each include a physical UMI on only one strand of the adapters on the single-stranded 5' arm or the single-stranded 3' arm. In some of these implementation, (f) includes: (i) collapsing reads having a same first physical UMI into a first group to obtain a first consensus nucleotide sequence; (ii) collapsing reads having a same second physical UMI into a second group to obtain a second consensus nucleotide sequence; and (iii) determining, using the first and second consensus nucleotide sequences, a sequence of one of the double-stranded DNA fragments in the sample. In some implementations, (iii)

includes: (1) obtaining, using localization information and sequence information of the first and second consensus nucleotide sequences, a third consensus nucleotide sequence, and (2) determining, using the third consensus nucleotide sequence, the sequence of one of the double-stranded DNA fragments. In some implementations, operation (e) includes identifying the plurality of virtual UMIs, while the adapters each include the physical UMI on only one strand of the adapters in the single-stranded 5' arm region or the single-stranded 3' arm region. In some implementations, (f) includes: (i) combining reads having a first physical UMI and at least one virtual UMI in the 5' to 3' direction and reads having a second physical UMI and the at least one virtual UMI in the 5' to 3' direction to determine a consensus nucleotide sequence; and (ii) determining a sequence of one of the double-stranded DNA fragments in the sample using the consensus nucleotide sequence.

In some implementations, the adapters each include a physical UMI on each strand of the adapters in a double-stranded region of the adapters, wherein the physical UMI on one strand is complementary to the physical UMI on the other strand. In some implementations, operation (f) includes: (i) combining reads having a first physical UMI, at least one virtual UMI, and a second physical UMI in the 5' to 3' direction and reads having the second physical UMI, the at least one virtual UMI, and the first physical UMI in the 5' to 3' direction to determine a consensus nucleotide sequence; and (ii) determining a sequence of one of the double-stranded DNA fragments in the sample using the consensus nucleotide sequence.

In some implementations, the adapters each include a first physical UMI on a 3' arm of the adapter and a second physical UMI on a 5' arm of the adapter, wherein the first physical UMI and the second physical UMI are not complementary to each other. In some of such implementations, (f) includes: (i) combining reads having a first physical UMI, at least one virtual UMI, and a second physical UMI in the 5' to 3' direction and reads having a third physical UMI, the at least one virtual UMI, and a fourth physical UMI in the 5' to 3' direction to determine a consensus nucleotide sequence; and (ii) determining a sequence of one of the double-stranded DNA fragments in the sample using the consensus nucleotide sequence.

In some implementations, at least some of the virtual UMIs derive from subsequences at or near the ends of the double-stranded DNA fragments in the sample.

In some implementations, one or more physical UMIs and/or one or more virtual UMIs are uniquely associated with a double-stranded DNA fragment in the sample.

In some implementations, the double-stranded DNA fragments in the sample include more than about 1,000 DNA fragments.

In some implementations, the plurality of virtual UMIs include UMIs of about 6 bp to about 24 bp. In some implementations, the plurality of virtual UMIs include UMIs of about 6 bp to about 10 bp.

In some implementations of the methods above, obtaining the plurality of reads in operation (c) includes: obtaining two pair-end reads from each of the amplified polynucleotides, where in the two pair-end reads include a long read and a short read, the long read being longer than the short read. In some of these implementations, operation (f) includes: combining read pairs associated with a first physical UMI into a first group and combining read pairs associated with a second physical UMI into a second group, wherein the first and the second physical UMIs are uniquely associated with a double-stranded fragment in the sample; and determining the sequence of the double-stranded fragment in the sample using sequence information of long reads in the first group and sequence information of long reads in the second group. In some implementations, the long read has a read length of about 500 bp or more. In some implementations, the short read has a read length of about 50 bp or less.

In some implementations, the method suppresses errors arise in one or more of the following operations: PCR, library preparation, clustering, and sequencing.

In some implementations, the amplified polynucleotides include an allele having an allele frequency lower than about 1%.

In some implementations, the amplified polynucleotides include a cell free DNA molecule originating from a tumor, and the allele is indicative of the tumor.

In some implementations, sequencing the plurality of amplified polynucleotides includes obtaining reads having at least about 100 bp.

Another aspect of the instant disclosure relates to a method for sequencing nucleic acid molecules from a sample, including (a) attaching adapters to both ends of double-stranded DNA fragments in the sample, wherein the adapters each include a double-stranded hybridized region, a single-stranded 5' arm, a single-stranded 3' arm, and a physical unique molecular index (UMI) on the single-stranded 5' arm or the single-stranded 3' arm; (b) amplifying both strands of ligation products from (a), thereby obtaining a plurality of single-stranded, amplified polynucleotides; (c) sequencing the plurality of amplified polynucleotides, thereby obtaining a plurality of reads each associated with a physical UMI; (d) identifying a plurality of physical UMIs associated with the plurality of reads; and (e) determining sequences of the double-stranded DNA fragments in the sample using the plurality of sequences obtained in (c) and the plurality of physical UMIs identified in (d).

An additional aspect of the disclosure relates to a method for sequencing nucleic acid molecules from a sample. The method includes: (a) attaching adapters to both ends of double-stranded DNA fragments in the sample, wherein the adapters each include a double-stranded hybridized region, a single-stranded 5' arm, a single-stranded 3' arm, and a physical unique molecular index (UMI) shorter than 12 nucleotides on one strand or each strand of the adapters; (b) amplifying both strands of ligation products from (a), thereby obtaining a plurality of single-stranded, amplified polynucleotides each including a physical UMI; (c) sequencing the plurality of amplified polynucleotides, thereby obtaining a plurality of reads each associated with a physical UMI; (d) identifying a plurality of physical UMIs associated with the plurality of reads; and (e) determining sequences of the double-stranded DNA fragments in the sample using the plurality of reads obtained in (c) and the plurality of physical UMIs identified in (d).

Another aspect of the instant disclosure relates a method for making a duplex sequencing adapter having a physical UMI on each strand. The method includes: providing a preliminary sequencing adapter including a double-stranded hybridized region, two single-stranded arms, and an overhang including 5'-CCANNNNANNNNTGG-3' at an end of the double-stranded hybridized region that is further away from the two single stranded arms; extending one strand of the double-stranded hybridized region using the overhang as a template, thereby producing an extension product; and applying restriction enzyme Xcm1 to digest a double-stranded end of the extension product, thereby producing the duplex sequencing adapter having a physical UMI on each strand. In some implementations, the preliminary sequencing adapter includes a read primer sequence on each strand.

A further aspect of the instant disclosure relates to a computer program product including a non-transitory machine readable medium storing program code that, when executed by one or more processors of a computer system, causes the computer system to implement a method for determining sequence information of a sequence of interest in a sample using unique molecular indices (UMIs). The program code includes: (a) code for obtaining reads of a plurality of amplified polynucleotides, wherein the plurality of amplified polynucleotides are obtained by amplifying double-stranded DNA fragments in the sample including the sequence of interest and attaching adapters to the double-stranded DNA fragments; (b) code for identifying a plurality of physical UMIs in the reads of the plurality of amplified polynucleotides, wherein each physical UMI is found in an adapter attached to one of the double-stranded DNA fragments; (c) code for identifying a plurality of virtual UMIs in the received reads of the plurality of amplified polynucleotides, wherein each virtual UMI is found in an individual molecule of one of the double-stranded DNA fragments; and (c) code for determining sequences of the double-stranded DNA fragments using the reads of the plurality of amplified polynucleotides, the plurality of physical UMIs, and the plurality of virtual UMIs, thereby reducing errors in the determined sequences of the double-stranded DNA fragments. In some implementations, the adapters each include a double-stranded hybridized region, a single-stranded 5' arm, a single-stranded 3' arm, and a physical unique molecular index (UMI) on one strand or each strand of the adapters.

In some implementations, the code for determining sequences of the double-stranded DNA fragments includes: (i) code for collapsing reads having a same first physical UMI into a first group to obtain a first consensus nucleotide sequence; (ii) code for collapsing reads having a same second physical UMI into a second group to obtain a second consensus nucleotide sequence; and (iii) code for determining, using the first and second consensus nucleotide sequences, a sequence of one of the double-stranded DNA fragments in the sample.

In some implementations, the code for determining sequences of the double-stranded DNA fragments includes: (i) code for combining sequence reads having a first physical UMI, at least one virtual UMI, and a second physical UMI in the 5' to 3' direction and sequence reads having the second physical UMI, the at least one virtual UMI, and the first physical UMI in the 5' to 3' direction to determine a consensus nucleotide sequence; and (ii) code for determining a sequence of one of the double-stranded DNA fragments in the sample using the consensus nucleotide sequence.

An additional aspect of the disclosure relates to a computer system, including: one or more processors; system memory; and one or more computer-readable storage media. The media has stored thereon computer-executable instructions that causes the computer system to implement a method to determine sequence information of a sequence of interest in a sample using unique molecular indices (UMIs), which are oligonucleotide sequences that can be used to identify individual molecules of double-stranded DNA fragments in the sample. The instructions includes: (a) receiving reads of a plurality of amplified polynucleotides, wherein the plurality of amplified polynucleotides are obtained by amplifying double-stranded DNA fragments in the sample including the sequence of interest and attaching adapters to the double-stranded DNA fragments; (b) identifying a plurality of physical UMIs in the received reads of the plurality of amplified polynucleotides, wherein each physical UMI is found in an adapter attached to one of the double-stranded DNA fragments; (c) identifying a plurality of virtual UMIs in the received reads of the plurality of amplified polynucleotides, wherein each virtual UMI is found in an individual molecule of one of the double-stranded DNA fragments; and (d) determining sequences of the double-stranded DNA fragments using the sequences of the plurality of amplified polynucleotides, the plurality of physical UMIs, and the plurality of virtual UMIs, thereby reducing errors in the determined sequences of the double-stranded DNA fragments.

In some implementations, determining sequences of the double-stranded DNA fragments includes: (i) collapsing reads having a same first physical UMI into a first group to obtain a first consensus nucleotide sequence; (ii) collapsing reads having a same second physical UMI into a second group to obtain a second consensus nucleotide sequence; and (iii) determining, using the first and second consensus nucleotide sequences, a sequence of one of the double-stranded DNA fragments.

In some implementations, determining sequences of the double-stranded DNA fragments includes: (i) combining reads having a first physical UMI, at least one virtual UMI, and a second physical UMI in the 5' to 3' direction and reads having the second physical UMI, the at least one virtual UMI, and the first physical UMI in the 5' to 3' direction to determine a consensus nucleotide sequence; and (ii) determining a sequence of one of the double-stranded DNA fragments using the consensus nucleotide sequence.

One aspect of the disclosure provides methods for sequencing nucleic acid molecules from a sample using nonrandom unique molecular indices (UMIs). The methods involve: (a) applying adapters to both ends of DNA fragments in the sample, wherein the adapters each include a double-stranded hybridized region, a single-stranded 5' arm, a single-stranded 3' arm, and a nonrandom unique molecular index (UMI) on one strand or each strand of the adapters, thereby obtaining DNA-adapter products; (b) amplifying the DNA-adapter products to obtain a plurality of amplified polynucleotides; (c) sequencing the plurality of amplified polynucleotides, thereby obtaining a plurality of reads associated with a plurality of nonrandom UMIs; (d) from the plurality of reads, identifying reads sharing a common nonrandom UMI; and (e) from the identified reads sharing the common nonrandom UMI, determining the sequence of at least a portion of a DNA fragment, from the sample, having an applied adaptor with the common non-random UMI.

In some implementations, a method further involves: from the reads sharing the common nonrandom UMI, selecting reads sharing both the common nonrandom UMI and a common read position, where determining the sequence of the DNA fragment in (e) uses only reads sharing both the common nonrandom UMI and the common read position in a reference sequence. In some implementations, every nonrandom UMI differs from every other nonrandom UMI by at least two nucleotides at corresponding sequence positions of the nonrandom UMIs.

Another aspect of the disclosure relates to methods for sequencing nucleic acid molecules from a sample using nonrandom unique molecular indices (UMIs). In some implementations, a method involves: (a) applying adapters to both ends of double-stranded DNA fragments in the sample, wherein the adapters each include a double-stranded hybridized region, a single-stranded 5' arm, a single-stranded 3' arm, and a nonrandom unique molecular index (UMI) on one strand or each strand of the adapters, thereby obtaining DNA-adapter products, wherein the nonrandom UMI can be combined with other information to uniquely identify an individual molecule of the double-stranded DNA fragments; (b) amplifying both strands of the DNA-adapter products to obtain a plurality of amplified polynucleotides; (c) sequencing the plurality of amplified polynucleotides, thereby obtaining a plurality of reads each associated with a nonrandom UMI; (d) identifying a plurality of nonrandom UMIs associated with the plurality of reads; and (e) using the plurality of reads and the plurality of nonrandom UMIs to determine sequences of the double-stranded DNA fragments in the sample.

In some implementations, using the plurality of reads and the plurality of nonrandom UMIs to determine the sequences of the double-stranded DNA fragments in the sample involves: identifying reads sharing a common nonrandom UMI, and using the identified reads to determine a sequence of a DNA fragment in the sample. In some implementations, using the plurality of reads and the plurality of nonrandom UMIs to determine the sequences of the double-stranded DNA fragments in the sample involves: identifying reads sharing a common nonrandom UMI and a common read position, and using the identified reads to determine a sequence of a DNA fragment in the sample.

In some implementations, using the plurality of reads and the plurality of nonrandom UMIs to determine sequences of the double-stranded DNA fragments in the sample involves: identifying reads sharing a common nonrandom UMI and a common virtual UMI, wherein the common virtual UMI is found in a DNA fragment in the sample; and using the identified reads to determine a sequence of the DNA fragment in the sample.

In some implementations, using the plurality of reads and the plurality of nonrandom UMIs to determine sequences of the double-stranded DNA fragments in the sample involves: identifying reads sharing a common nonrandom UMI, a common read position, and a common virtual UMI, wherein the common virtual UMI is found in a DNA fragment in the sample; and using the identified reads to determine a sequence of the DNA fragment in the sample.

In some implementations, every nonrandom UMI differs from every other nonrandom UMI of the adapters by at least two nucleotides at corresponding sequence positions of the nonrandom UMIs. In some implementations, the adapters each include a physical UMI on each strand of the adapters in the double-stranded hybridized region. In some implementations, the plurality of nonrandom UMIs includes no more than about 10,000, about 1,000, or about 100 unique nonrandom UMIs. In some implementations, the plurality of nonrandom UMIs includes about 96 unique nonrandom UMIs.

In some implementations, the plurality of reads each includes a nonrandom UMI. In some implementations, the plurality of reads each either includes a nonrandom UMI or is associated with a nonrandom UMI through a paired-end read. In some implementations, the plurality of amplified polynucleotides each has a nonrandom UMI on one end or has a first nonrandom UMI on a first end and a second nonrandom UMI on a second end.

System, apparatus, and computer program products are also provided for determining DNA fragment sequences implementing the methods disclosed.

One aspect of the disclosure provides a computer program product including a non-transitory machine readable medium storing program code that, when executed by one or more processors of a computer system, causes the computer system to implement a method to determine sequence information of a sequence of interest in a sample using unique molecular indices (UMIs). The program code includes instructions to perform the methods above.

Although the examples herein concern humans and the language is primarily directed to human concerns, the concepts described herein are applicable to nucleic acids from any virus, plant, animal, or other organism, and to populations of the same (metagenomes, viral populations, etc.) These and other features of the present disclosure will become more fully apparent from the following description, with reference to the figures, and the appended claims, or may be learned by the practice of the disclosure as set forth hereinafter.

INCORPORATION BY REFERENCE

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

BRIEF DESCRIPTION OF THE DRAWINGS

FIGS. 4A-4E illustrates how methods as disclosed herein can suppress different sources of error in determining the sequence of a double stranded DNA fragment.

FIG. 10 shows different errors occur in three samples processed with random UMIs in tabular form.

FIGS. 11B-D show selectivity (i.e., false positive rate) of calling somatic mutation and CNV in three cfDNA samples having increasing sample inputs using the two collapsing methods with two different tools: VarScan and Denovo.

DETAILED DESCRIPTION

Figure 1A:
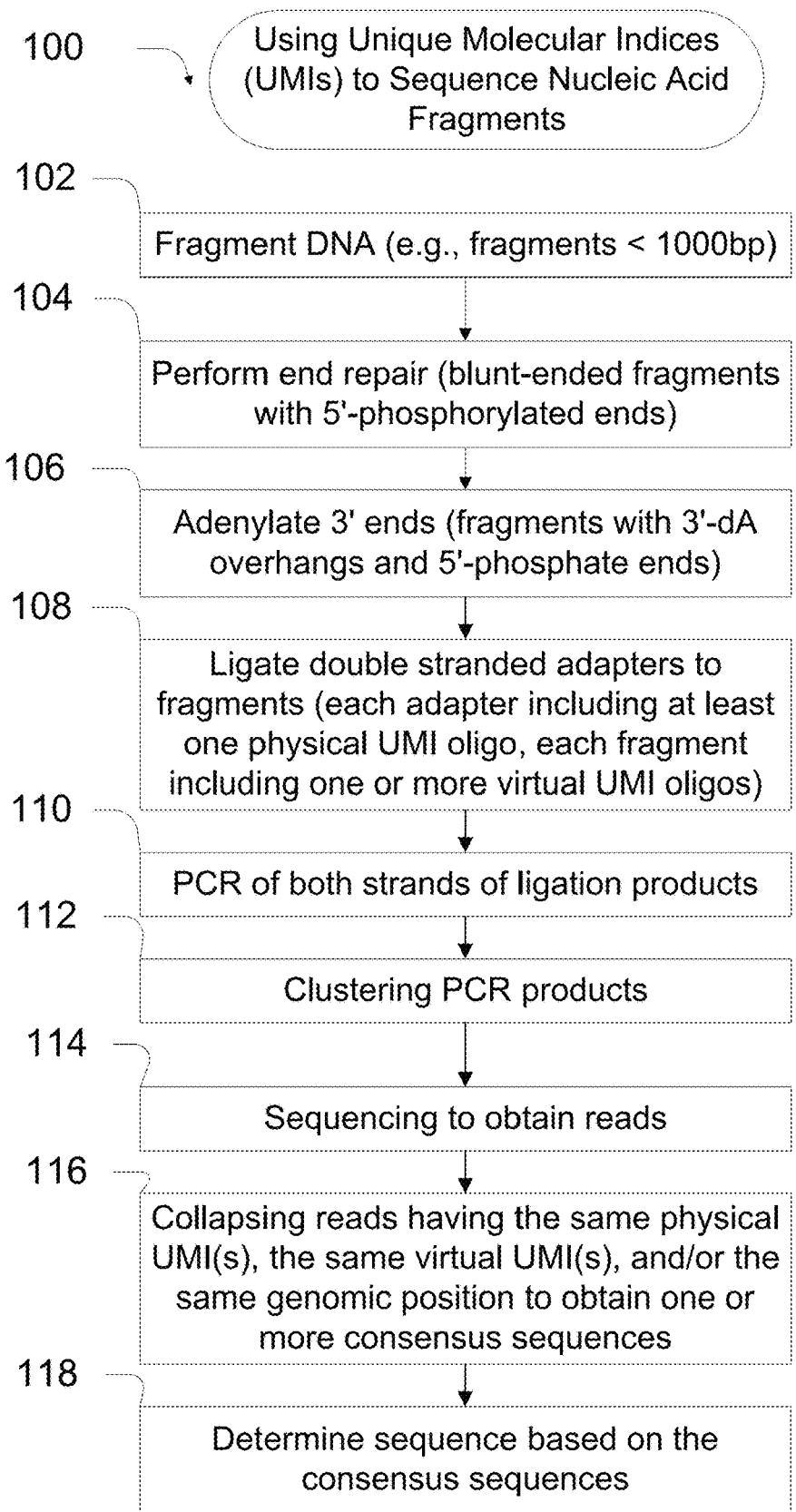
FIG. 1A is a flow chart illustrating an example workflow using UMIs to sequence nucleic acid fragments.

The disclosure concerns methods, apparatus, systems, and computer program products for sequencing nucleic acids, especially nucleic acids with limited quantity or low concentration, such as fetal cfDNA in maternal plasma or circulating tumor DNA (ctDNA) in a cancer patient's blood.

Unless otherwise indicated, the practice of the methods and systems disclosed herein involves conventional techniques and apparatus commonly used in molecular biology, microbiology, protein purification, protein engineering, protein and DNA sequencing, and recombinant DNA fields that are within the skill of the art. Such techniques and apparatus are known to those of skill in the art and are described in numerous texts and reference works (See e.g., Sambrook et al., "Molecular Cloning: A Laboratory Manual," Third Edition (Cold Spring Harbor), [2001]).

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art.

Definitions

As used herein, the singular terms "a," "an," and "the" include the plural reference unless the context clearly indicates otherwise.

Unless otherwise indicated, nucleic acids are written left to right in 5' to 3' orientation and amino acid sequences are written left to right in amino to carboxy orientation, respectively.

Unique molecular indices (UMIs) are sequences of nucleotides applied to or identified in DNA molecules that may be used to distinguish individual DNA molecules from one another. Since UMIs are used to identify DNA molecules, they are also referred to as unique molecular identifiers. See, e.g., Kivioja, Nature Methods 9, 72-74 (2012). UMIs may be sequenced along with the DNA molecules with which they are associated to determine whether the read sequences are those of one source DNA molecule or another. The term "UMI" is used herein to refer to both the sequence information of a polynucleotide and the physical polynucleotide per se.

Commonly, multiple instances of a single source molecule are sequenced. In the case of sequencing by synthesis using Illumina's sequencing technology, the source molecule may be PCR amplified before delivery to a flow cell. Whether or not PCR amplified, the individual DNA molecules applied to flow cell are bridge amplified or ExAmp amplified to produce a cluster. Each molecule in a cluster derives from the same source DNA molecule but is separately sequenced. For error correction and other purposes, it can be important to determine that all reads from a single cluster are identified as deriving from the same source molecule. UMIs allow this grouping. A DNA molecule that is copied by amplification or otherwise to produce multiple instances of the DNA molecule is referred to as a source DNA molecule.

UMIs are similar to bar codes, which are commonly used to distinguish reads of one sample from reads of other samples, but UMIs are instead used to distinguish one source DNA molecule from another when many DNA molecules are sequenced together. Because there may be many more DNA molecules in a sample than samples in a sequencing run, there are typically many more distinct UMIs than distinct barcodes in a sequencing run.

As mentioned, UMIs may be applied to or identified in individual DNA molecules. In some implementations, the UMIs may be applied to the DNA molecules by methods that physically link or bond the UMIs to the DNA molecules, e.g., by ligation or transposition through polymerase, endonuclease, transposases, etc. These "applied" UMIs are therefore also referred to as physical UMIs. In some contexts, they may also be referred to as exogenous UMIs. The UMIs identified within source DNA molecules are referred to as virtual UMIs. In some context, virtual UMIs may also be referred to as endogenous UMI.

Physical UMIs may be defined in many ways. For example, they may be random, pseudo-random or partially random, or non-random nucleotide sequences that are inserted in adapters or otherwise incorporated in source DNA molecules to be sequenced. In some implementations, the physical UMIs may be so unique that each of them is expected to uniquely identify any given source DNA molecule present in a sample. The collection of adapters is generated, each having a physical UMI, and those adapters are attached to fragments or other source DNA molecules to be sequenced, and the individual sequenced molecules each has a UMI that helps distinguish it from all other fragments. In such implementations, a very large number of different physical UMIs (e.g., many thousands to millions) may be used to uniquely identify DNA fragments in a sample.

Of course, the physical UMI must have a sufficient length to ensure this uniqueness for each and every source DNA molecule. In some implementations, a less unique molecular identifier can be used in conjunction with other identification techniques to ensure that each source DNA molecule is uniquely identified during the sequencing process. In such implementations, multiple fragments or adapters may have the same physical UMI. Other information such as alignment location or virtual UMIs may be combined with the physical UMI to uniquely identify reads as being derived from a single source DNA molecule/fragment. In some implementations, adaptors include physical UMIs limited to a relatively small number of nonrandom sequences, e.g., 96 nonrandom sequences. Such physical UMIs are also referred to as nonrandom UMIs. In some implementations, the nonrandom UMIs may be combined with sequence position information and/or virtual UMIs to identify reads attributable to a same source DNA molecule. The identified reads may be collapsed to obtain a consensus sequence that reflects the sequence of the source DNA molecule as described herein.

A "virtual unique molecular index" or "virtual UMI" is a unique sub-sequence in a source DNA molecule. In some implementations, virtual UMIs are located at or near the ends of the source DNA molecule. One or more such unique end positions may alone or in conjunction with other information uniquely identify a source DNA molecule. Depending on the number of distinct source DNA molecules and the number of nucleotides in the virtual UMI, one or more virtual UMIs can uniquely identify source DNA molecules in a sample. In some cases, a combination of two virtual unique molecular identifiers is required to identify a source DNA molecule. Such combinations may be extremely rare, possibly found only once in a sample. In some cases, one or more virtual UMIs in combination with one or more physical UMIs may together uniquely identify a source DNA molecule.

A "random UMI" may be considered a physical UMI selected as a random sample, with or without replacement, from a set of UMIs consisting of all possible different oligonucleotide sequences given one or more sequence lengths. For instance, if each UMI in the set of UMIs has n nucleotides, then the set includes $4^n$ UMIs having sequences that are different from each other. A random sample selected from the $4^n$ UMIs constitutes a random UMI.

Conversely, a "nonrandom UMI" as used herein refers to a physical UMI that is not a random UMI. In some embodiments, available nonrandom UMIs are predefined for a particular experiment or application. In certain embodiments, rules are used to generate sequences for a set or select a sample from the set to obtain a nonrandom UMI. For instance, the sequences of a set may be generated such that the sequences have a particular pattern or patterns. In some implementations, each sequence differs from every other sequence in the set by a particular number of (e.g., 2, 3, or 4) nucleotides. That is, no nonrandom UMI sequence can be converted to any other available nonrandom UMI sequence by replacing fewer than the particular number of nucleotides. In some implementations, a nonrandom UMI is selected from a set of UMIs including fewer than all possible UMIs given a particular sequence length. For instance, a nonrandom UMI having 6 nucleotides may be selected from a total of 96 different sequences (instead of a total of $4^6=4096$ possible different sequences). In other implementations, sequences are not randomly selected from a set. Instead, some sequences are selected with higher probability than other sequences.

In some implementations where nonrandom UMIs are selected from a set with fewer than all possible different sequences, the number of nonrandom UMIs is fewer, sometimes significantly so, than the number of source DNA molecules. In such implementations, nonrandom UMI information may be combined with other information, such as virtual UMI and/or sequence information, to identify sequence reads deriving from a same source DNA molecule.

The term "paired end reads" refers to reads obtained from paired end sequencing that obtains one read from each end of a nucleic fragment. Paired end sequencing involves fragmenting DNA into sequences called inserts. In some protocols such as some used by Illumina, the reads from shorter inserts (e.g., on the order of tens to hundreds of bp) are referred to as short-insert paired end reads or simply paired end reads. In contrast, the reads from longer inserts (e.g., on the order of several thousands of bp) are referred to as mate pair reads. In this disclosure, short-insert paired end reads and long-insert mate pair reads may both be used and are not differentiated with regard to the process for determining sequences of DNA fragments. Therefore, the term "paired end reads" may refer to both short-insert paired end reads and long-insert mate pair reads, which are further described herein after. In some embodiments, paired end reads include reads of about 20 bp to 1000 bp. In some embodiments, paired end reads include reads of about 50 bp to 500 bp, about 80 bp to 150 bp, or about 100 bp.

As used herein, the terms "alignment" and "aligning" refer to the process of comparing a read to a reference sequence and thereby determining whether the reference sequence contains the read sequence. An alignment process attempts to determine if a read can be mapped to a reference sequence, but does not always result in a read aligned to the reference sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read maps to. For example, if the reference sequence is the whole human genome sequence, an alignment may indicate that a read is present on chromosome 13, and may further indicate that the read is on a particular strand and/or site of chromosome 13. In some scenarios, alignment tools are imperfect, in that a) not all valid alignments are found, and b) some obtained alignments are invalid. This happens due to various reasons, e.g., reads may contain errors, and sequenced reads may be different from the reference genome due to haplotype differences. In some applications, the alignment tools include built-in mismatch tolerance, which tolerates certain degrees of mismatch of base pairs and still allow alignment of reads to a reference sequence. This can help to identify valid alignment of reads that would otherwise be missed.

Aligned reads are one or more sequences that are identified as a match in terms of the order of their nucleic acid molecules to a known reference sequence such as a reference genome. An aligned read and its determined location on the reference sequence constitute a sequence tag. Alignment can be done manually, although it is typically implemented by a computer algorithm, as it would be impossible to align reads in a reasonable time period for implementing the methods disclosed herein. One example of an algorithm from aligning sequences is the Efficient Local Alignment of Nucleotide Data (ELAND) computer program distributed as part of the Illumina Genomics Analysis pipeline. Alternatively, a Bloom filter or similar set membership tester may be employed to align reads to reference genomes. See U.S. patent application Ser. No. 14/354,528, filed Apr. 25, 2014, which is incorporated herein by reference in its entirety. The matching of a sequence read in aligning can be a 100% sequence match or less than 100% (i.e., a non-perfect match).

The term "mapping" used herein refers to assigning a read sequence to a larger sequence, e.g., a reference genome, by alignment.

The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cell-free DNA (cfDNA) molecules. The term "polynucleotide" includes, without limitation, single- and double-stranded polynucleotides.

The term "test sample" herein refers to a sample, typically derived from a biological fluid, cell, tissue, organ, or organism, that includes a nucleic acid or a mixture of nucleic acids having at least one nucleic acid sequence that is to be screened for copy number variation and other genetic alterations, such as, but not limited to, single nucleotide polymorphism, insertions, deletions, and structural variations. In certain embodiments the sample has at least one nucleic acid sequence whose copy number is suspected of having undergone variation. Such samples include, but are not limited to sputum/oral fluid, amniotic fluid, blood, a blood fraction, or fine needle biopsy samples, urine, peritoneal fluid, pleural fluid, and the like. Although the sample is often taken from a human subject (e.g., a patient), the assays can be used for samples from any mammal, including, but not limited to dogs, cats, horses, goats, sheep, cattle, pigs, etc., as well as mixed populations, as microbial populations from the wild, or viral populations from patients. The sample may be used directly as obtained from the biological source or following a pretreatment to modify the character of the sample. For example, such pretreatment may include preparing plasma from blood, diluting viscous fluids, and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, sometimes at a concentration proportional to that in an untreated test sample (e.g., namely, a sample that is not subjected to any such pretreatment method(s)). Such "treated" or "processed" samples are still considered to be biological "test" samples with respect to the methods described herein.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "read" refers to a sequence read from a portion of a nucleic acid sample. Typically, though not necessarily, a read represents a short sequence of contiguous base pairs in the sample. The read may be represented symbolically by the base pair sequence in A, T, C, and G of the sample portion, together with a probabilistic estimate of the correctness of the base (quality score). It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 20 bp) that can be used to identify a larger sequence or region, e.g., that can be aligned and mapped to a chromosome or genomic region or gene.

The terms "site" and "alignment location" are used interchangeably to refer to a unique position (i.e. chromosome ID, chromosome position and orientation) on a reference genome. In some embodiments, a site may be a residue's, a sequence tag's, or a segment's position on a reference sequence.

As used herein, the term "reference genome" or "reference sequence" refers to any particular known genome sequence, whether partial or complete, of any organism or virus which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences. However, it is understood that "complete" is a relative concept, because even the gold-standard reference genome are expected to include gaps and errors.

In various embodiments, the reference sequence is significantly larger than the reads that are aligned to it. For example, it may be at least about 100 times larger, or at least about 1000 times larger, or at least about 10,000 times larger, or at least about $10^5$ times larger, or at least about $10^6$ times larger, or at least about $10^7$ times larger.

In one example, the reference sequence is that of a full length human genome. Such sequences may be referred to as genomic reference sequences. In another example, the reference sequence is limited to a specific human chromosome such as chromosome 13. In some embodiments, a reference Y chromosome is the Y chromosome sequence from human genome version hg19. Such sequences may be referred to as chromosome reference sequences. Other examples of reference sequences include genomes of other species, as well as chromosomes, sub-chromosomal regions (such as strands), etc., of any species.

In some embodiments, a reference sequence for alignment may have a sequence length from about 1 to about 100 times the length of a read. In such embodiments, the alignment and sequencing are considered a targeted alignment or sequencing, instead of a whole genome alignment or sequencing. In these embodiments, the reference sequence typically includes a gene sequence and/or other constrained sequence of interest.

In various embodiments, the reference sequence is a consensus sequence or other combination derived from multiple individuals. However, in certain applications, the reference sequence may be taken from a particular individual.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids, e.g., cfDNA, were naturally released by cells through naturally occurring processes such as necrosis or apoptosis. In another embodiment, a mixture of nucleic acids that is derived from two different genomes means that the nucleic acids were extracted from two different types of cells from a subject.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

As used herein the term "chromosome" refers to the heredity-bearing gene carrier of a living cell, which is derived from chromatin strands including DNA and protein components (especially histones). The conventional internationally recognized individual human genome chromosome numbering system is employed herein.

As used herein, the term "polynucleotide length" refers to the absolute number of nucleic acid molecules (nucleotides) in a sequence or in a region of a reference genome. The term "chromosome length" refers to the known length of the chromosome given in base pairs, e.g., provided in the NCBI36/hg18 assembly of the human chromosome found at |genome|.|ucsc|.|edu/cgi-bin/hgTracks?hgsid=167155613& chromInfoPage= on the World Wide Web.

The term "primer," as used herein refers to an isolated oligonucleotide that is capable of acting as a point of initiation of synthesis when placed under conditions inductive to synthesis of an extension product (e.g., the conditions include nucleotides, an inducing agent such as DNA polymerase, necessary ions and molecules, and a suitable temperature and pH). The primer may be preferably single stranded for maximum efficiency in amplification, but alternatively may be double stranded. If double stranded, the primer is first treated to separate its strands before being used to prepare extension products. The primer may be an oligodeoxyribonucleotide. The primer is sufficiently long to prime the synthesis of extension products in the presence of the inducing agent. The exact lengths of the primers will depend on many factors, including temperature, source of primer, use of the method, and the parameters used for primer design.

Introduction and Context

Next generation sequencing (NGS) technology has developed rapidly, providing new tools to advance research and science, as well as healthcare and services relying on genetic and related biological information. NGS methods are performed in a massively parallel fashion, affording increasingly high speed for determining biomolecules sequence information. However, many of the NGS methods and associated sample manipulation techniques introduce errors such that the resulting sequences have relatively high error rate, ranging from one error in a few hundred base pairs to one error in a few thousand base pairs. Such error rates are sometimes acceptable for determining inheritable genetic information such as germline mutations because such information is consistent across most somatic cells, which provide many copies of the same genome in a test sample. An error originating from reading one copy of a sequence has a minor or removable impact when many copies of the same sequence are read without error. For instance, if an erroneous read from one copy of a sequence cannot be properly aligned to a reference sequence, it may simply be discarded from analysis. Error-free reads from other copies of the same sequence may still provide sufficient information for valid analyses. Alternatively, instead of discarding the read having a base pair different from other reads from the same sequence, one can disregard the different base pair as resulting from a known or unknown source of error.

However, such error correction approaches do not work well for detecting sequences with low allele frequencies, such as sub-clonal, somatic mutations found in nucleic acids from tumor tissue, circulating tumor DNA, low-concentration fetal cfDNA in maternal plasma, drug-resistant mutations of pathogens, etc. In these examples, one DNA fragment may harbor a somatic mutation of interest at a sequence site, while many other fragments at the same sequence site do not have the mutation of interest. In such a scenario, the sequence reads or base pairs from the mutated DNA fragment might be unused or misinterpreted in conventional sequencing, thereby losing information for detecting the mutation of interest.

Due to these various sources of errors, increasing depth of sequencing alone cannot ensure detection of somatic variations with very low allele frequency (e.g., <1%). Some implementations disclosed herein provide duplex sequencing methods that effectively suppress errors in situations when signals of valid sequences of interest are low, such as samples with low allele frequencies. The methods use virtual unique molecular indices (UMIs) in conjunction with short physical unique molecular indices placed on one arm or both arms of sequencing adapters, such as the Illumina TruSeq® adapter. These implementations are based on the strategy of using physical UMIs on adapter sequences and virtual UMIs on sample DNA fragment sequences. In some implementations, alignment positions of reads are also used to suppress errors. For example, when multiple reads (or pairs of reads) share a physical UMI and align within the same interval (constrained range of positions) on the reference, the reads are expected to originate from a single DNA fragment. Physical UMIs, virtual UMIs, and alignment positions associated with reads provide "indices" that are, alone or in combination, uniquely associated with a specific double stranded DNA fragment from a sample. Using these indices, one can identify multiple reads derived from a single DNA fragment (a single molecule), which may be just one of many fragments from the same genomic site. Using the multiple reads from a single DNA molecule, error correction can be performed effectively. For example, the sequencing methodology may obtain a consensus nucleotide sequence (hereinafter referred to as "a consensus sequence") from the multiple reads derived from the same DNA fragment, which correction does not discard valid sequence information of this DNA fragment.

Adapter designs can provide physical UMIs that allow one to determine which strand of the DNA fragment the reads are derived from. Some embodiments take advantage of this to determine a first consensus sequence for reads derived from one strand of the DNA fragment, and a second consensus sequence for the complementary strand. In many embodiments, a consensus sequence includes the base pairs detected in all or a majority of reads while excluding base pairs appearing in few of the reads. Different criteria of consensus may be implemented. The process of combining reads based on UMIs or alignment locations to obtain a consensus sequence is also referred to as "collapsing" the reads. Using physical UMIs, virtual UMIs, and/or alignment locations, one can determine that reads for the first and second consensus sequences are derived from the same double stranded fragment. Therefore, in some embodiments, a third consensus sequence is determined using the first and second consensus sequences obtained for the same DNA molecule/fragment, with the third consensus sequence including base pairs common for the first and second consensus sequences while excluding those inconsistent between the two. In alternative implementations, only one consensus sequence may be directly obtained by collapsing all reads derived from both strands of the same fragment, instead of by comparing the two consensus sequences obtained from the two strands. Finally, the sequence of the fragment may be determined from the third or the only one consensus sequence, which includes base pairs that are consistent across reads derived from both strands of the fragment.

Various implementations combine reads of two strands of a DNA fragment to suppress errors. However, in some implementations, the method applies physical and virtual UMIs to single-stranded nucleic acid (e.g., DNA or RNA) fragments, and combine reads sharing the same physical and virtual UMIs to suppress errors. Various methods may be employed to capture single stranded nucleic acid fragments in a sample.

In some embodiments, the method combines different types of indices to determine the source polynucleotide on which reads are derived. For example, the method may use both physical and virtual UMIs to identify reads deriving from a single DNA molecule. By using a second form of UMI, in addition to the physical UMI, the physical UMIs may be shorter than when only physical UMIs are used to determine the source polynucleotide. This approach has minimal impact on library prep performance, and does not require extra sequencing read length.

Applications of the disclosed methods include:
Error suppression for somatic mutation detection. For example, detection of mutation with less than 0.1% allele frequency is highly critical in liquid biopsy of circulating tumor DNA.
Correct prephasing, phasing and other sequencing errors to achieve high quality long reads (e.g., 1×1000 bp)
Decrease cycle time for fixed read length, and correct increased phasing and prephasing by this method.
Use UMIs on both sides of fragment to create virtual long paired end reads. For example, stitch a 2×500 read by doing 500+50 on duplicates.

Example Workflow for Sequencing Nucleic Acid Fragments Using UMIs

FIG. 1A is a flow chart illustrating an example workflow 100 for using UMIs to sequence nucleic acid fragments. Operation 102 provides fragments of double-stranded DNA. The DNA fragments may be obtained by fragmenting genomic DNA, collecting naturally fragmented DNA (e.g., cfDNA or ctDNA), or synthesizing DNA fragments from RNA, for example. In some implementations, to synthesize DNA fragments from RNA, messenger RNA is first purified using polyA selection or depletion of ribosomal RNA, then the selected mRNA is chemically fragmented and converted into single-stranded cDNA using random hexamer priming. A complementary strand of the cDNA is generated to create a double-stranded cDNA that is ready for library construction. To obtain double stranded DNA fragments from genomic DNA (gDNA), input gDNA is fragmented, e.g., by hydrodynamic shearing, nebulization, enzymatic fragmentation, etc., to generate fragments of appropriate lengths, e.g., about 1000 bp, 800 bp, 500, or 200 bp. For instance, nebulization can break up DNA into pieces less than 800 bp in short periods of time. This process generates double-stranded DNA fragments containing 3' and/or 5' overhangs.

Figure 1B:
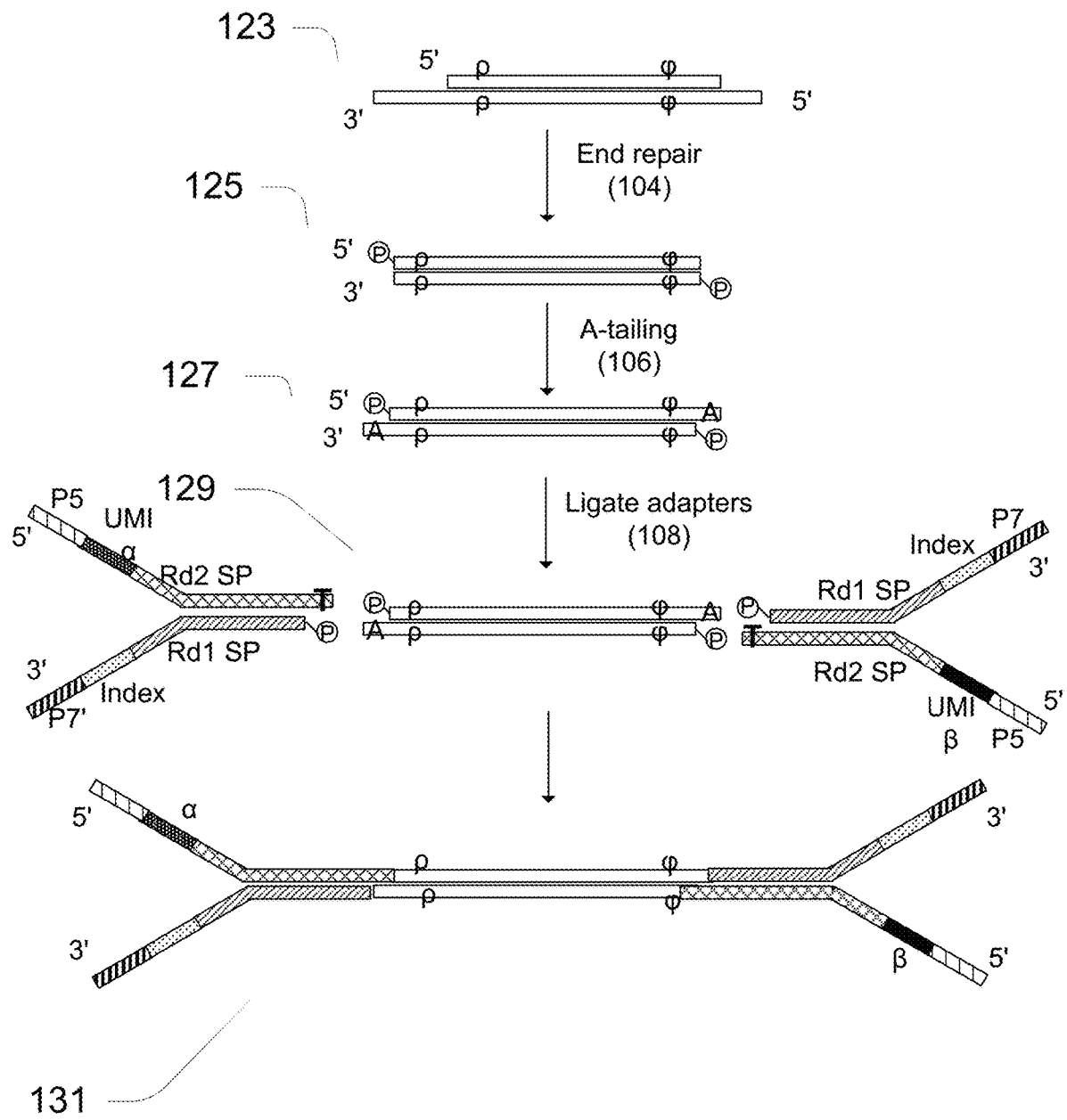
FIG. 1B shows a DNA fragment/molecule and the adapters employed in initial steps of workflow shown in FIG. 1A.

FIG. 1B shows a DNA fragment/molecule and the adapters employed in initial steps of workflow 100 in FIG. 1A. Although only one double-stranded fragment is illustrated in FIG. 1B, thousands to millions of fragments of a sample can be prepared simultaneously in the workflow. DNA fragmentation by physical methods produces heterogeneous ends, including a mixture of 3' overhangs, 5' overhangs, and blunt ends. The overhangs will be of varying lengths and ends may or may not be phosphorylated. An example of the double-stranded DNA fragments obtained from fragmenting genomic DNA of operation 102 is shown as fragment 123 in FIG. 1B.

Fragment 123 has both a 3' overhang on the left end and a 5' overhang shown on the right end, and is marked with $\rho$ and $\varphi$, indicating two sequences in the fragment that may be used as virtual UMIs, which, when used alone or combined with physical UMIs of an adapter to be ligated to the fragment, may uniquely identify the fragment. UMIs are uniquely associated with a single DNA fragment in a sample including a source polynucleotide and its complementary strand. A physical UMI is a sequence of an oligonucleotide linked to the source polynucleotide, its complementary strand, or a polynucleotide derived from the source polynucleotide. A virtual UMI is a sequence of an oligonucleotide within the source polynucleotide, its complementary strand, or a polynucleotide derived from the source polynucleotide. Within this scheme, one may also refer to the physical UMI as an extrinsic UMI, and the virtual UMI as an intrinsic UMI.

The two sequences $\rho$ and $\varphi$ actually each refer to two complementary sequences at the same genomic site, but for simplicity sake, they are indicated on only one strand in some of the double-stranded fragments shown herein. Virtual UMIs such as $\rho$ and $\varphi$ can be used at a later step of the workflow to help identify reads originating from one or both strands of the single DNA source fragment. With the reads so identified, they can be collapsed to obtain a consensus sequence.

If DNA fragments are produced by physical methods, workflow 100 proceeds to perform end repair operation 104, which produces blunt-end fragments having 5'-phosphorylated ends. In some implementations, this step converts the overhangs resulting from fragmentation into blunt ends using T4 DNA polymerase and Klenow enzyme. The 3' to 5' exonuclease activity of these enzymes removes 3' overhangs and the 5' to 3' polymerase activity fills in the 5' overhangs. In addition, T4 polynucleotide kinase in this reaction phosphorylates the 5' ends of the DNA fragments. The fragment 125 in FIG. 1B is an example of an end-repaired, blunt-end product.

After end repairing, workflow 100 proceeds to operation 106 to adenylate 3' ends of the fragments, which is also referred to as A-tailing or dA-tailing, because a single dATP is added to the 3' ends of the blunt fragments to prevent them from ligating to one another during the adapter ligation reaction. Double stranded molecule 127 of FIG. 1B shows an A-tailed fragment having blunt ends with 3'-dA overhangs and 5'-phosphate ends. A single 'T' nucleotide on the 3' end of each of the two sequencing adapters as seen in item 129 of FIG. 1B provides an overhang complementary to the 3'-dA overhang on each end of the insert for ligating the two adapters to the insert.

After adenylating 3' ends, workflow 100 proceeds to operation 108 to ligate partially double stranded adapters to both ends of the fragments. In some implementations, the adapters used in a reaction include oligonucleotides that are all different from each other, which oligonucleotides provide physical UMIs to associate sequence reads to a single source polynucleotide, which may be a single- or double-stranded DNA fragment. Because all the physical UMI oligonucleotides are different, the two UMI oligonucleotides ligated to two ends of a particular fragment are different from each other. Furthermore, the two physical UMIs for the particular fragment are different from the physical UMIs for every other fragment. In this regard, the two physical UMIs are uniquely associated with the particular fragment.

Item 129 of FIG. 1B illustrates two adapters to be ligated to the double-stranded fragment that includes two virtual UMIs $\rho$ and $\varphi$ near the ends of the fragment. These adapters are illustrated based on the sequencing adapters of the Illumina platform, as various implementations may use Illumina's NGS platform to obtain reads and detect sequence of interest. The adapter shown on the left includes the physical UMI $\alpha$ on its P5 arm, while the adapter on the right includes physical UMI $\beta$ on its P5 arm. On the strand having the 5' denatured end, from 5' to 3' direction, adapters have a P5 sequence, a physical UMI ($\alpha$ or $\beta$), and a read 2 primer sequence. On the strand having the 3' denatured end, from 3' to 5' direction, the adapters have a P7' sequence, an index sequence, and a read 1 primer sequence. The P5 and P7' oligonucleotides are complementary to the amplification primers bound to the surface of flow cells of Illumina sequencing platform. In some implementations, the index sequence provides a means to keep track of the source of a sample, thereby allowing multiplexing of multiple samples on the sequencing platform. Other designs of adapters and sequencing platforms may be used in various implementations. Adapters and sequencing technology are further described in sections that follow. The reaction depicted in FIG. 1B adds distinct sequences to the 5' and 3' ends of each strand in the genomic fragment. A ligation product 131 from the same fragment described above is illustrated in FIG. 1B. This ligation product 131 has the physical UMI $\alpha$, the virtual UMI $\rho$ and the virtual UMI $\varphi$ on its top strand, in the 5'-3' direction. The ligation product also has the physical UMI $\beta$, the virtual UMI $\varphi$ and the virtual UMI $\rho$ on its bottom strand, in the 5'-3' direction. The ligation product and the physical UMIs and virtual UMIs contained therein shown in 132 are similar to those in the top half of FIG. 3A. This disclosure embodies methods using sequencing technologies and adapters other than those provided by Illumina.

Figure 3A:
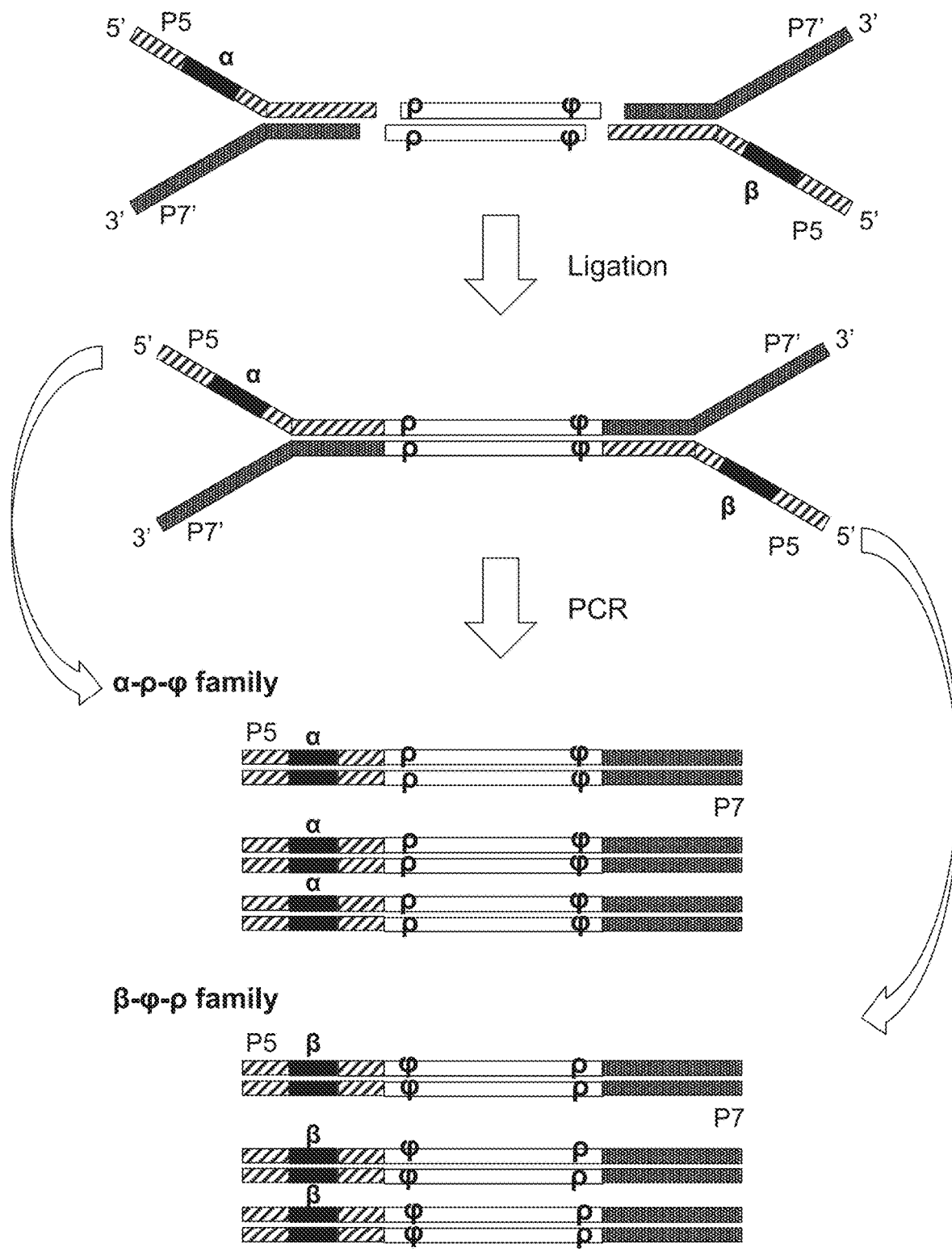
FIGS. 3A and 3B are diagrams showing the materials and reaction products of ligating adapters to double stranded fragments according to some methods disclosed herein.

In some implementations, the products of this ligation reaction are purified and/or size-selected by agarose gel electrophoresis or magnetic beads. Size-selected DNA is then PCR amplified to enrich for fragments that have adapters on both ends. See block 110. The bottom half of FIG. 3A illustrates that both strands of ligation product undergo PCR amplification, yielding two families of fragments having different physical UMIs ($\alpha$ and $\beta$). The two families each have only one physical UMI. The two families both have virtual UMIs $\rho$ and $\varphi$, but the orders of the virtual UMIs with reference to physical UMIs are different: $\alpha$-$\rho$-$\varphi$ versus $\beta$-$\varphi$-$\rho$. Some implementations purify PCR products and select a size-range of templates appropriate for subsequent cluster generation.

Workflow 100 then proceeds to cluster amplify PCR products on an Illumina platform. See operation 112. By clustering of the PCR products, libraries can be pooled for multiplexing, e.g., with up to 12 samples per lane, using different index sequences on the adapters to keep track of different samples.

After cluster amplification, sequencing reads can be obtained through sequencing by synthesis on the Illumina platform. See operation 114. Although the adapters and the sequencing process described here are based on the Illumina platform, others sequencing technologies, especially NGS methods may be used instead of or in addition to the Illumina platform.

The sequencing reads derived from the segment shown in FIGS. 1B and 3A are also expected to include UMIs $\alpha$-$\rho$-$\varphi$ or $\beta$-$\varphi$-$\rho$. The workflow 100 uses this feature to collapse reads having the same physical UMI(s) and/or the same virtual UMI(s) into one or more groups, thereby obtaining one or more consensus sequences. See operation 116. A consensus sequence includes nucleotide bases that are consistent or meet a consensus criterion across reads in a collapsed group. As shown in operation 116, physical UMIs, virtual UMIs, and position information may be combined in various ways to collapse reads to obtain consensus sequences for determining the sequence of a fragment or at least a portion thereof. In some implementations, physical UMIs are combined with virtual UMIs to collapse reads. In other implementations, physical UMIs and read positions are combined to collapse reads. Read position information may be obtained by various techniques using different position measurements, e.g., genomic coordinates of the reads, positions on a reference sequence, or chromosomal positions. In further implementations, physical UMIs, virtual UMIs, and read positions are combined to collapse reads.

Finally, workflow 100 uses the one or more consensus sequences to determine the sequence of the nucleic acid fragment from the sample. See operation 118. This may involve determining the nucleic acid fragment's sequence as the third consensus sequence or the single consensus sequence described above.

In a particular implementation that includes operations similar to operations 108-119, a method for sequencing nucleic acid molecules from a sample using nonrandom UMIs involves the following: (a) applying adapters to both ends of DNA fragments in the sample, wherein the adapters each include a double-stranded hybridized region, a single-stranded 5' arm, a single-stranded 3' arm, and a nonrandom UMI, thereby obtaining DNA-adapter products; (b) amplifying the DNA-adapter products to obtain a plurality of amplified polynucleotides; (c) sequencing the plurality of amplified polynucleotides, thereby obtaining a plurality of reads associated with a plurality of nonrandom UMIs; (d) from the plurality of reads, identifying reads sharing a common nonrandom UMI and a common read position; and (e) from the identified reads, determining the sequence of at least a portion of a DNA fragment.

In various implementations, obtained sequence reads are associated with physical UMIs (e.g., random or nonrandom UMIs). In such implementations, a UMI is either part of a read sequence or part of a different read's sequence, where the different read and the read in question are known to come from the same fragment; e.g., by pair end reading or location specific information. Such as virtual UMIs.

In some implementations, the sequence reads are paired-end reads. Each read either includes a nonrandom UMI or is associated with a nonrandom UMI through a paired-end read. In some implementations, the read lengths are shorter than the DNA fragments or shorter than one half of the fragments' length. In such cases, the complete sequence of the whole fragment is sometimes not determined. Rather, the two ends of the fragment are determined. For example, a DNA fragment may be 500 bp long, from which two 100 bp paired-end reads can be derived. In this example, the 100 bases at each end of the fragment can be determined, and the 300 bp in the middle of the fragment may not be determined without using information of other reads. In some implementations, if the two pair-end reads are long enough to overlap, the complete sequence of the whole fragment may be determined from the two reads. For instance, see the example described in association with FIG. 5.

In some implementations, every nonrandom UMI differs from every other nonrandom UMI by at least two nucleotides at corresponding sequence positions of the nonrandom UMIs. In various implementations, the plurality of nonrandom UMIs includes no more than about 10,000, 1,000, or 100 unique nonrandom UMIs. In some implementations, the plurality of nonrandom UMIs includes 96 unique nonrandom UMIs.

In some implementations, an adaptor has a duplex nonrandom UMI in the double stranded region of the adaptor, and each read includes a first nonrandom UMI on one end and a second nonrandom UMI on the other end.

Adapters and UMIs

Adapters

Figure 2A:
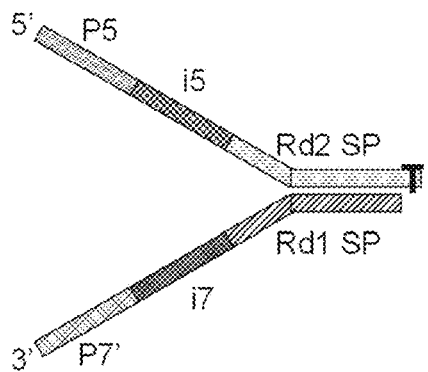
FIG. 2A schematically illustrates five different adapter designs that may be adopted in the various implementations.
Figure 2A:
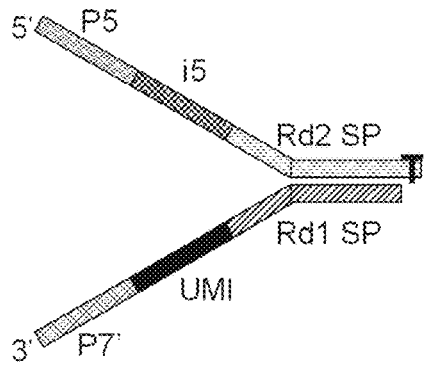
Figure 2A:
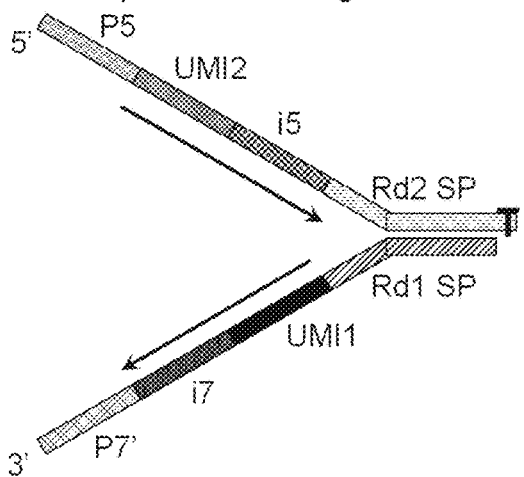
Figure 2A:
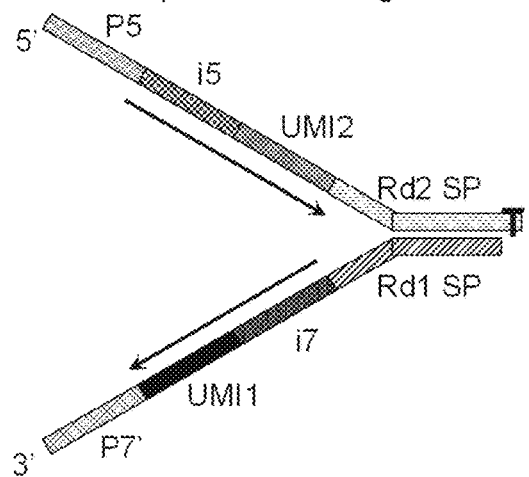
Figure 2A:
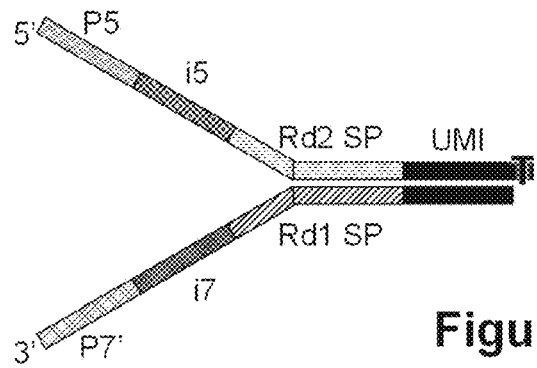
Figure 2A:
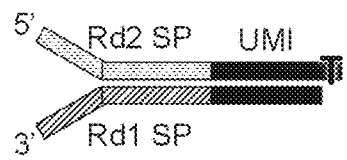

In addition to the adapter design described in the example workflow above, other designs of adapters may be used in various implementations of the methods and systems disclosed herein. FIG. 2A schematically illustrates five different designs of adapter with UMI(s) that may be adopted in the various implementations.

FIG. 2A(i) shows a standard Illumina TruSeq® dual index adapter. The adapter is partially double-stranded and is formed by annealing two oligonucleotides corresponding to the two strands. The two strands have a number of complementary base pairs (e.g., 12-17 bp) that allow the two oligonucleotides to anneal at the end to be ligated with a dsDNA fragment. A dsDNA fragment to be ligated on both ends for pair-end reads is also referred to as an insert. Other base pairs are not complementary on the two strands, resulting in a fork-shaped adapter having two floppy overhangs. In the example of FIG. 2A(i), the complementary base pairs are part of read 2 primer sequence and read 1 primer sequence. Downstream to the read 2 primer sequence is a single nucleotide 3'-T overhang, which provides an overhang complementary to the single nucleotide 3'-A overhang of a dsDNA fragment to be sequenced, which can facilitate hybridization of the two overhangs. The read 1 primer sequence is at the 5' end of the complementary strand, to which a phosphate group is attached. The phosphate group facilitates ligating the 5' end of the read 1 primer sequence to the 3'-A overhang of the DNA fragment. On the strand having the 5' floppy overhang (the top strand), from 5' to 3' direction, the adapter has a P5 sequence, i5 index sequence, and the read 2 primer sequence. On the strand having the 3' floppy overhang, from 3' to 5' direction, the adapter has a P7' sequence, an i7 index sequence, and the read 1 primer sequence. The P5 and P7' oligonucleotides are complementary to the amplification primers bound to the surface of flow cells of an Illumina sequencing platform. In some implementations, the index sequences provide means to keep track of the source of a sample, thereby allowing multiplexing of multiple samples on the sequencing platform.

FIG. 2A(ii) shows an adapter having a single physical UMI replacing the i7 index region of the standard dual index adapter shown in FIG. 2A(i). This design of the adapter mirrors that shown in the example workflow described above in association with FIG. 1B. In certain embodiments, the physical UMIs α and β are designed to be on only the 5' arm of the double-stranded adapters, resulting in ligation products that have only one physical UMI on each strand. In comparison, physical UMIs incorporated into both strands of the adapters result in ligation products that have two physical UMIs on each strand, doubling the time and cost to sequence the physical UMIs. However, this disclosure embodies methods employing physical UMIs on both strands of the adapters as depicted in FIGS. 2A(iii)-2A(vi), which provide additional information that may be utilized for collapsing different reads to obtain consensus sequences.

In some implementations, the physical UMIs in the adapters include random UMIs. In some implementations, the physical UMIs in the adapters include nonrandom UMIs.

FIG. 2A(iii) shows an adapter having two physical UMIs added to the standard dual index adapter. The physical UMIs shown here may be random UMIs or nonrandom UMIs. The first physical UMI is upstream to the i7 index sequence, and the second physical UMI is upstream to the i5 index sequence. FIG. 2A(iv) shows an adapter also having two physical UMIs added to the standard dual index adapter. The first physical UMI is downstream to the i7 index sequence, and the second physical UMI is downstream to the i5 index sequence. Similarly, the two physical UMIs may be random UMIs or nonrandom UMIs.

An adapter having two physical UMIs on the two arms of the single stranded region, such as those shown in 2A(iii) and 2A(iv), may link two strands of a double stranded DNA fragment, if a priori or a posteriori information associating the two un-complementary physical UMIs is known. For instance, a researcher may know the sequences of UMI 1 and UMI 2 before integrating them to the same adapter in the designed shown in FIG. 2A(iv). This association information may be used to infer that reads having UMI 1 and UMI 2 derive from two strands of the DNA fragment to which the adapter was ligated. Therefore, one may collapse not only reads having the same physical UMI, but also reads having either of the two un-complementary physical UMIs. Interestingly, and as discussed below, a phenomenon referred to as "UMI jumping" may complicate the inference of association among physical UMIs on single-stranded regions of adapters.

The two physical UMIs on the two strands of the adapters in FIG. 2A(iii) and FIG. 2A(iv) are neither located at the same site nor complementary to each other. However, this disclosure embodies methods employing physical UMIs that are at the same site on two strands of the adapter and/or complementary to each other. FIG. 2A(v) shows a duplex adapter in which the two physical UMIs are complementary on a double stranded region at or near the end of the adapter. In some implementations, a physical UMI near the end of the adapter may be 1 nucleotide, 2 nucleotides, 3 nucleotides, 4 nucleotides, 5 nucleotides, or about 10 nucleotides from an end of the double-stranded region of the adapter, the end being opposite from the forked region of the adapter. The two physical UMIs may be random UMIs or nonrandom UMIs. FIG. 2A(vi) shows an adapter similar to but shorter than that of FIG. 2A(v), but it does not include the index sequences or the P5 and P7' sequences complementary to flow cell surface amplification primers. Similarly, the two physical UMIs may be random UMIs or nonrandom UMIs.

Compared to adapters having one or more single-stranded physical UMIs on single-stranded arms, adapters having a double-stranded physical UMI on the double-stranded region can provide a direct link between two strands of a double stranded DNA fragment to which the adapter is ligated, as shown in FIG. 2A(v) and FIG. 2A(vi). Since the two strands of a double-stranded physical UMI are complementary to each other, the association between the two strands of the double-stranded UMI is inherently reflected by the complementary sequences, and can be established without requiring either a priori or a posteriori information. This information may be used to infer that reads having the two complementary sequences of a double-stranded physical UMI of an adapter are derived from the same DNA fragment to which the adapter was ligated, but the two complementary sequences of the physical UMI are ligated to the 3' end on one strand and the 5' end on the other strand of the DNA fragment. Therefore, one may collapse not only reads having the same order of two physical UMI sequences on two ends, but also reads having the reverse order of two complementary sequences on two ends.

In some embodiments, it can be advantageous to employ relatively short physical UMIs because short physical UMIs are easier to incorporate into adapters. Furthermore, shorter physical UMIs are faster and easier to sequence in the amplified fragments. However, as physical UMIs become very short, the total number of different physical UMIs can become less than the number of adapter molecules required for sample processing. In order to provide enough adapters, the same UMI would have to be repeated in two or more adapter molecules. In such a scenario, adapters having the same physical UMIs may be ligated to multiple source DNA molecules. However, these short physical UMIs may provide enough information, when combined with other information such as virtual UMIs and/or alignment locations of reads, to uniquely identify reads as being derived from a particular source polynucleotide or DNA fragment in a sample. This is so because even though the same physical UMI may be ligated to two different fragments, it is unlikely the two different fragments would also happen to have the same alignment locations, or matching subsequences serving as virtual UMIs. So if two reads have the same short physical UMI and the same alignment location (or the same virtual UMI), the two reads are likely derived from the same DNA fragment.

Furthermore, in some implementations, read collapsing is based on two physical UMIs on the two ends of an insert. In such implementations, two very short physical UMIs (e.g., 4 bp) are combined to determine the source of DNA fragments, the combined length of the two physical UMIs providing sufficient information for distinguishing among different fragments.

In various implementations, physical UMIs are about 12 base pairs or shorter, about 11 base pairs or shorter, about 10 base pairs or shorter, about 9 base pairs or shorter, about 8 base pairs or shorter, about 7 base pairs or shorter, about 6 base pairs or shorter, about 5 base pairs or shorter, about 4 base pairs or shorter, or about 3 base pairs or shorter. In some implementations where the physical UMIs are nonrandom UMIs, the UMIs are about 12 base pairs or shorter, about 11 base pairs or shorter, about 10 base pairs or shorter, about 9 base pairs or shorter, about 8 base pairs or shorter, about 7 base pairs or shorter, or about 6 base pairs.

UMI jumping may affect the inference of association among physical UMIs on one arm or both arms of adapters, such as in the adapters of FIGS. 2A(ii)-(iv). It has been observed that when applying these adapters to DNA fragments, amplification products may include a larger number of fragments having unique physical UMIs than the actual number of fragments in the sample.

Furthermore, when adapters having physical UMIs on both arms are applied, amplified fragments having a common physical UMI on one end are supposed to have another common physical UMI on another end. However, sometimes this is not the case. For instance, in the reaction product of one amplification reaction, some fragments may have a first physical UMI and a second physical UMI on their two ends; other fragments may have the second physical UMI and a third physical UMI; yet other fragments may have the first physical UMI and the third physical UMI; still further fragments may have the third physical UMI and a fourth physical UMI, and so on. In this example, the source fragment(s) for these amplified fragments may be difficult to ascertain. Apparently, during the amplification process, the physical UMI may have been "swapped out" by another physical UMI.

One possible approach to addressing this UMI jumping problem considers only fragments sharing both UMIs as deriving from the same source molecule, while fragments sharing only one UMI will be excluded from analysis. However, some of these fragments sharing only one physical UMI may indeed derive from the same molecule as those sharing both physical UMIs. By excluding the fragments sharing just one physical UMI from consideration, useful information may be lost. Another possible approach considers any fragments having one common physical UMI as deriving from the same source molecule. But this approach does not allow combining two physical UMIs on two ends of the fragments for downstream analysis. Furthermore, under either approach, for the example above, fragments sharing the first and second physical UMIs would not be considered to derive from the same source molecule as fragments sharing the third and fourth physical UMIs. This may or may not be true. A third approach may address the UMI jumping problem by using adapters with physical UMIs on both strands of the single-stranded region, such as the adapters in FIGS. 2A(v)-(vi). The third approach is further explained below following a description of a hypothetical mechanism underlying UMI jumping.

Figure 2B:
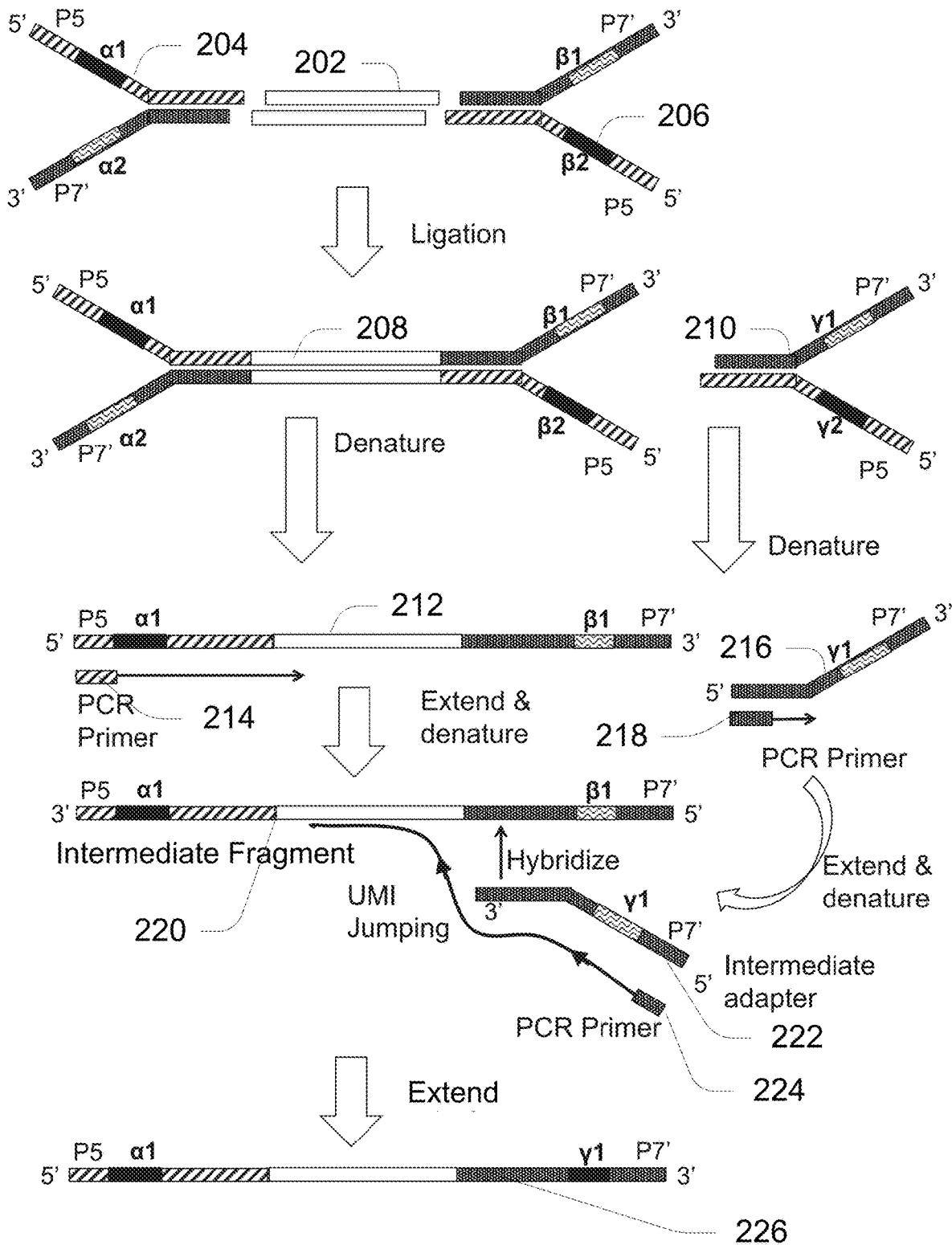
FIG. 2B illustrates a hypothetical process in which UMI jumping occurs in a PCR reaction involving adapters having two physical UMIs on two arms.

FIG. 2B illustrates a hypothetical process in which UMI jumping occurs in a PCR reaction involving adapters having two physical UMIs on two arms. The two physical UMIs may be random UMIs or nonrandom UMIs. The actual underlying mechanism of UMI jumping and the hypothetical process described here do not affect the utility of the adapters and methods disclosed herein. The PCR reaction starts by providing at least one double stranded source DNA fragment 202 and adapters 204 and 206. Adapters 204 and 206 are similar to the adapters illustrated in FIG. 2A(iii)-(iv). Adapter 204 has a P5 adapter sequence and an α1 physical UMI on its 5' arm. Adapter 204 also has a P7' adapter sequence and an α2 physical UMI on its 3' arm. Adapter 206 has a P5 adapter sequence and a β2 physical UMI on its 5' arm, and a P7' adapter sequence and a β1 physical UMI on its 3' arm. The process proceeds by ligating adapter 204 and adapter 206 to fragment 202, obtaining ligation product 208. The process proceeds by denaturing ligation product 208, resulting in a single stranded, denatured fragment 212. Meanwhile, a reaction mixture often includes residual adapters at this stage. Because even if the process has already involved removing overabundant adapters such as using Solid Phase Reversible Immobilization (SPRI) beads, some adapters are still left over in the reaction mixture. Such a leftover adapter is illustrated as adapter 210, which is similar to adapter 206, except that adapter 210 has physical UMIs γ1 and γ2 on its 3' and 7' arms, respectively. The denaturing condition producing the denatured fragment 212 also produces a denatured adapter oligonucleotide 216, which has physical UMI γ1 near its P7' adapter sequence.

The PCR reaction involves priming the denatured fragment 212 with a PCR primer 214 and extending the primer 214, thereby forming a double-stranded fragment that is then denatured to form a single-stranded, intermediate fragment 220 complementary to fragment 212. The PCR process also primes the denatured oligonucleotide 216 with a PCR primer 218 and extending the primer 218, thereby forming a double-stranded fragment that is then denatured to form a single-stranded, intermediate adapter oligonucleotide 222 complementary to fragment 212. Before the next cycle of PCR amplification, intermediate adapter oligonucleotides 222 hybridize to intermediate fragment 220 near the P7' end and downstream of the physical UMI β1. The hybridized region corresponds to the single-stranded regions of adapter 206 and adapter 210, because these single-stranded regions share the same sequence.

The hybridized product of intermediate fragment 220 and intermediate adapter oligonucleotide 222 provides a template that can then be primed by a P7' PCR primer 224 at the 5' end of oligonucleotide 222 and extended. During extension, the extension template switches to intermediate fragment 220 when intermediate adapter oligonucleotide 222 ends. The template switching provides a possible mechanism for UMI jumping. After extension and denaturing, a single-stranded fragment 226 is produced, which is otherwise complementary to intermediate fragment 220 but it has the physical UMI γ1 instead of the physical UMI β1 in intermediate fragment 220. Similarly, single-stranded fragment 226 is the same as fragment 212 except that it has the physical UMI γ1 instead of the physical UMI β1.

In some implementations of the disclosure, using adapters having physical UMIs on both strands of the double-stranded region of the adapters, such as the adapters in FIGS. 2A(v)-(vi), may prevent or reduce UMI jumping. This may be due to the fact that the physical UMIs on one adapter at the double-stranded region are different from physical UMIs on all other adapters. This helps to reduce the complementarity between intermediate adapter oligonucleotides and intermediate fragments, thereby avoiding hybridization such as that shown for intermediate oligonucleotide 222 and intermediate fragment 220, thereby reducing or preventing UMI jumping.

Random Physical UMIs and Nonrandom Physical UMIs

In some implementations of the adapters described above, the physical UMIs in the adapters include random UMIs. In some implementations, each random UMI is different from every other random UMI applied to DNA fragments. In other words, the random UMIs are randomly selected without replacement from a set of UMIs including all possible different UMIs given the sequence length(s). In other implementations, the random UMIs are randomly selected with replacement. In these implementations, two adapters may have the same UMI due to random chance.

In some implementations, the physical UMIs in the adapters include nonrandom UMIs. In some implementations, multiple adapters include the same nonrandom UMI sequence. For instance, a set of 96 different nonrandom UMIs may be applied to 100,000 distinct molecules/fragments from a sample. In some implementations, each nonrandom UMI of the set differs from every other UMI of the set by two nucleotides. In other words, each nonrandom UMI requires that it at least two of its nucleotides be replaced before matching the sequence of any other non-random UMI used in the sequencing. In other implementations, each nonrandom UMI of the set differs from every other UMI of the set by three or more nucleotides.

Figure 2C:
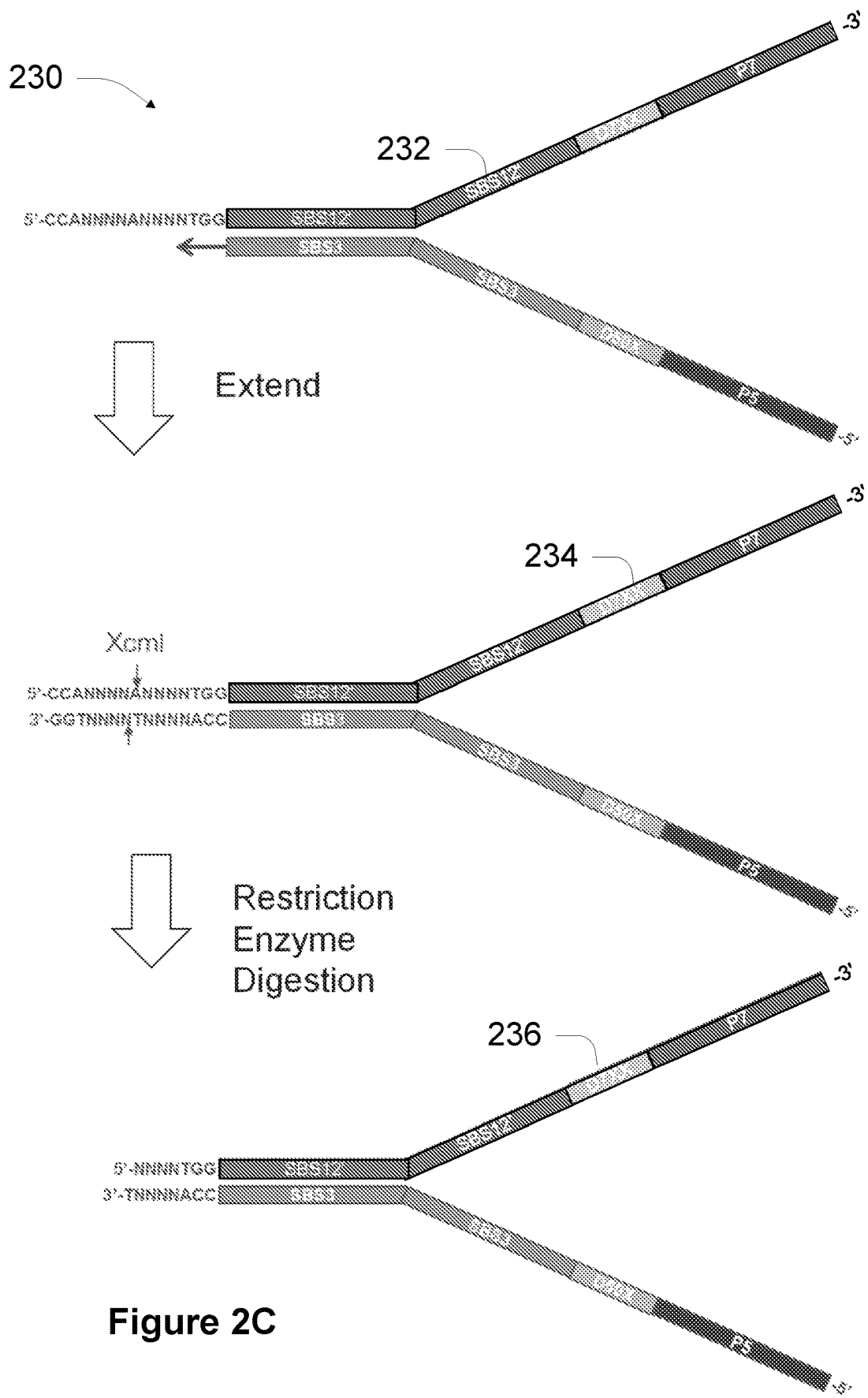
FIG. 2C shows a process for making adapters having UMIs on both strands of the adapters in the double-stranded region, which process uses a 15-mer sequence (SEQ ID NO:1) as a recognition sequence for restriction enzyme Xcm1.

FIG. 2C shows a process for making adapters having random UMIs on both strands of the adapters in the double-stranded region, where two adapters on two strands are complimentary to each other. The process starts by providing a sequencing adapter 230 having a hybridized, double-stranded region and two single-stranded arms. The resulting adapter is similar to that shown in FIG. 2A(v). In the example illustrated here, the D7XX sequence corresponds to the i7 index sequence in FIG. 2A(v); the SBS12' sequence corresponds to the read 1 primer sequence in FIG. 2A(v); the D50X corresponds to i5 index sequence in FIG. 2A(v); and the SBS3 corresponds to the read 2 primer sequence in FIG. 2A(v). Sequencing adapter 232 includes a 15-mer over-hang CCANNNNANNNNTGG (SEQ ID NO:1) at the end of the double-stranded hybridized region upstream of the SBS12' read primer sequence. The letter N represents random nucleotides, of which the four between A and TGG will be used to provides a physical UMI at the 5' end of the SBS12' strand. The 15-mer over-hang can be recognized by restriction enzyme Xcm1, because Xcm1 recognizes 15-mers having CCA at the 5' and TGG at the 3' end. Process 230 then proceeds to extend the 3' end of the SPS3 strand using the 15-mer as an extension template, thereby producing an extension product 234. Extension product 234 has a tyrosine at the mid-point of the 15-mer on the SBS3 strand corresponding to the adenosine on the SBS12' strand. The tyrosine residue will become the residue at the 3' end of the double-stranded region of the adapter end product of process 230. The tyrosine residue can hybridize to the adenosine residue at the 3' A-tail of an insert.

Process 230 proceeds by applying restriction enzyme Xcm1 to digest the newly extended end of extension product 234. Xcm1 is a restriction endonuclease that recognizes 15-mers having CCA at the 5' and TGG at the 3' end, and its phosphodiesterase activity digests a nucleic acid strand by severing the phosphodiester bond between the $8^{th}$ and $9^{th}$ nucleotides counting from the CAA 5' end. This digestion mechanism digests the double stranded end of extension product 234 immediately downstream of the adenosine residue on the SBS12' strand and downstream of the tyrosine residue on the SBS3 strand. The digestion results in an adapter 236 that has four random nucleotides the 5' end of its double-stranded region upstream of the SBS12' sequence. Adapter 236 also has a tyrosine overhang and four random nucleotides at the 3' end of its double-stranded region downstream of the SB S3 sequence. The four random nucleotides on each strand provide a physical UMI, and the two physical UMIs on the two strands are complementary to each other.

Figure 2D:
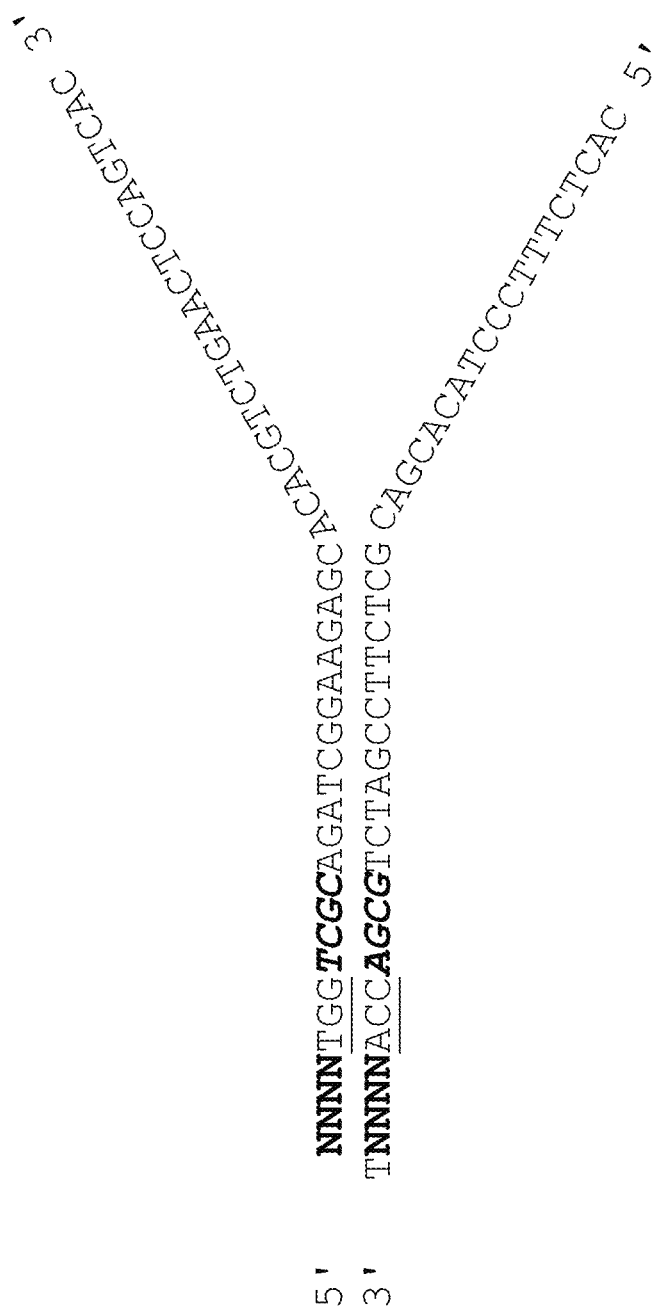
FIG. 2D shows a diagram of an adapter having a P7 arm top strand (SEQ ID NO:2) and a P5 arm bottom strand (SEQ ID NO:3).

FIG. 2D shows a diagram of an adapter having a SBS13 arm top strand (SEQ ID NO:2) and a SBS3 arm bottom strand (SEQ ID NO:3), illustrating the nucleotides in the adapter. The adapter is similar to adapter 236 in FIG. 2C, but it has four base pairs between the recognition site of Xcm1 and the read sequences of the adapter. Also, the adapter shown in FIG. 2D is a shortened version of adapter 236 that eliminates the P7/P5 and index sequence in the adapter, which increases adapter stability. On the top strand of the adapter (SEQ ID NO:2) in the double-stranded region, starting from the 5' end, the adapter has four random nucleotides for a physical UMI, followed by TGG as the recognition site for restriction enzyme Xcm1, followed by TCGC upstream of the read sequence. The TCGC nucleotides are incorporated to provide stability to the adapter. They are optional in some implementations.

Nucleotides may be added to provide stability in adapter production, sample preparation and processing. It has been observed that the annealing efficiency of the top and bottom oligos to create the initial adapter template is enhanced upon providing additional TCGC bases even in room temperature. Because the Klenow extension and Xcm1 digestion during adapter production is performed at higher temperatures (30° C. and 37° C., respectively), the additional of TCGC may enhance adapter stability. It is possible to use different sequences or varying nucleotide lengths besides TCGC to improve adapter stability.

In some implementations, additional sequences other than stabilizing sequences may be incorporated into the adapter for other purposes without affecting the adapter's function to provide unique indices to DNA fragments. The bottom strand of the adapter (SEQ ID NO:3) in the double-stranded region is complementary to the top strand, except that it includes a T overhang at the 3' end. The four random nucleotides at the bottom strand provide a second physical UMI.

Random UMIs such as the ones illustrated in FIGS. 2C and 2D provide a larger number of unique UMIs than nonrandom UMIs of the same sequence length. In other words, random UMIs are more likely to be unique than nonrandom UMIs. However, in some implementations, nonrandom UMIs may be easier to manufacture or have higher conversion efficiency. When nonrandom UMIs are combined with other information such as sequence position and virtual UMI, they can provide an efficient mechanism to index the source molecules of DNA fragments.

In various implementations, nonrandom UMIs are identified taking into consideration's various factors, including but not limited to, means for detecting errors within the UMI sequences, conversion efficiency, assay compatibility, GC content, homopolymers, and manufacturing considerations.

Figure 2E:
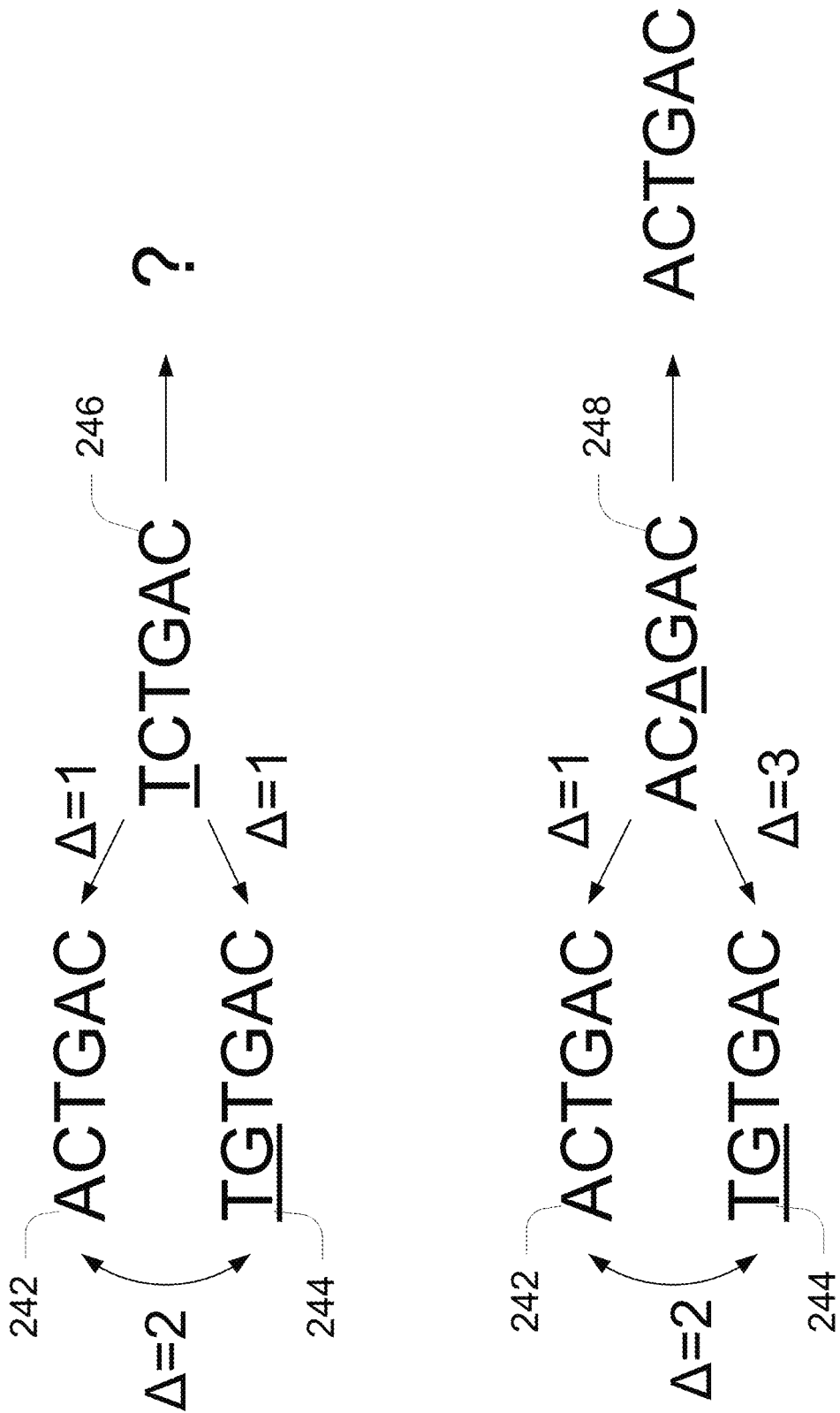
FIG. 2E schematically illustrates a nonrandom UMI design that provides a mechanism for detecting errors that occur in the UMI sequence during a sequencing process.

For instance, nonrandom UMIs may be designed to provide a mechanism for facilitating error detection. FIG. 2E schematically illustrates a nonrandom UMI design that provides a mechanism for detecting errors that occur in the UMI sequence during a sequencing process. According to this design, each of the nonrandom UMIs has six nucleotides and differs from every other UMI by at least two nucleotides. As illustrated in FIG. 2E, the nonrandom UMI 244 differs from the nonrandom UMI 242 in the first two nucleotides from the left, as shown by the underlined nucleotides T and G in UMI 244 and nucleotides A and C in UMI 242. UMI 246 is a sequence identified as part of a read, and it is different from all other UMIs of adapters provided in the process. Since the UMI sequence in a read is supposedly derived from a UMI in an adapter, an error likely has occurred during the sequencing process, such as during amplification or sequencing. UMI 242 and UMI 244 are illustrated as the two UMIs most similar to the UMI 246 in the read. It can be seen that UMI 246 differs from UMI 242 by one nucleotide in the first nucleotide from the left, which is T instead of A. Moreover, UMI 246 also differs from UMI 244 by one nucleotide, albeit in the second nucleotide from the left, which is C instead of G. Because UMI 246 in the read differs from both UMI 242 and UMI 244 by one nucleotide, from the information illustrated, it cannot be determined whether UMI 246 is derived from UMI 242 or UMI 244. However, in many other scenarios, the UMI errors in the reads are not equally different from the two most similar UMIs. As shown in the example for UMI 248, UMI 242 and UMI 244 are also the two UMIs most similar to the UMI 248. It can be seen that UMI 248 differs from UMI 242 by one nucleotide in the third nucleotide from the left, which is A instead of T. In contrast, UMI 248 differs from UMI 244 by three nucleotides. Therefore, it cannot be determined UMI 248 is derived from UMI 242 instead of UMI 244, and an error likely occurred in the third nucleotide from the left.

Virtual UMIs

Turning to virtual UMI, those Virtual UMIs that are defined at, or with respect to, the end positions of source DNA molecules can uniquely or nearly uniquely define individual source DNA molecules when the locations of the end positions are generally random as with some fragmentation procedures and with naturally occurring cfDNA. When the sample contains relatively few source DNA molecules, the virtual UMIs can themselves uniquely identify individual source DNA molecules. Using a combination of two virtual UMIs, each associated with a different end of a source DNA molecule, increases the likelihood that virtual UMIs alone can uniquely identify source DNA molecules. Of course, even in situations where one or two virtual UMIs cannot alone uniquely identify source DNA molecules, the combination of such virtual UMIs with one or more physical UMIs may succeed.

If two reads are derived from the same DNA fragment, two subsequences having the same base pairs will also have the same relative location in the reads. On the contrary, if two reads are derived from two different DNA fragments, it is unlikely that two subsequences having the same base pairs have the exact same relative location in the reads. Therefore, if two or more subsequences from two or more reads have the same base pairs and the same relative location on the two or more reads, it can be inferred that the two or more reads are derived from the same fragment.

In some implementations, subsequences at or near the ends of a DNA fragment are used as virtual UMIs. This design choice has some practical advantages. First, the relative locations of these subsequences on the reads are easily ascertained, as they are at or near the beginning of the reads and the system need not use an offset to find the virtual UMI. Furthermore, since the base pairs at the ends of the fragments are first sequenced, those base pairs are available even if the reads are relatively short. Moreover, base pairs determined earlier in a long read have lower sequencing error rate than those determined later. In other implementations, however, subsequences located away from the ends of the reads can be used as virtual UMIs, but their relative positions on the reads may need to be ascertained to infer that the reads are obtained from the same fragment.

One or more subsequences in a read may be used as virtual UMIs. In some implementations, two subsequences, each tracked from a different end of the source DNA molecule, are used as virtual UMIs. In various implementations, virtual UMIs are about 24 base pairs or shorter, about 20 base pairs or shorter, about 15 base pairs or shorter, about 10 base pairs or shorter, about 9 base pairs or shorter, about 8 base pairs or shorter, about 7 base pairs or shorter, or about 6 base pairs or shorter. In some implementations, virtual UMIs are about 6 to 10 base pairs. In other implementations, virtual UMIs are about 6 to 24 base pairs.

Collapsing Reads and Obtaining Consensus Sequences

In various implementations using UMIs, multiple sequence reads having the same UMI(s) are collapsed to obtain one or more consensus sequences, which are then used to determine the sequence of a source DNA molecule. Multiple distinct reads may be generated from distinct instances of the same source DNA molecule, and these reads may be compared to produce a consensus sequence as described herein. The instances may be generated by amplifying a source DNA molecule prior to sequencing, such that distinct sequencing operations are performed on distinct amplification products, each sharing the source DNA molecule's sequence. Of course, amplification may introduce errors such that the sequences of the distinct amplification products have differences. In the context some sequencing technologies such as Illumina's sequencing-by-synthesis, a source DNA molecule or an amplification product thereof forms a cluster of DNA molecules linked to a region of a flow cell. The molecules of the cluster collectively provide a read. Typically, at least two reads are required to provide a consensus sequence. Sequencing depths of 100, 1000, and 10,000 are examples of sequencing depths useful in the disclosed embodiments for creating consensus reads for low allele frequencies (e.g., about 1% or less).

In some implementations, nucleotides that are consistent across 100% of the reads sharing a UMI or combination of UMIs are included in the consensus sequence. In other implementations, consensus criterion can be lower than 100%. For instance, a 90% consensus criterion may be used, which means that base pairs that exist in 90% or more of the reads in the group are included in the consensus sequence. In various implementations, the consensus criterion may be set at about 30%, about 40%, about 50%, about 60%, about 70%, about 80%, about 90%, about 95%, or about 100%.

Collapsing by Physical UMIs and Virtual UMIs

Multiple techniques may be used to collapse reads that include multiple UMIs. In some implementations, reads sharing a common physical UMI may be collapsed to obtain a consensus sequence. In some implementations, if the common physical UMI is a random UMI, the random UMI may be unique enough to identify a particular source molecule of a DNA fragment in a sample. In other implementations, if the common physical UMI is a nonrandom UMI, the UMI may not be unique enough by itself to identify a particular source molecule. In either case, a physical UMI may be combined with a virtual UMI to provide an index of the source molecule.

In the example workflow described above and depicted in FIGS. 1B, 3A, and 4, some reads include $\alpha$-$\rho$-$\varphi$ UMIs, while others include $\beta$-$\gamma$-$\rho$ UMIs. The physical UMI $\alpha$ produces reads having $\alpha$. If all adapters used in a workflow have different physical UMIs (e.g., different random UMIs), all reads having a at the adapter region are likely derived from the same strand of the DNA fragment. Similarly the physical UMI $\beta$ produces reads having $\beta$, all of which are derived from the same complementary strand of the DNA fragment. It is therefore useful to collapse all reads including a to obtain one consensus sequence, and to collapse all reads including $\beta$ to obtain another consensus sequence. This is illustrated as the first level collapsing in FIGS. 4B-4C. Because all reads in a group are derived from the same source polynucleotide in a sample, base pairs included in the consensus sequence likely reflect the true sequence of the source polynucleotide, while a base pair excluded from the consensus sequence likely reflects a variation or error introduced in the workflow.

In addition, the virtual UMIs $\rho$ and $\varphi$ can provide information to determine that reads including one or both virtual UMIs are derived from the same source DNA fragment. Because virtual UMIs $\rho$ and $\varphi$ are internal to the source DNA fragments, the exploitation of the virtual UMIs do not add overhead to preparation or sequencing in practice. After obtaining the sequences of the physical UMIs from reads, one or more sub-sequences in the reads may be determined as virtual UMIs. If the virtual UMIs include sufficient base pairs and have the same relative location on reads, they may uniquely identify the reads as having been derived from the source DNA fragment. Therefore, reads having one or both virtual UMIs $\rho$ and $\varphi$ may be collapsed to obtain a consensus sequence. The combination of virtual UMIs and physical UMIs can provide information to guide a second-level collapsing when only one physical UMI is assigned to a first level consensus sequence of each strand, such as shown in FIG. 3A and FIGS. 4A-4C. However, in some implementations, this second level collapsing using virtual UMIs may be difficult if there are over-abundant input DNA molecules or fragmentation is not randomized.

Figure 3B:
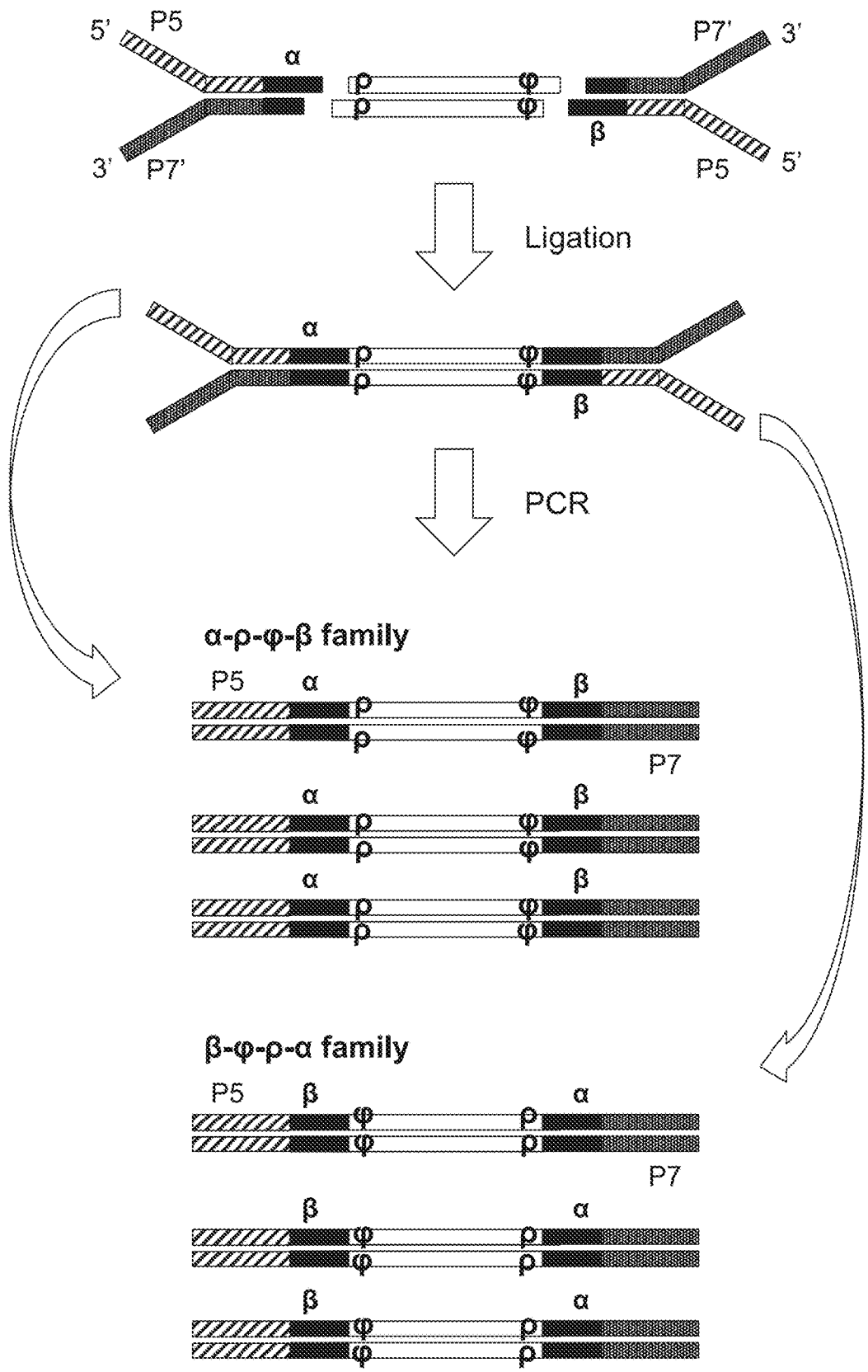
Figure 4A:
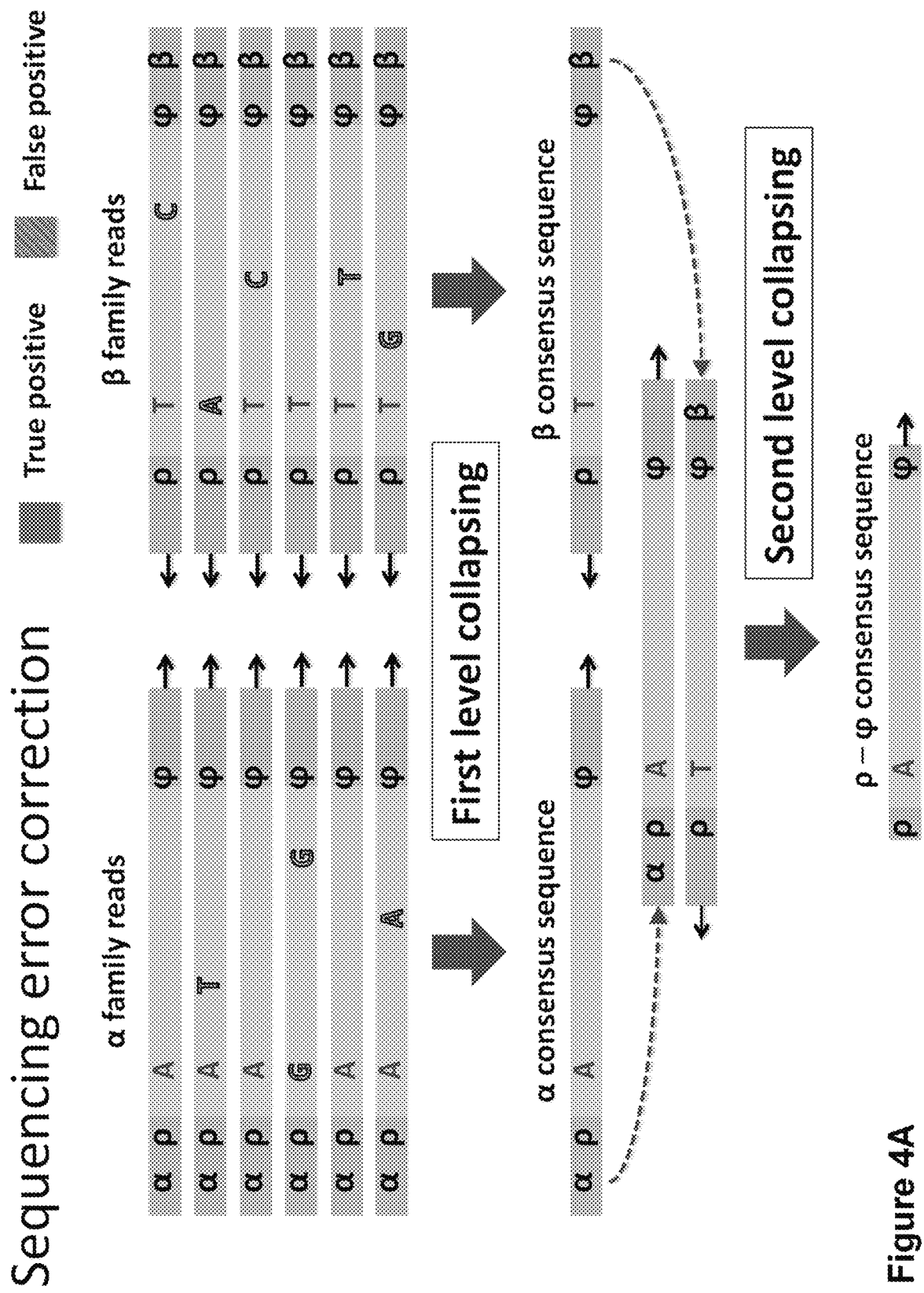
Figure 4B:
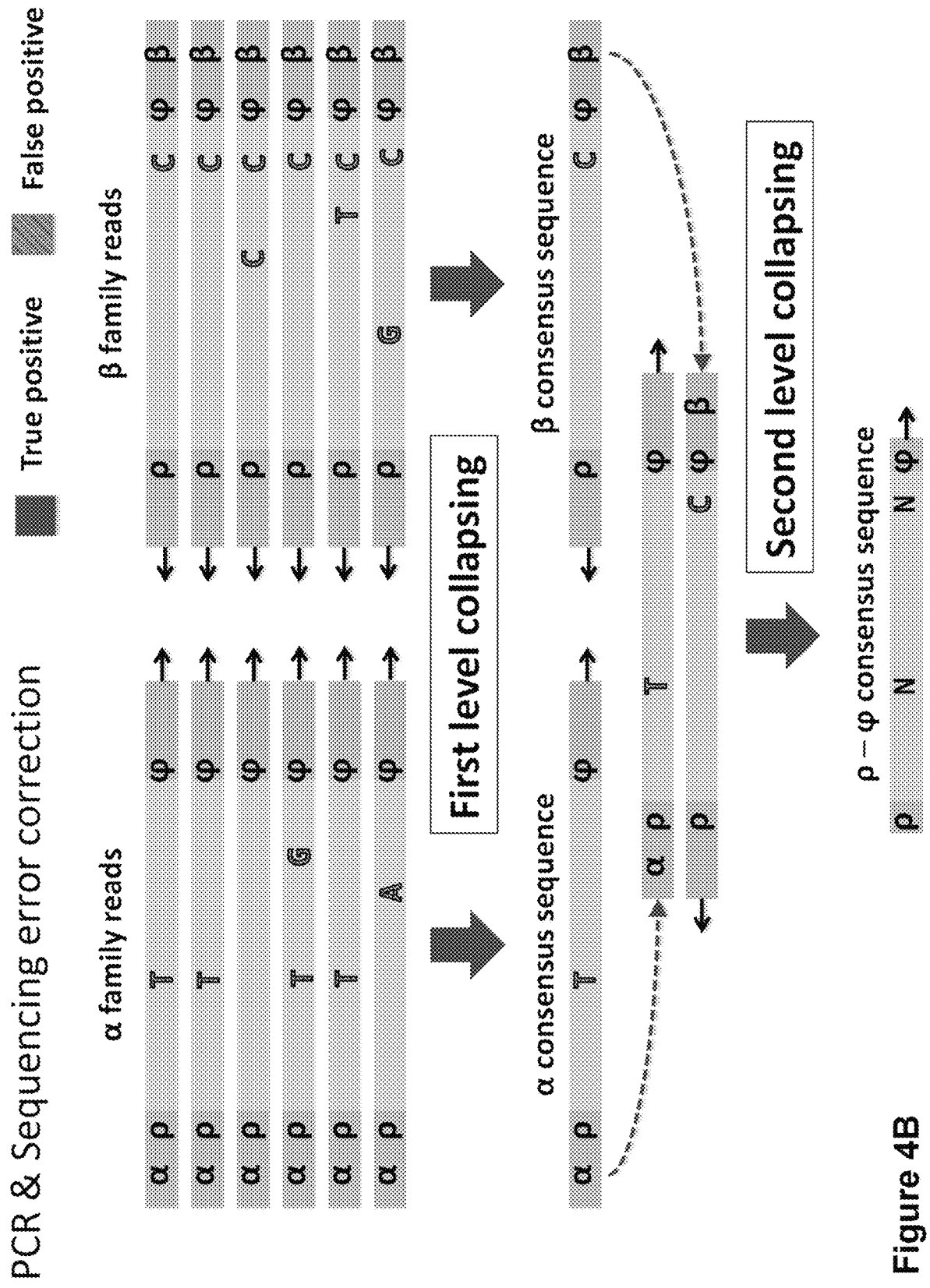
Figure 4C:
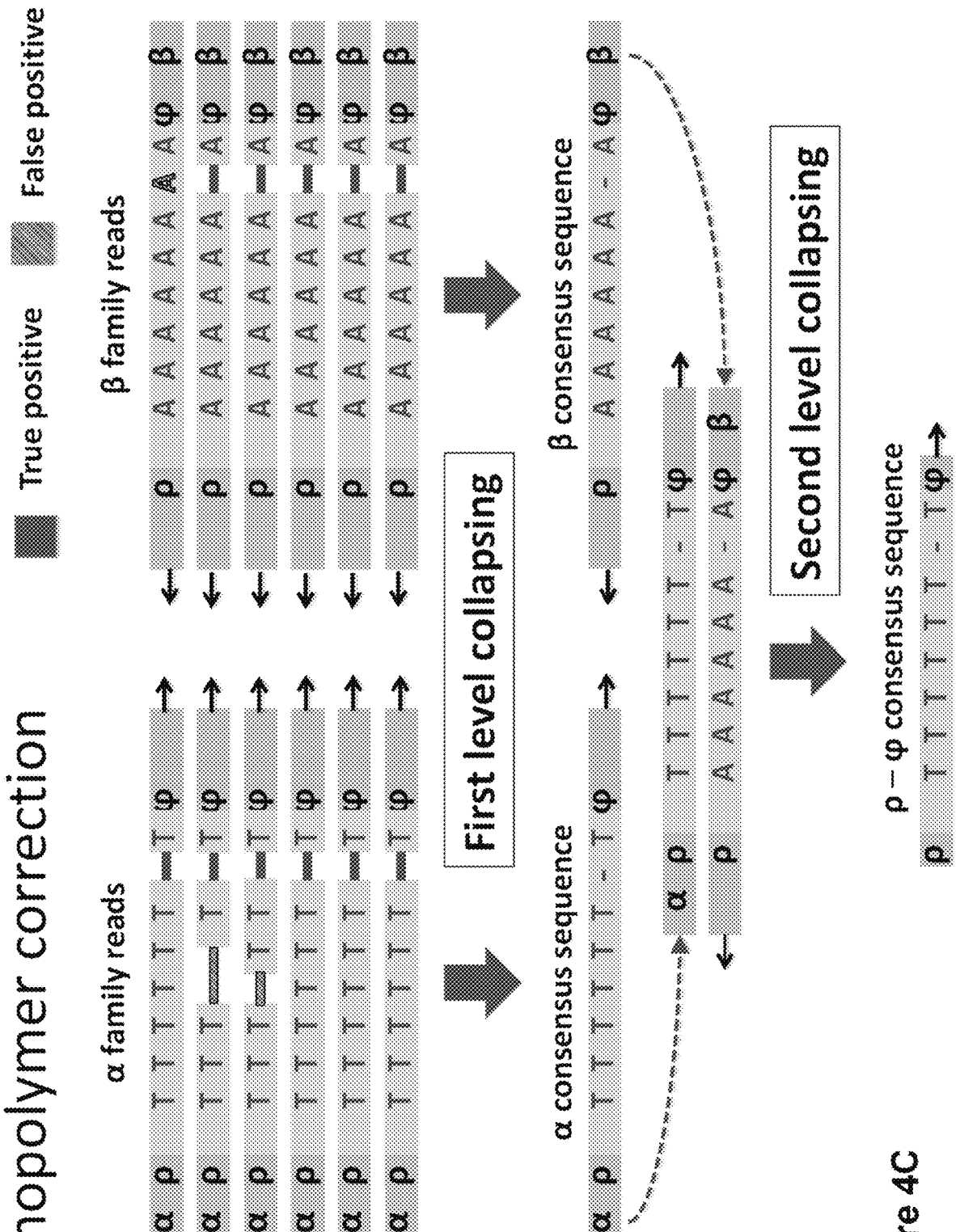
Figure 4D:
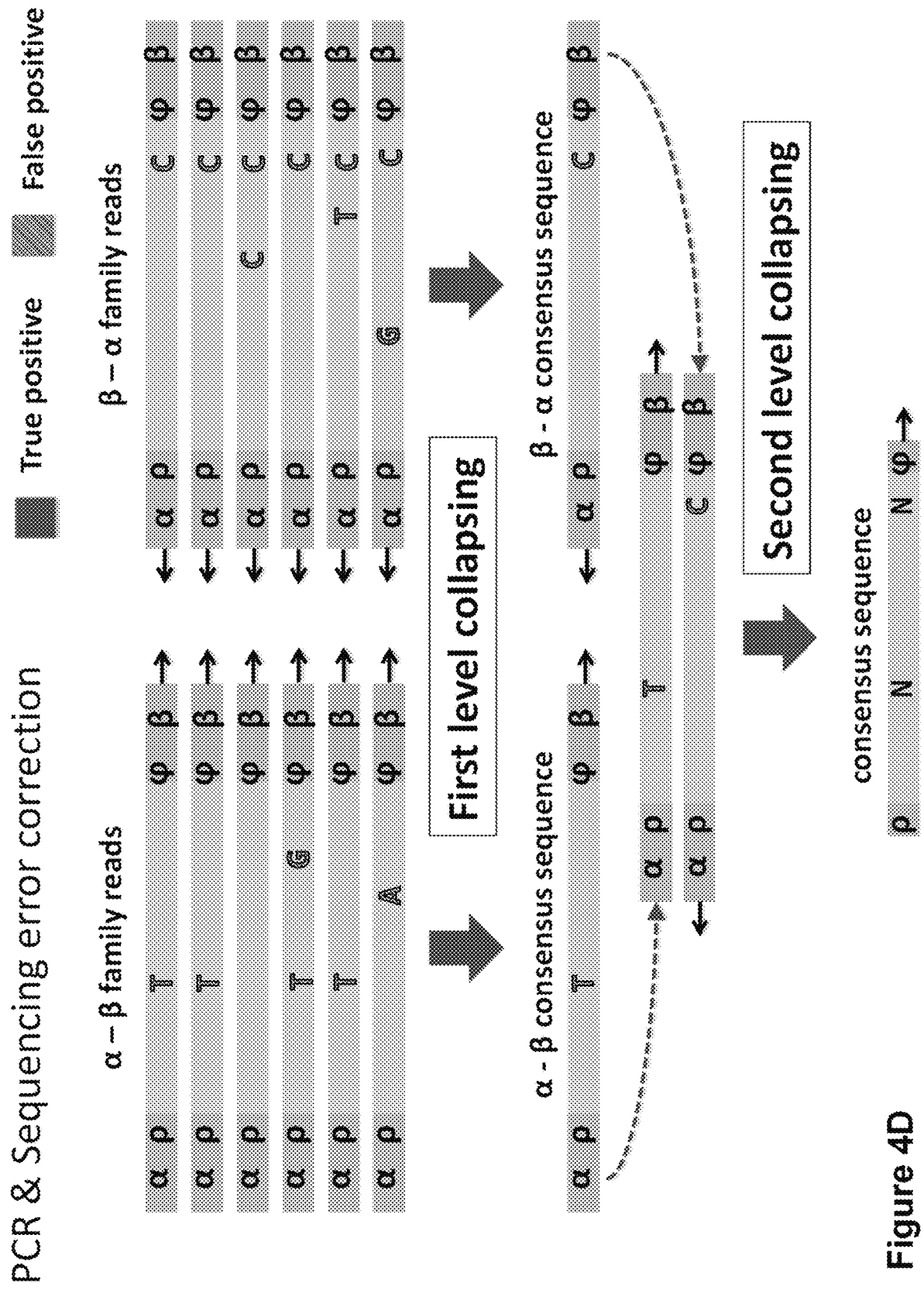
Figure 4E:
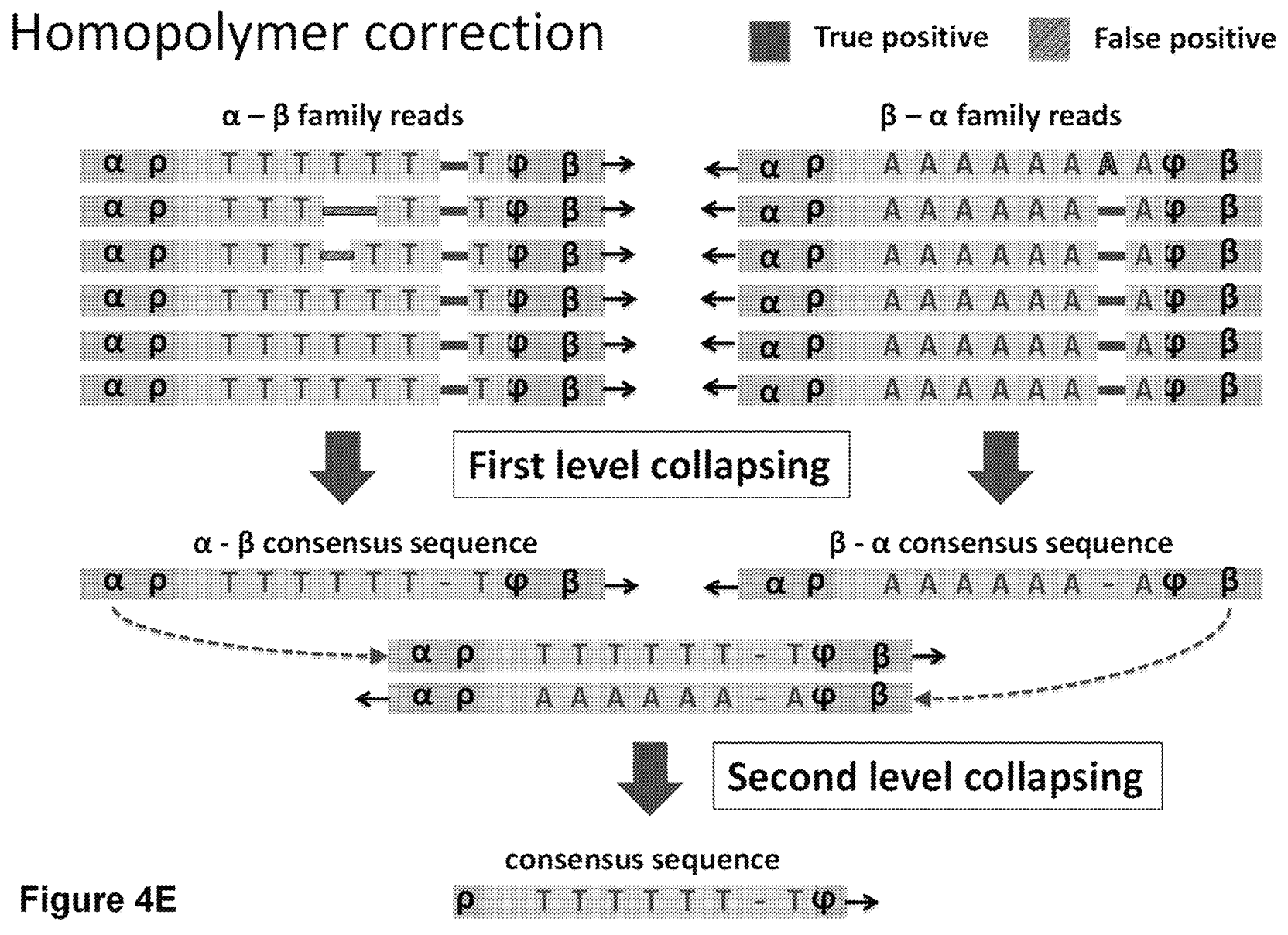

In alternative embodiments, reads having two physical UMIs on both ends, such as those shown in FIG. 3B and FIGS. 4D and 4E, may be collapsed in a second-level collapsing based on a combination of the physical UMIs and the virtual UMIs. This is especially helpful when the physical UMIs are too short to uniquely identify source DNA fragments without using the virtual UMIs. In these embodiments, second level collapsing can be implemented, with physical duplex UMIs as shown in FIG. 3B, by collapsing $\alpha$-$\rho$-$\varphi$-$\beta$ consensus reads and $\beta$-$\varphi$-$\rho$-$\alpha$ consensus reads from the same DNA molecule, thereby obtaining a consensus sequence including nucleotides consistent among all of the reads.

Using UMI and collapsing scheme described herein, various embodiments can suppress different sources of error affecting the determined sequence of a fragment even if the fragment includes alleles with very low allele frequencies. Reads sharing the same UMIs (physical and/or virtual) are grouped together. By collapsing the grouped reads, variants (SNV and small indels) due to PCR, library preparation, clustering, and sequencing errors can be eliminated. FIGS. 4A-4E illustrate how a method as disclosed in an example workflow can suppress different sources of error in determining the sequence of a double stranded DNA fragment. The illustrated reads include $\alpha$-$\rho$-$\varphi$ or $\beta$-$\varphi$-$\rho$ UMIs in FIGS. 3A and 4A-4C, and $\alpha$-$\rho$-$\varphi$-$\beta$ or $\beta$-$\varphi$-$\rho$-$\alpha$ UMIs in FIGS. 3B, 4D and 4E. The $\alpha$ and $\beta$ UMIs are singleplex physical UMIs in FIGS. 3A and 4A-4C. The $\alpha$ and $\beta$ UMIs are duplex UMIs in FIGS. 3B, 4D and 4E. The virtual UMIs $\rho$ and $\varphi$ are located at the ends of a DNA fragment.

The method using singleplex physical UMIs as shown in FIGS. 4A-4C first involves collapsing reads having the same physical UMI $\alpha$ or $\beta$, illustrated as first level collapsing. The first level collapsing obtains an $\alpha$ consensus sequence for reads having the physical UMI $\alpha$, which reads are derived from one strand of the double-stranded fragment. The first level collapsing also obtains a $\beta$ consensus sequence for reads having the physical UMI $\beta$, which reads are derived from another strand of the double-stranded fragment. At a second level collapsing, the method obtains a third consensus sequence from the $\alpha$ consensus sequence and the $\beta$ consensus sequence. The third consensus sequence reflects consensus base pairs from reads having the same duplex virtual UMIs $\rho$ and $\varphi$, which reads are derived from two complementary strands of the source fragment. Finally, the sequence of the double stranded DNA fragment is determined as the third consensus sequence.

The method using duplex physical UMIs as shown in FIGS. 4D-4E first involves collapsing reads having the physical UMIs $\alpha$ and $\beta$ with an $\alpha \rightarrow \beta$ order in the 5'-3' direction, illustrated as first level collapsing. The first level collapsing obtains an $\alpha$-$\beta$ consensus sequence for reads having the physical UMIs $\alpha$ and $\beta$, which reads are derived from a first strand of the double-stranded fragment. The first level collapsing also obtains a $\beta$-$\alpha$ consensus sequence for reads having the physical UMIs β and α with a β→α order in the 5'-3' direction, which reads are derived from a second strand complementary to the first strand of the double-stranded fragment. At a second level collapsing, the method obtains a third consensus sequence from the α-β consensus sequence and the β-α consensus sequence. The third consensus sequence reflects consensus base pairs from reads having the same duplex virtual UMIs ρ and φ, which reads are derived from two strands of the fragment. Finally, the sequence of the double stranded DNA fragment is determined as the third consensus sequence.

FIG. 4A illustrates how a first-level collapsing may suppress sequencing errors. Sequencing errors occur on the sequencing platform after sample and library preparation (e.g., PCR amplification). Sequencing errors may introduce different erroneous bases into different reads. True positive bases are illustrated by solid letters, while false positive bases are illustrated by hatched letters. False positive nucleotides on different reads in the α-ρ-φ family have been excluded from the α consensus sequence. The true positive nucleotide "A" illustrated on the left ends of the α-ρ-φ family reads is retained for the α consensus sequence. Similarly, false positive nucleotides on different reads in the β-φ-ρ family have been excluded from the β consensus sequence, retaining the true positive nucleotide "A". As illustrated here, the first level collapsing can effectively remove sequencing errors. FIG. 4A also shows an optional second-level collapsing relying on the virtual UMIs ρ and φ. This second-level collapsing may further suppress errors as explained above, but such errors are not illustrated in FIG. 4A.

PCR errors occur before clustering amplification. Therefore, one erroneous base pair introduced into a single stranded DNA by the PCR process may be amplified during clustering amplification, thereby appearing in multiple clusters and reads. As illustrated in FIG. 4B and FIG. 4D, a false positive base pair introduced by PCR error may appear in many reads. The "T" base in the α-ρ-φ (FIG. 4B) or α-β (FIG. 4D) family reads and the "C" base in the β-φ-ρ (FIG. 4B) or β-α (FIG. 4D) family reads are such PCR errors. In contrast, the sequencing errors shown in FIG. 4A appear on one or a few reads in the same family. Because PCR sequencing errors appear in many reads of the family, a first-level collapsing of reads in a strand does not remove the PCR errors, even though the first-level collapsing removes sequencing errors (e.g., G and A removed from the α-ρ-φ family in FIG. 4B and the α-β family in FIG. 4D). However, since a PCR error is introduced into a single stranded DNA, the complementary strand of the source fragment and reads derived therefrom usually do not have the same PCR error. Therefore, the second-level collapsing based on reads from the two strands of the source fragment can effectively remove PCR errors as shown at the bottom of FIGS. 4B and 4D.

In some sequencing platforms, homopolymer errors occur to introduce small indel errors into homopolymers of repeating single nucleotides. FIGS. 4C and 4E illustrate homopolymer error correction using the methods described herein. In the α-ρ-φ (FIG. 4C) or α-ρ-φ-β (FIG. 4E) family reads, two "T" nucleotides have been deleted from the second read from the top, and one "T" nucleotide has been deleted from the third read from the top. In the β-φ-ρ (FIG. 4C) or β-φ-ρ-α (FIG. 4E) family reads, one "A" nucleotides has been inserted into the first read from the top. Similar to sequencing error illustrated in FIG. 4A, homopolymer errors occur after PCR amplification, therefore different reads have different homopolymer errors. As a result, the first level collapsing can effectively remove indel errors.

Consensus sequences may be obtained by collapsing reads having one or more common nonrandom UMI and one or more common virtual UMIs. Furthermore, position information may also be used to obtained consensus sequences as described below.

Collapsing by Position

In some implementations, reads are processed to align to a reference sequence to determine alignment locations of the reads on the reference sequence (localization). However, in some implementations not illustrated above, localization is achieved by k-mer similarity analysis and read-read alignment. This second implementation has two advantages: first, it can collapse (error correct) reads that do not match the reference, due to haplotype differences or translocations, and secondly, it does not depend on an aligner algorithm, thereby removing the possibility of aligner-induced artifacts (errors in the aligner). In some implementations, reads sharing the same localization information may be collapsed to obtain consensus sequences to determine the sequence of the source DNA fragments. In some contexts, the alignment process is also referred to as a mapping process. Sequence reads undergo an alignment process to be mapped to a reference sequence. Various alignment tools and algorithms may be used to align reads to the reference sequence as described elsewhere in the disclosure. As usual, in alignment algorithms, some reads are successfully aligned to the reference sequence, while others may not be successfully aligned or may be poorly aligned to the reference sequence. Reads that are successively aligned to the reference sequence are associated with sites on the reference sequence. Aligned reads and their associated sites are also referred to as sequence tags. Some sequence reads that contain a large number of repeats tend to be harder to align to the reference sequence. When a read is aligned to a reference sequence with a number of mismatched bases above a certain criterion, the read is considered poorly aligned. In various embodiments, reads are considered poorly aligned when they are aligned with at least about 1, 2, 3, 4, 5, 6, 7, 8, 9, or 10 mismatches. In other embodiments, reads are considered poorly aligned when they are aligned with at least about 5% of mismatches. In other embodiments, reads are considered poorly aligned when is they are aligned with at least about 10%, 15%, or 20% mismatched bases.

In some implementations, the disclosed methods combine position information with physical UMI information to index source molecules of DNA fragments. Sequence reads sharing a same read position and a same nonrandom or random physical UMI may be collapsed to obtain a consensus sequence for determining the sequence of a fragment or portion thereof. In some implementations, sequence reads sharing the same read position, the same nonrandom physical UMI, and a random physical UMI may be collapsed to obtain a consensus sequence. In such implementations, the adapter may include both a nonrandom physical UMI and a random physical UMI. In some implementations, sequence reads sharing the same read position and the same virtual UMI may be collapsed to obtain a consensus sequence.

Read position information may be obtained by different techniques. For example, in some implementations, genomic coordinates may be used to provide read position information. In some implementations, the position on a reference sequence to which a read is aligned can be used to provide read position information. For example, the start and stop positions of a read on a chromosome may be used to provide read position information. In some implementations, read positions are considered the same if they have identical position information. In some implementations, read positions are considered the same if the difference between the position information is smaller than a defined criterion. For instance, two reads having start genomic positions that differ by less than 2, 3, 4, or 5, base pairs can be considered as reads having the same read position. In other implementations, read positions are considered the same if their position information can be converted to and matched in a particular position space. A reference sequence may be provided prior to sequencing—for example, it may be a well-known and widely-used human genomic sequence—or it may be determined from the reads obtained during sequencing the sample.

Regardless of the specific sequencing platform and protocol, at least a portion of the nucleic acids contained in the sample are sequenced to generate tens of thousands, hundreds of thousands, or millions of sequence reads, e.g., 100 bp reads. In some embodiments, the sequence reads include about 20 bp, about 25 bp, about 30 bp, about 35 bp, about 36 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, about 500 bp, about 800 bp, about 1000 bp, or about 2000 bp.

In some embodiments, reads are aligned to a reference genome, e.g., hg19. In other embodiments, reads are aligned to a portion of a reference genome, e.g., a chromosome or a chromosome segment. The reads that are uniquely mapped to the reference genome are known as sequence tags. In one embodiment, at least about $3 \times 10^6$ qualified sequence tags, at least about $5 \times 10^6$ qualified sequence tags, at least about $8 \times 10^6$ qualified sequence tags, at least about $10 \times 10^6$ qualified sequence tags, at least about $15 \times 10^6$ qualified sequence tags, at least about $20 \times 10^6$ qualified sequence tags, at least about $30 \times 10^6$ qualified sequence tags, at least about $40 \times 10^6$ qualified sequence tags, or at least about $50 \times 10^6$ qualified sequence tags are obtained from reads that map uniquely to a reference genome.

Applications

In various applications, error correction strategies as disclosed herein may provide one or more of the following benefits: (i) detect very low allele frequency somatic mutations, (ii) decrease cycle time by mitigating phasing/prephasing errors, and/or (iii) increase read length by boosting quality of base calls at the later part of reads, etc. The applications and rationales regarding detection of low allele frequency somatic mutations are discussed above.

In certain embodiments, the techniques described herein may permit reliable calling of alleles having frequencies of about 2% or less, or about 1% or less, or about 0.5% or less. Such low frequencies are common in cfDNA originating from tumor cells in a cancer patient. In some embodiments, the techniques described here may permit the identification of rare strains in metagenomic samples, as well as the detection of rare variants in viral or other populations when, for example, a patient has been infected by multiple viral strains, and/or has undergone medical treatment.

In certain embodiments, the techniques described herein may allow shorter sequencing chemistry cycle time. The shortened cycle time increases sequencing errors, which can be corrected using method described above.

In some implementations involving UMIs, long reads may be obtained from paired end sequencing using asymmetric read lengths for a pair of paired-end (PE) reads from two ends of a segment. For instance, a pair of reads having 50 bp in one paired-end read and 500 bp in another paired-end read can be may be "stitched" together with another pair of reads to produce a long read of 1000 bp. These implementations may provide faster sequencing speed for to determine long fragments of low allele frequencies.

Figure 5:
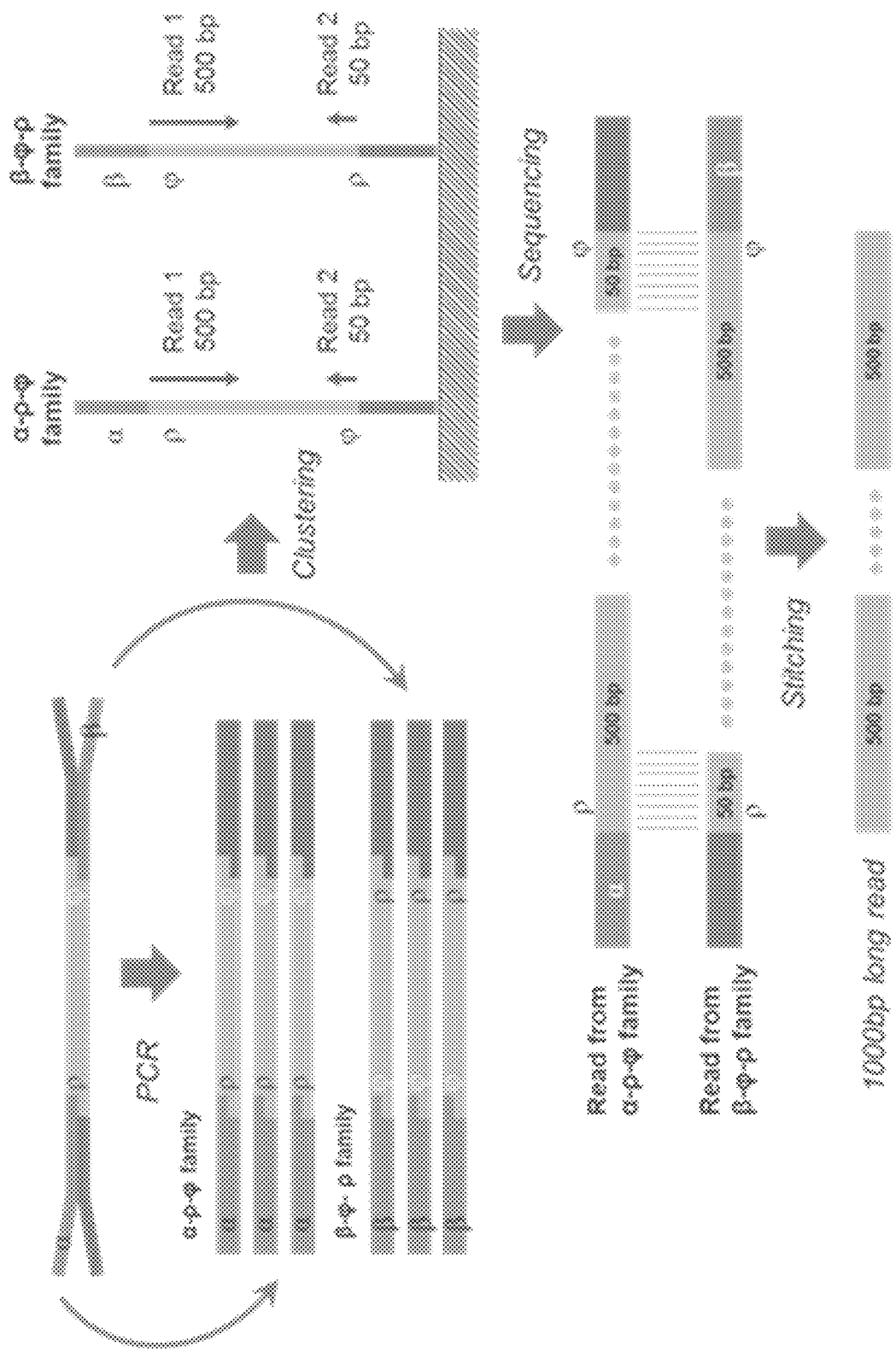
FIG. 5 schematically illustrates applying physical UMIs and virtual UMIs to efficiently obtain long pair end reads.

FIG. 5 schematically illustrates an example to efficiently obtain long paired end reads in this kind of applications by applying physical UMIs and virtual UMIs. Libraries from both strands of same DNA fragments are clustered on the flowcell. The insert size of library is longer than 1 Kb. Sequencing is performed with asymmetric read lengths (e.g., Read1=500 bp, Read2=50 bp), to ensure the quality of long 500 bp reads. Stitching two strands, 1000 bp long PE reads can be created with only 500+50 bp sequencing.

Samples

Samples that are used for determining DNA fragment sequence can include samples taken from any cell, fluid, tissue, or organ including nucleic acids in which sequences of interest are to be determined. In some embodiments involving diagnosis of cancers, circulating tumor DNA may be obtained from a subject's bodily fluid, e.g. blood or plasma. In some embodiments involving diagnosis of fetus, it is advantageous to obtain cell-free nucleic acids, e.g., cell-free DNA (cfDNA), from maternal body fluid. Cell-free nucleic acids, including cell-free DNA, can be obtained by various methods known in the art from biological samples including but not limited to plasma, serum, and urine (see, e.g., Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]; Botezatu et al., Clin Chem. 46: 1078-1084, 2000; and Su et al., J Mol. Diagn. 6: 101-107 [2004]).

In various embodiments the nucleic acids (e.g., DNA or RNA) present in the sample can be enriched specifically or non-specifically prior to use (e.g., prior to preparing a sequencing library). Non-specific enrichment of sample DNA refers to the whole genome amplification of the genomic DNA fragments of the sample that can be used to increase the level of the sample DNA prior to preparing a cfDNA sequencing library. Methods for whole genome amplification are known in the art. Degenerate oligonucleotide-primed PCR (DOP), primer extension PCR technique (PEP) and multiple displacement amplification (MDA) are examples of whole genome amplification methods. In some embodiments, the sample is un-enriched for DNA.

The sample including the nucleic acids to which the methods described herein are applied typically include a biological sample ("test sample") as described above. In some embodiments, the nucleic acids to be sequenced are purified or isolated by any of a number of well-known methods.

Accordingly, in certain embodiments the sample includes or consists essentially of a purified or isolated polynucleotide, or it can include samples such as a tissue sample, a biological fluid sample, a cell sample, and the like. Suitable biological fluid samples include, but are not limited to blood, plasma, serum, sweat, tears, sputum, urine, sputum, ear flow, lymph, saliva, cerebrospinal fluid, ravages, bone marrow suspension, vaginal flow, trans-cervical lavage, brain fluid, ascites, milk, secretions of the respiratory, intestinal and genitourinary tracts, amniotic fluid, milk, and leukophoresis samples. In some embodiments, the sample is a sample that is easily obtainable by non-invasive procedures, e.g., blood, plasma, serum, sweat, tears, sputum, urine, stool, sputum, ear flow, saliva or feces. In certain embodiments the sample is a peripheral blood sample, or the plasma and/or serum fractions of a peripheral blood sample. In other embodiments, the biological sample is a swab or smear, a biopsy specimen, or a cell culture. In another embodiment, the sample is a mixture of two or more biological samples, e.g., a biological sample can include two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments, samples can be obtained from sources, including, but not limited to, samples from different individuals, samples from different developmental stages of the same or different individuals, samples from different diseased individuals (e.g., individuals suspected of having a genetic disorder), normal individuals, samples obtained at different stages of a disease in an individual, samples obtained from an individual subjected to different treatments for a disease, samples from individuals subjected to different environmental factors, samples from individuals with predisposition to a pathology, samples individuals with exposure to an infectious disease agent, and the like.

In one illustrative, but non-limiting embodiment, the sample is a maternal sample that is obtained from a pregnant female, for example a pregnant woman. In this instance, the sample can be analyzed using the methods described herein to provide a prenatal diagnosis of potential chromosomal abnormalities in the fetus. The maternal sample can be a tissue sample, a biological fluid sample, or a cell sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples.

In certain embodiments samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue and/or cells.

Methods of isolating nucleic acids from biological sources are well known and will differ depending upon the nature of the source. One of skill in the art can readily isolate nucleic acids from a source as needed for the method described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing.

Sequencing Library Preparation

In various embodiments, sequencing may be performed on various sequencing platforms that require preparation of a sequencing library. The preparation typically involves fragmenting the DNA (sonication, nebulization or shearing), followed by DNA repair and end polishing (blunt end or A overhang), and platform-specific adapter ligation. In one embodiment, the methods described herein can utilize next generation sequencing technologies (NGS), that allow multiple samples to be sequenced individually as genomic molecules (i.e., singleplex sequencing) or as pooled samples including indexed genomic molecules (e.g., multiplex sequencing) on a single sequencing run. These methods can generate up to several billion reads of DNA sequences. In various embodiments the sequences of genomic nucleic acids, and/or of indexed genomic nucleic acids can be determined using, for example, the Next Generation Sequencing Technologies (NGS) described herein. In various embodiments analysis of the massive amount of sequence data obtained using NGS can be performed using one or more processors as described herein.

In various embodiments the use of such sequencing technologies does not involve the preparation of sequencing libraries.

However, in certain embodiments the sequencing methods contemplated herein involve the preparation of sequencing libraries. In one illustrative approach, sequencing library preparation involves the production of a random collection of adapter-modified DNA fragments (e.g., polynucleotides) that are ready to be sequenced. Sequencing libraries of polynucleotides can be prepared from DNA or RNA, including equivalents, analogs of either DNA or cDNA, for example, DNA or cDNA that is complementary or copy DNA produced from an RNA template, by the action of reverse transcriptase. The polynucleotides may originate in double-stranded form (e.g., dsDNA such as genomic DNA fragments, cDNA, PCR amplification products, and the like) or, in certain embodiments, the polynucleotides may originated in single-stranded form (e.g., ssDNA, RNA, etc.) and have been converted to dsDNA form. By way of illustration, in certain embodiments, single stranded mRNA molecules may be copied into double-stranded cDNAs suitable for use in preparing a sequencing library. The precise sequence of the primary polynucleotide molecules is generally not material to the method of library preparation, and may be known or unknown. In one embodiment, the polynucleotide molecules are DNA molecules. More particularly, in certain embodiments, the polynucleotide molecules represent the entire genetic complement of an organism or substantially the entire genetic complement of an organism, and are genomic DNA molecules (e.g., cellular DNA, cell free DNA (cfDNA), etc.), that typically include both intron sequence and exon sequence (coding sequence), as well as non-coding regulatory sequences such as promoter and enhancer sequences. In certain embodiments, the primary polynucleotide molecules include human genomic DNA molecules, e.g., cfDNA molecules present in peripheral blood of a pregnant subject.

Preparation of sequencing libraries for some NGS sequencing platforms is facilitated by the use of polynucleotides including a specific range of fragment sizes. Preparation of such libraries typically involves the fragmentation of large polynucleotides (e.g. cellular genomic DNA) to obtain polynucleotides in the desired size range.

Paired end reads may be used for the sequencing methods and systems disclosed herein. The fragment or insert length is longer than the read length, and sometimes longer than the sum of the lengths of the two reads.

In some illustrative embodiments, the sample nucleic acid(s) are obtained as genomic DNA, which is subjected to fragmentation into fragments of longer than approximately 50, 100, 200, 300, 400, 500, 600, 700, 800, 900, 1000, 2000, or 5000 base pairs, to which NGS methods can be readily applied. In some embodiments, the paired end reads are obtained from inserts of about 100-5000 bp. In some embodiments, the inserts are about 100-1000 bp long. These are sometimes implemented as regular short-insert paired end reads. In some embodiments, the inserts are about 1000-5000 bp long. These are sometimes implemented as long-insert mate paired reads as described above.

In some implementations, long inserts are designed for evaluating very long sequences. In some implementations, mate pair reads may be applied to obtain reads that are spaced apart by thousands of base pairs. In these implementations, inserts or fragments range from hundreds to thousands of base pairs, with two biotin junction adapters on the two ends of an insert. Then the biotin junction adapters join the two ends of the insert to form a circularized molecule, which is then further fragmented. A sub-fragment including the biotin junction adapters and the two ends of the original insert is selected for sequencing on a platform that is designed to sequence shorter fragments.

Fragmentation can be achieved by any of a number of methods known to those of skill in the art. For example, fragmentation can be achieved by mechanical means including, but not limited to nebulization, sonication and hydroshear. However mechanical fragmentation typically cleaves the DNA backbone at C—O, P—O and C—C bonds resulting in a heterogeneous mix of blunt and 3'- and 5'-overhanging ends with broken C—O, P—O and/C—C bonds (see, e.g., Alnemri and Liwack, J Biol. Chem 265:17323-17333 [1990]; Richards and Boyer, J Mol Biol 11:327-240 [1965]) which may need to be repaired as they may lack the requisite 5'-phosphate for the subsequent enzymatic reactions, e.g., ligation of sequencing adapters, that are required for preparing DNA for sequencing.

In contrast, cfDNA, typically exists as fragments of less than about 300 base pairs and consequently, fragmentation is not typically necessary for generating a sequencing library using cfDNA samples.

Typically, whether polynucleotides are forcibly fragmented (e.g., fragmented in vitro), or naturally exist as fragments, they are converted to blunt-ended DNA having 5'-phosphates and 3'-hydroxyl. Standard protocols, e.g., protocols for sequencing using, for example, the Illumina platform as described in the example workflow above with reference to FIGS. 1A and 1B, instruct users to end-repair sample DNA, to purify the end-repaired products prior to adenylating or dA-tailing the 3' ends, and to purify the dA-tailing products prior to the adapter-ligating steps of the library preparation.

Various embodiments of methods of sequence library preparation described herein obviate the need to perform one or more of the steps typically mandated by standard protocols to obtain a modified DNA product that can be sequenced by NGS. An abbreviated method (ABB method), a 1-step method, and a 2-step method are examples of methods for preparation of a sequencing library, which can be found in patent application Ser. No. 13/555,037 filed on Jul. 20, 2012, which is incorporated by reference by its entirety.

Sequencing Methods

The methods and apparatus described herein may employ next generation sequencing technology (NGS), which allows massively parallel sequencing. In certain embodiments, clonally amplified DNA templates or single DNA molecules are sequenced in a massively parallel fashion within a flow cell (e.g., as described in Volkerding et al. Clin Chem 55:641-658 [2009]; Metzker M Nature Rev 11:31-46 [2010]). The sequencing technologies of NGS include but are not limited to pyrosequencing, sequencing-by-synthesis with reversible dye terminators, sequencing by oligonucleotide probe ligation, and ion semiconductor sequencing. DNA from individual samples can be sequenced individually (i.e., singleplex sequencing) or DNA from multiple samples can be pooled and sequenced as indexed genomic molecules (i.e., multiplex sequencing) on a single sequencing run, to generate up to several hundred million reads of DNA sequences. Examples of sequencing technologies that can be used to obtain the sequence information according to the present method are further described here.

Some sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies include, but are not limited to, the SMRT™ technology of Pacific Biosciences, the ION TORRENT' technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies, e.g., atomic force microscopy (AFM) or transmission electron microscopy (TEM). Illustrative sequencing technologies are described in greater detail below.

In some embodiments, the disclosed methods involve obtaining sequence information for the nucleic acids in the test sample by massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA, e.g., cellular DNA or cfDNA. In some embodiments, genomic DNA from isolated cells is used as the template, and it is fragmented into lengths of several hundred base pairs. In other embodiments, cfDNA or circulating tumor DNA (ctDNA) is used as the template, and fragmentation is not required as cfDNA or ctDNA exists as short fragments. For example fetal cfDNA circulates in the bloodstream as fragments approximately 170 base pairs (bp) in length (Fan et al., Clin Chem 56:1279-1286 [2010]), and no fragmentation of the DNA is required prior to sequencing. Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchor oligos. Under limiting-dilution conditions, adapter-modified, single-stranded template DNA is added to the flow cell and immobilized by hybridization to the anchor oligos. Attached DNA fragments are extended and bridge amplified to create an ultra-high density sequencing flow cell with hundreds of millions of clusters, each containing about 1,000 copies of the same template. In one embodiment, the randomly fragmented genomic DNA is amplified using PCR before it is subjected to cluster amplification. Alternatively, an amplification-free genomic library preparation is used, and the randomly fragmented genomic DNA is enriched using the cluster amplification alone (Kozarewa et al., Nature Methods 6:291-295 [2009]). In some applications, the templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about tens to a few hundred base pairs are aligned against a reference genome and unique mapping of the short sequence reads to the reference genome are identified using specially developed data analysis pipeline software. After completion of the first read, the templates can be regenerated in situ to enable a second read from the opposite end of the fragments. Thus, either single-end or paired end sequencing of the DNA fragments can be used.

Various embodiments of the disclosure may use sequencing by synthesis that allows paired end sequencing. In some embodiments, the sequencing by synthesis platform by Illumina involves clustering fragments. Clustering is a process in which each fragment molecule is isothermally amplified. In some embodiments, as the example described here, the fragment has two different adapters attached to the two ends of the fragment, the adapters allowing the fragment to hybridize with the two different oligos on the surface of a flow cell lane. The fragment further includes or is connected to two index sequences at two ends of the fragment, which index sequences provide labels to identify different samples in multiplex sequencing. In some sequencing platforms, a fragment to be sequenced from both ends is also referred to as an insert.

In some implementation, a flow cell for clustering in the Illumina platform is a glass slide with lanes. Each lane is a glass channel coated with a lawn of two types of oligos (e.g., P5 and P7' oligos). Hybridization is enabled by the first of the two types of oligos on the surface. This oligo is complementary to a first adapter on one end of the fragment. A polymerase creates a compliment strand of the hybridized fragment. The double-stranded molecule is denatured, and the original template strand is washed away. The remaining strand, in parallel with many other remaining strands, is clonally amplified through bridge application.

In bridge amplification and other sequencing methods involving clustering, a strand folds over, and a second adapter region on a second end of the strand hybridizes with the second type of oligos on the flow cell surface. A polymerase generates a complementary strand, forming a double-stranded bridge molecule. This double-stranded molecule is denatured resulting in two single-stranded molecules tethered to the flow cell through two different oligos. The process is then repeated over and over, and occurs simultaneously for millions of clusters resulting in clonal amplification of all the fragments. After bridge amplification, the reverse strands are cleaved and washed off, leaving only the forward strands. The 3' ends are blocked to prevent unwanted priming.

After clustering, sequencing starts with extending a first sequencing primer to generate the first read. With each cycle, fluorescently tagged nucleotides compete for addition to the growing chain. Only one is incorporated based on the sequence of the template. After the addition of each nucleotide, the cluster is excited by a light source, and a characteristic fluorescent signal is emitted. The number of cycles determines the length of the read. The emission wavelength and the signal intensity determine the base call. For a given cluster all identical strands are read simultaneously. Hundreds of millions of clusters are sequenced in a massively parallel manner. At the completion of the first read, the read product is washed away.

In the next step of protocols involving two index primers, an index 1 primer is introduced and hybridized to an index 1 region on the template. Index regions provide identification of fragments, which is useful for de-multiplexing samples in a multiplex sequencing process. The index 1 read is generated similar to the first read. After completion of the index 1 read, the read product is washed away and the 3' end of the strand is de-protected. The template strand then folds over and binds to a second oligo on the flow cell. An index 2 sequence is read in the same manner as index 1. Then an index 2 read product is washed off at the completion of the step.

After reading two indices, read 2 initiates by using polymerases to extend the second flow cell oligos, forming a double-stranded bridge. This double-stranded DNA is denatured, and the 3' end is blocked. The original forward strand is cleaved off and washed away, leaving the reverse strand. Read 2 begins with the introduction of a read 2 sequencing primer. As with read 1, the sequencing steps are repeated until the desired length is achieved. The read 2 product is washed away. This entire process generates millions of reads, representing all the fragments. Sequences from pooled sample libraries are separated based on the unique indices introduced during sample preparation. For each sample, reads of similar stretches of base calls are locally clustered. Forward and reversed reads are paired creating contiguous sequences. These contiguous sequences are aligned to the reference genome for variant identification.

The sequencing by synthesis example described above involves paired end reads, which is used in many of the embodiments of the disclosed methods. Paired end sequencing involves 2 reads from the two ends of a fragment. Paired end reads are used to resolve ambiguous alignments. Paired-end sequencing allows users to choose the length of the insert (or the fragment to be sequenced) and sequence either end of the insert, generating high-quality, alignable sequence data. Because the distance between each paired read is known, alignment algorithms can use this information to map reads over repetitive regions more precisely. This results in better alignment of the reads, especially across difficult-to-sequence, repetitive regions of the genome. Paired-end sequencing can detect rearrangements, including insertions and deletions (indels) and inversions.

Paired end reads may use insert of different length (i.e., different fragment size to be sequenced). As the default meaning in this disclosure, paired end reads are used to refer to reads obtained from various insert lengths. In some instances, to distinguish short-insert paired end reads from long-inserts paired end reads, the latter is specifically referred to as mate pair reads. In some embodiments involving mate pair reads, two biotin junction adapters first are attached to two ends of a relatively long insert (e.g., several kb). The biotin junction adapters then link the two ends of the insert to form a circularized molecule. A sub-fragment encompassing the biotin junction adapters can then be obtained by further fragmenting the circularized molecule. The sub-fragment including the two ends of the original fragment in opposite sequence order can then be sequenced by the same procedure as for short-insert paired end sequencing described above. Further details of mate pair sequencing using an Illumina platform is shown in an online publication at the following address, which is incorporated by reference by its entirety: res.illumina.com/documents/products/technotes/technote_nextera_matepair_data_processing.pdf After sequencing of DNA fragments, sequence reads of predetermined length, e.g., 100 bp, are localized by mapping (alignment) to a known reference genome. The mapped reads and their corresponding locations on the reference sequence are also referred to as tags. In another embodiment of the procedure, localization is realized by k-mer sharing and read-read alignment. The analyses of many embodiments disclosed herein make use of reads that are either poorly aligned or cannot be aligned, as well as aligned reads (tags). In one embodiment, the reference genome sequence is the NCBI36/hg18 sequence, which is available on the World Wide Web at genome.ucsc.edu/cgi-bin/hgGateway?org=Human&db=hg18&hgsid=166260105). Alternatively, the reference genome sequence is the GRCh37/hg19 or GRCh38, which is available on the World Wide Web at genome.ucsc.edu/cgi-bin/hgGateway. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatics alignment analysis for the Illumina Genome Analyzer, which uses the Efficient Large-Scale Alignment of Nucleotide Databases (ELAND) software.

In one illustrative, but non-limiting, embodiment, the methods described herein include obtaining sequence information for the nucleic acids in a test sample, using single molecule sequencing technology of the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries, and the methods allow for direct measurement of the sample, rather than measurement of copies of that sample.

In another illustrative, but non-limiting embodiment, the methods described herein include obtaining sequence information for the nucleic acids in the test sample, using the 454 sequencing (Roche) (e.g. as described in Margulies, M. et al. Nature 437:376-380 [2005]). 454 sequencing typically involves two steps. In the first step, DNA is sheared into fragments of approximately 300-800 base pairs, and the fragments are blunt-ended. Oligonucleotide adapters are then ligated to the ends of the fragments. The adapters serve as primers for amplification and sequencing of the fragments. The fragments can be attached to DNA capture beads, e.g., streptavidin-coated beads using, e.g., adapter B, which contains 5'-biotin tag. The fragments attached to the beads are PCR amplified within droplets of an oil-water emulsion. The result is multiple copies of clonally amplified DNA fragments on each bead. In the second step, the beads are captured in wells (e.g., picoliter-sized wells). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is measured and analyzed.

In another illustrative, but non-limiting, embodiment, the methods described herein includes obtaining sequence information for the nucleic acids in the test sample, using the SOLiD™ technology (Applied Biosystems). In SOLiD™ sequencing-by-ligation, genomic DNA is sheared into fragments, and adapters are attached to the 5' and 3' ends of the fragments to generate a fragment library. Alternatively, internal adapters can be introduced by ligating adapters to the 5' and 3' ends of the fragments, circularizing the fragments, digesting the circularized fragment to generate an internal adapter, and attaching adapters to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In another illustrative, but non-limiting embodiment, the methods described herein include obtaining sequence information for the nucleic acids in the test sample, using the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength detectors (ZMW detectors) that obtain sequence information while phospholinked nucleotides are being incorporated into the growing primer strand. A ZMW detector includes a confinement structure that enables observation of incorporation of a single nucleotide by DNA polymerase against a background of fluorescent nucleotides that rapidly diffuse in an out of the ZMW (e.g., in microseconds). It typically takes several milliseconds to incorporate a nucleotide into a growing strand. During this time, the fluorescent label is excited and produces a fluorescent signal, and the fluorescent tag is cleaved off. Measurement of the corresponding fluorescence of the dye indicates which base was incorporated. The process is repeated to provide a sequence.

In another illustrative, but non-limiting embodiment, the methods described herein include obtaining sequence information for the nucleic acids in the test sample, using nanopore sequencing (e.g. as described in Soni G V and Meller A. Clin Chem 53: 1996-2001 [2007]). Nanopore sequencing DNA analysis techniques are developed by a number of companies, including, for example, Oxford Nanopore Technologies (Oxford, United Kingdom), Sequenom, NABsys, and the like. Nanopore sequencing is a single-molecule sequencing technology whereby a single molecule of DNA is sequenced directly as it passes through a nanopore. A nanopore is a small hole, typically of the order of 1 nanometer in diameter. Immersion of a nanopore in a conducting fluid and application of a potential (voltage) across it results in a slight electrical current due to conduction of ions through the nanopore. The amount of current that flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore provides a read of the DNA sequence.

In another illustrative, but non-limiting, embodiment, the methods described herein includes obtaining sequence information for the nucleic acids in the test sample, using the chemical-sensitive field effect transistor (chemFET) array (e.g., as described in U.S. Patent Application Publication No. 2009/0026082). In one example of this technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned as a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In another embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be detected by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct detection allows recordation of nucleotide incorporation in seconds.

In another embodiment, the present method includes obtaining sequence information for the nucleic acids in the test sample, using sequencing by hybridization. Sequencing-by-hybridization includes contacting the plurality of polynucleotide sequences with a plurality of polynucleotide probes, wherein each of the plurality of polynucleotide probes can be optionally tethered to a substrate. The substrate might be flat surface including an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be determined and used to identify the plurality of polynucleotide sequences within the sample.

In some embodiments of the methods described herein, the sequence reads are about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In some embodiments, paired end reads are used to determine sequences of interest, which include sequence reads that are about 20 bp to 1000 bp, about 50 bp to 500 bp, or 80 bp to 150 bp. In various embodiments, the paired end reads are used to evaluate a sequence of interest. The sequence of interest is longer than the reads. In some embodiments, the sequence of interest is longer than about 100 bp, 500 bp, 1000 bp, or 4000 bp. Mapping of the sequence reads is achieved by comparing the sequence of the reads with the sequence of the reference to determine the chromosomal origin of the sequenced nucleic acid molecule, and specific genetic sequence information is not needed. A small degree of mismatch (0-2 mismatches per read) may be allowed to account for minor polymorphisms that may exist between the reference genome and the genomes in the mixed sample. In some embodiments, reads that are aligned to the reference sequence are used as anchor reads, and reads paired to anchor reads but cannot align or poorly align to the reference are used as anchored reads. In some embodiments, poorly aligned reads may have a relatively large number of percentage of mismatches per read, e.g., at least about 5%, at least about 10%, at least about 15%, or at least about 20% mismatches per read.

A plurality of sequence tags (i.e., reads aligned to a reference sequence) are typically obtained per sample. In some embodiments, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags of, e.g., 100 bp, are obtained from mapping the reads to the reference genome per sample. In some embodiments, all the sequence reads are mapped to all regions of the reference genome, providing genome-wide reads. In other embodiments, reads mapped to a sequence of interest.

Apparatus and Systems for Sequencing Using UMIs

Analysis of the sequencing data and the diagnosis derived therefrom are typically performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

One implementation provides a system for use in determining a sequence with low allele frequency in a test sample including nucleic acids, the system including a sequencer for receiving a nucleic acid sample and providing nucleic acid sequence information from the sample; a processor; and a machine readable storage medium having stored thereon instructions for execution on said processor to determine a sequence of interest in the test sample by: (a) receiving sequences of a plurality of amplified polynucleotides, wherein the plurality of amplified polynucleotides are obtained by amplifying double-stranded DNA fragments in the sample including the sequence of interest and attaching adapters to the double-stranded DNA fragments; (b) identifying a plurality of physical UMIs that each are found in one of the plurality of amplified polynucleotides, wherein each physical UMI derives from an adapter attached to one of the double-stranded DNA fragments; (c) identifying a plurality of virtual UMIs that each are found in one of the plurality of amplified polynucleotides, wherein each virtual UMI derives from an individual molecule of one of the double-stranded DNA fragments; and (d) determining sequences of the double-stranded DNA fragments using the sequences of the plurality of amplified polynucleotides, the plurality of physical UMIs, and the plurality of virtual UMIs, thereby reducing errors in the determined sequences of the double-stranded DNA fragments.

Another implementation provides a system including a sequencer for receiving a nucleic acid sample and providing nucleic acid sequence information from the sample; a processor; and a machine readable storage medium having stored thereon instructions for execution on said processor to determine a sequence of interest in the test sample. The instructions includes: (a) applying adapters to both ends of DNA fragments in the sample, wherein the adapters each include a double-stranded hybridized region, a single-stranded 5' arm, a single-stranded 3' arm, and a nonrandom unique molecular index (UMI) on one strand or each strand of the adapters, thereby obtaining DNA-adapter products; (b) amplifying the DNA-adapter products to obtain a plurality of amplified polynucleotides; (c) sequencing the plurality of amplified polynucleotides, thereby obtaining a plurality of reads associated with a plurality of nonrandom UMIs; (d) from the plurality of reads, identifying reads sharing a common nonrandom UMI; and (e) from the identified reads sharing the common nonrandom UMI, determining the sequence of at least a portion of a DNA fragment, from the sample, having an applied adaptor with the common non-random UMI. In some implementations, the instructions further includes: from the reads sharing the common nonrandom UMI, selecting reads sharing both the common nonrandom UMI and a common read position, and wherein determining the sequence of the DNA fragment in (e) uses only reads sharing both the common nonrandom UMI and the common read position in a reference sequence.

In another implementation, the instructions includes: (a) applying adapters to both ends of double-stranded DNA fragments in the sample, wherein the adapters each include a double-stranded hybridized region, a single-stranded 5' arm, a single-stranded 3' arm, and a nonrandom unique molecular index (UMI) on one strand or each strand of the adapters, thereby obtaining DNA-adapter products, wherein the nonrandom UMI can be combined with other information to uniquely identify an individual molecule of the double-stranded DNA fragments; (b) amplifying both strands of the DNA-adapter products to obtain a plurality of amplified polynucleotides; (c) sequencing the plurality of amplified polynucleotides, thereby obtaining a plurality of reads each associated with a nonrandom UMI; (d) identifying a plurality of nonrandom UMIs associated with the plurality of reads; and (e) using the plurality of reads and the plurality of nonrandom UMIs to determine sequences of the double-stranded DNA fragments in the sample.

In some embodiments of any of the systems provided herein, the sequencer is configured to perform next generation sequencing (NGS). In some embodiments, the sequencer is configured to perform massively parallel sequencing using sequencing-by-synthesis with reversible dye terminators. In other embodiments, the sequencer is configured to perform sequencing-by-ligation. In yet other embodiments, the sequencer is configured to perform single molecule sequencing.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads and tags derived from a nucleic acid sample, reference sequences (including reference sequences providing solely or primarily polymorphisms), calls such as cancer diagnosis calls, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

One embodiment provides a computer program product for generating an output indicating the sequence of a DNA fragment of interest in a test sample. The computer product may contain instructions for performing any one or more of the above-described methods for determining a sequence of interest. As explained, the computer product may include a non-transitory and/or tangible computer readable medium having a computer executable or compilable logic (e.g., instructions) recorded thereon for enabling a processor to determine a sequence of interest. In one example, the computer product includes a computer readable medium having a computer executable or compilable logic (e.g., instructions) recorded thereon for enabling a processor to diagnose a condition or determine a nucleic acid sequence of interest.

It should be understood that it is not practical, or even possible in most cases, for an unaided human being to perform the computational operations of the methods disclosed herein. For example, mapping a single 30 bp read from a sample to any one of the human chromosomes might require years of effort without the assistance of a computational apparatus. Of course, the problem is compounded because reliable calls of low allele frequency mutations generally require mapping thousands (e.g., at least about 10,000) or even millions of reads to one or more chromosomes.

The methods disclosed herein can be performed using a system for determining a sequence of interest in a test sample. The system may include: (a) a sequencer for receiving nucleic acids from the test sample providing nucleic acid sequence information from the sample; (b) a processor; and (c) one or more computer-readable storage media having stored thereon instructions for execution on said processor to determining a sequence of interest in the test sample. In some embodiments, the methods are instructed by a computer-readable medium having stored thereon computer-readable instructions for carrying out a method for determining the sequence of interest. Thus one embodiment provides a computer program product including a non-transitory machine readable medium storing program code that, when executed by one or more processors of a computer system, causes the computer system to implement a method for determining the sequences of nucleic acid fragments in a test sample. The program code may include: (a) code for receiving sequences of a plurality of amplified polynucleotides, wherein the plurality of amplified polynucleotides are obtained by amplifying double-stranded DNA fragments in the sample including the sequence of interest and attaching adapters to the double-stranded DNA fragments; (b) code for identifying a plurality of physical UMIs that each are found in one of the plurality of amplified polynucleotides, wherein each physical UMI derives from an adapter attached to one of the double-stranded DNA fragments; (c) code for identifying a plurality of virtual UMIs that each are found in one of the plurality of amplified polynucleotides, wherein each virtual UMI derives from an individual molecule of one of the double-stranded DNA fragments; and (d) code for determining sequences of the double-stranded DNA fragments using the sequences of the plurality of amplified polynucleotides, the plurality of physical UMIs, and the plurality of virtual UMIs, thereby reducing errors in the determined sequences of the double-stranded DNA fragments.

In some implementations, the physical UMIs include nonrandom UMIs. In other implementations, the physical UMIs include random UMIs.

Another implementation provides a computer program product including a non-transitory machine readable medium storing program code that, when executed by one or more processors of a computer system, causes the computer system to implement a method for determining the sequences of nucleic acid fragments in a test sample. The program code may include: (a) code for applying adapters to both ends of DNA fragments in the sample, wherein the adapters each include a double-stranded hybridized region, a single-stranded 5' arm, a single-stranded 3' arm, and a nonrandom unique molecular index (UMI) on one strand or each strand of the adapters, thereby obtaining DNA-adapter products; (b) code for amplifying the DNA-adapter products to obtain a plurality of amplified polynucleotides; (c) code for sequencing the plurality of amplified polynucleotides, thereby obtaining a plurality of reads associated with a plurality of nonrandom UMIs; (d) code for identifying, from the plurality of reads, read sharing a common nonrandom UMI; and (e) code for determining, from the identified reads sharing the common nonrandom UMI, the sequence of at least a portion of a DNA fragment, from the sample, having an applied adaptor with the common non-random UMI.

In another implementation, the program codes include: (a) code for applying adapters to both ends of double-stranded DNA fragments in the sample, wherein the adapters each include a double-stranded hybridized region, a single-stranded 5' arm, a single-stranded 3' arm, and a nonrandom unique molecular index (UMI) on one strand or each strand of the adapters, thereby obtaining DNA-adapter products, wherein the nonrandom UMI can be combined with other information to uniquely identify an individual molecule of the double-stranded DNA fragments; (b) code for amplifying both strands of the DNA-adapter products to obtain a plurality of amplified polynucleotides; (c) code for sequencing the plurality of amplified polynucleotides, thereby obtaining a plurality of reads each associated with a non-random UMI; (d) identifying a plurality of nonrandom UMIs associated with the plurality of reads; and (e) code for using the plurality of reads and the plurality of nonrandom UMIs to determine sequences of the double-stranded DNA fragments in the sample.

In some embodiments, the instructions may further include automatically recording information pertinent to the method. The patient medical record may be maintained by, for example, a laboratory, physician's office, a hospital, a health maintenance organization, an insurance company, or a personal medical record website. Further, based on the results of the processor-implemented analysis, the method may further involve prescribing, initiating, and/or altering treatment of a human subject from whom the test sample was taken. This may involve performing one or more additional tests or analyses on additional samples taken from the subject.

Disclosed methods can also be performed using a computer processing system which is adapted or configured to perform a method for determining a sequence of interest. One embodiment provides a computer processing system which is adapted or configured to perform a method as described herein. In one embodiment, the apparatus includes a sequencing device adapted or configured for sequencing at least a portion of the nucleic acid molecules in a sample to obtain the type of sequence information described elsewhere herein. The apparatus may also include components for processing the sample. Such components are described elsewhere herein.

Sequence or other data, can be input into a computer or stored on a computer readable medium either directly or indirectly. In one embodiment, a computer system is directly coupled to a sequencing device that reads and/or analyzes sequences of nucleic acids from samples. Sequences or other information from such tools are provided via interface in the computer system. Alternatively, the sequences processed by system are provided from a sequence storage source such as a database or other repository. Once available to the processing apparatus, a memory device or mass storage device buffers or stores, at least temporarily, sequences of the nucleic acids. In addition, the memory device may store tag counts for various chromosomes or genomes, etc. The memory may also store various routines and/or programs for analyzing the presenting the sequence or mapped data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. The computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences (e.g., reads, tags and/or reference chromosome sequences) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data as described below.

Among the types of electronically formatted data that may be stored, transmitted, analyzed, and/or manipulated in systems, apparatus, and methods disclosed herein are the following:
   Reads obtained by sequencing nucleic acids in a test sample
   Tags obtained by aligning reads to a reference genome or other reference sequence or sequences
   The reference genome or sequence
   Thresholds for calling a test sample as either affected, non-affected, or no call
   The actual calls of medical conditions related to the sequence of interest
   Diagnoses (clinical condition associated with the calls)
   Recommendations for further tests derived from the calls and/or diagnoses
   Treatment and/or monitoring plans derived from the calls and/or diagnoses These various types of data may be obtained, stored transmitted, analyzed, and/or manipulated at one or more locations using distinct apparatus. The processing options span a wide spectrum. At one end of the spectrum, all or much of this information is stored and used at the location where the test sample is processed, e.g., a doctor's office or other clinical setting. In other extreme, the sample is obtained at one location, it is processed and optionally sequenced at a different location, reads are aligned and calls are made at one or more different locations, and diagnoses, recommendations, and/or plans are prepared at still another location (which may be a location where the sample was obtained).

In various embodiments, the reads are generated with the sequencing apparatus and then transmitted to a remote site where they are processed to determine a sequence of interest. At this remote location, as an example, the reads are aligned to a reference sequence to produce anchor and anchored reads. Among the processing operations that may be employed at distinct locations are the following:
   Sample collection
   Sample processing preliminary to sequencing
   Sequencing
   Analyzing sequence data and deriving medical calls
   Diagnosis
   Reporting a diagnosis and/or a call to patient or health care provider
   Developing a plan for further treatment, testing, and/or monitoring
   Executing the plan
   Counseling Any one or more of these operations may be automated as described elsewhere herein. Typically, the sequencing and the analyzing of sequence data and deriving medical calls will be performed computationally. The other operations may be performed manually or automatically.

Figure 6:
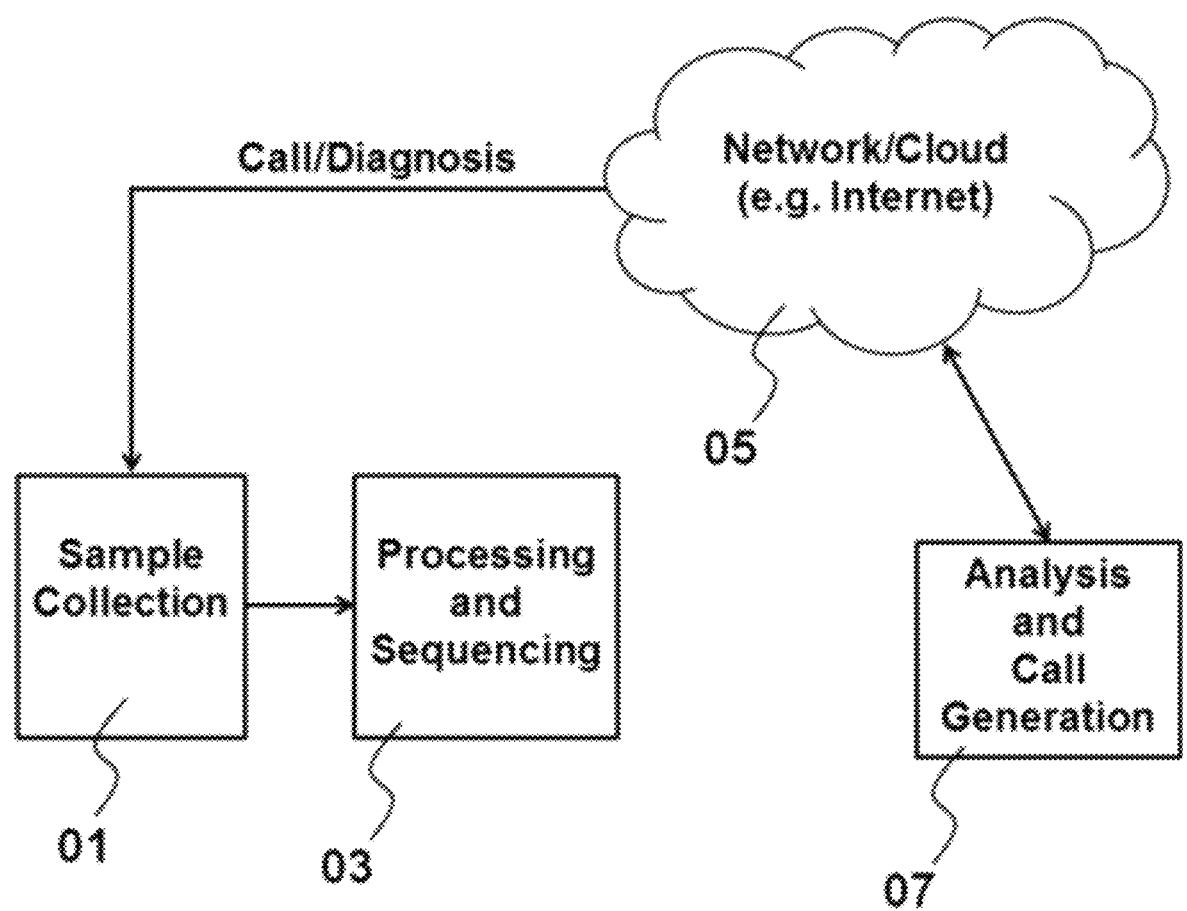
FIG. 6 is a block diagram of a dispersed system for processing a test sample.

FIG. 6 shows one implementation of a dispersed system for producing a call or diagnosis from a test sample. A sample collection location 01 is used for obtaining a test sample from a patient. The samples then provided to a processing and sequencing location 03 where the test sample may be processed and sequenced as described above. Location 03 includes apparatus for processing the sample as well as apparatus for sequencing the processed sample. The result of the sequencing, as described elsewhere herein, is a collection of reads which are typically provided in an electronic format and provided to a network such as the Internet, which is indicated by reference number 05 in FIG. 6.

The sequence data is provided to a remote location 07 where analysis and call generation are performed. This location may include one or more powerful computational devices such as computers or processors. After the computational resources at location 07 have completed their analysis and generated a call from the sequence information received, the call is relayed back to the network 05. In some implementations, not only is a call generated at location 07 but an associated diagnosis is also generated. The call and or diagnosis are then transmitted across the network and back to the sample collection location 01 as illustrated in FIG. 6. As explained, this is simply one of many variations on how the various operations associated with generating a call or diagnosis may be divided among various locations. One common variant involves providing sample collection and processing and sequencing in a single location. Another variation involves providing processing and sequencing at the same location as analysis and call generation.

EXPERIMENTAL

Example 1

Error Suppression Using Random Physical UMI and Virtual UMI

Figure 7A:
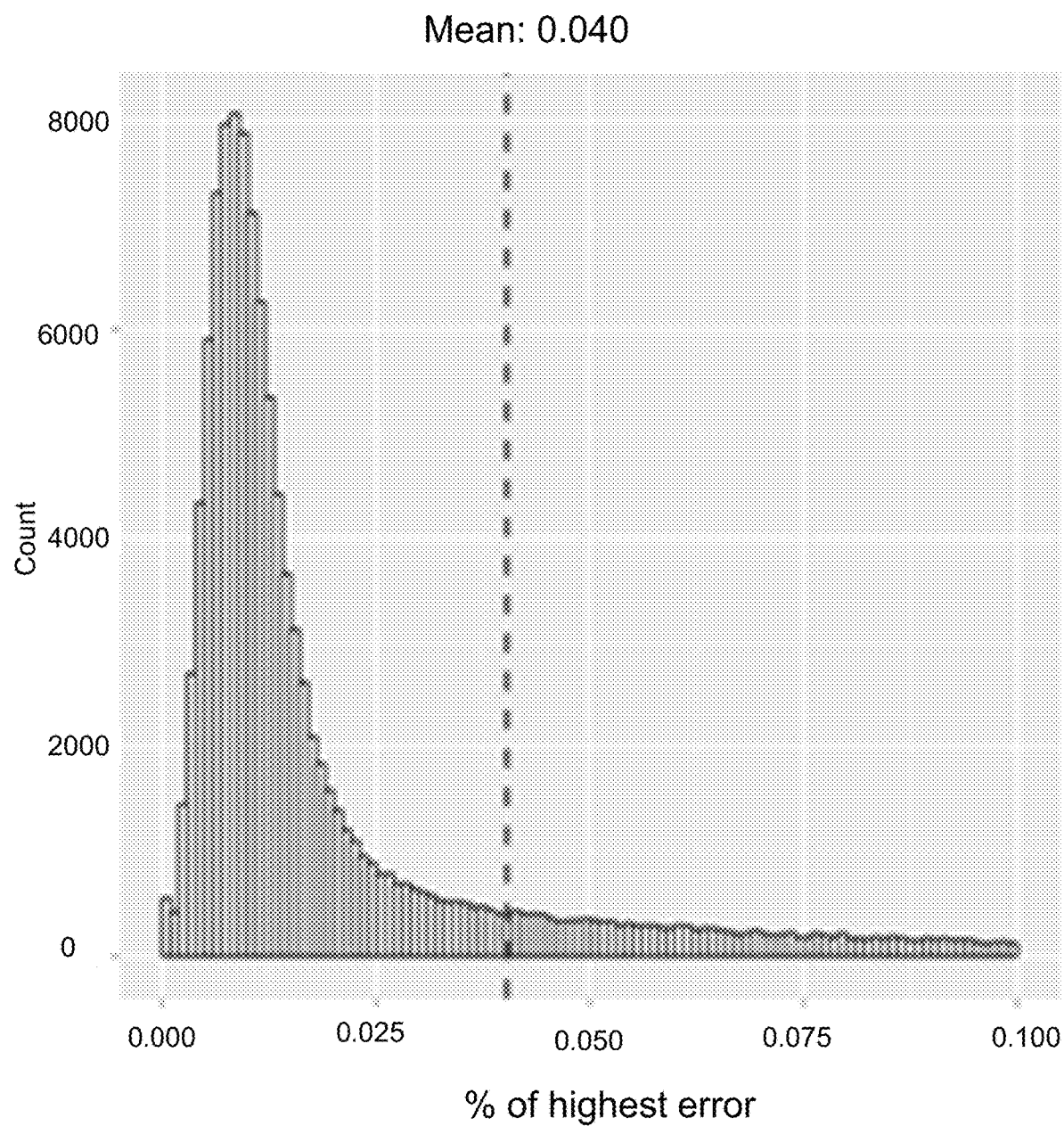
FIG. 7A and FIG. 7B show experimental data demonstrating the effectiveness of error suppression using the methods disclosed herein.
Figure 7B:
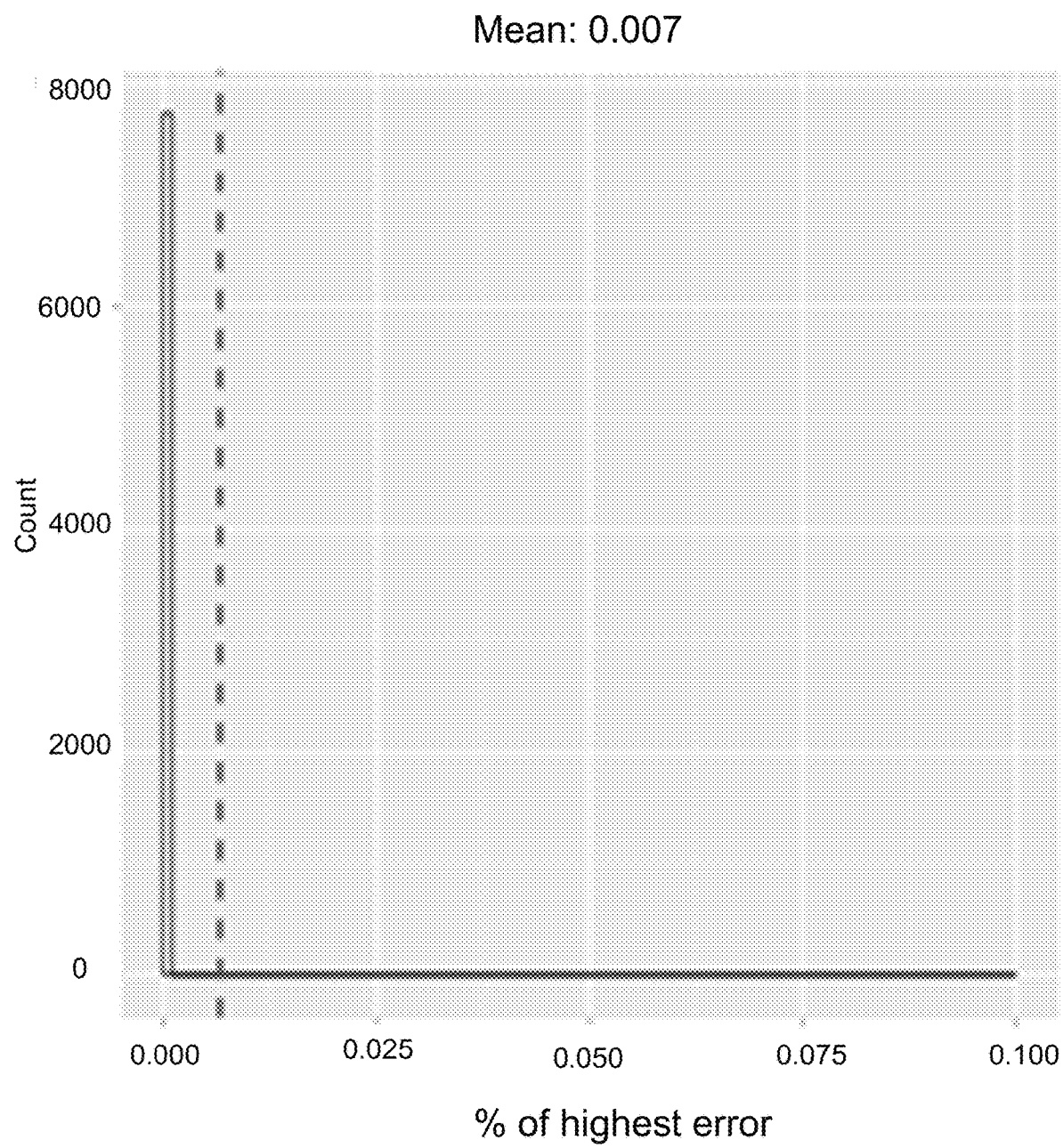

FIG. 7A and FIG. 7B show experimental data demonstrating the effectiveness of error suppression using the methods disclosed herein. Experimenters used sheared gDNA of NA12878. They used TruSeq library preparation and enrichment with custom panel (~130 Kb). Sequencing was performed at 2×150 bp using HiSeq2500 rapid mode, and mean target coverage was ~10,000×. FIG. 7A shows profile of error rate (allele frequency of second highest base) of high quality bases (>Q30) using standard method (the mean error rate is 0.04%). FIG. 7B shows profile of error rate of collapsing/UMI pipeline (the mean error rate is 0.007%). Note that these results are based on prototype code, and further reduction of error rate may be achieved with refined methods.

Example 2

Error Suppression Using Nonrandom Physical UMI and Position

Figure 8:
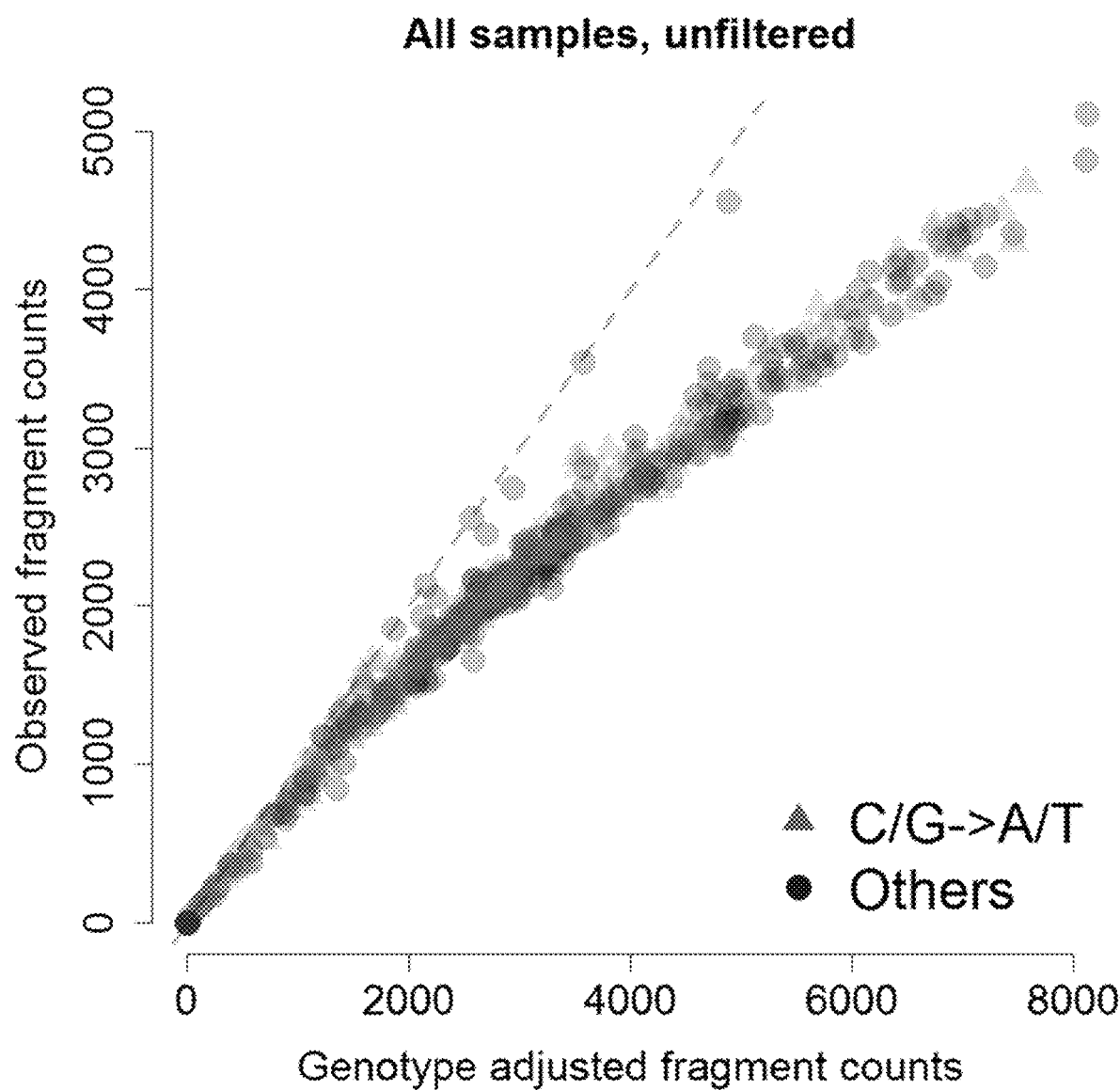
FIG. 8 shows data indicating that using position information alone to collapse reads tends to collapse reads that are actually derived from different source molecules.

FIG. 8 shows data indicating that using position information alone to collapse reads tends to collapse reads that are actually derived from different source molecules. This phenomenon is also referred to as read collision. As a result, the method tends to under estimate the number of fragments in a sample. Shown on the Y axis of FIG. 8 is the observed fragment counts by collapsing reads using position information alone. So on the X axis of FIG. 8 is the estimated fragment counts factoring in different genotypes such as different SNPs and other genotypic differences. As shown in the figure, the observed fragment counts are fewer than the genotype adjusted fragment counts, indicating an underestimation and read collision using position information alone to collapse reads and identify fragments.

Figure 9:
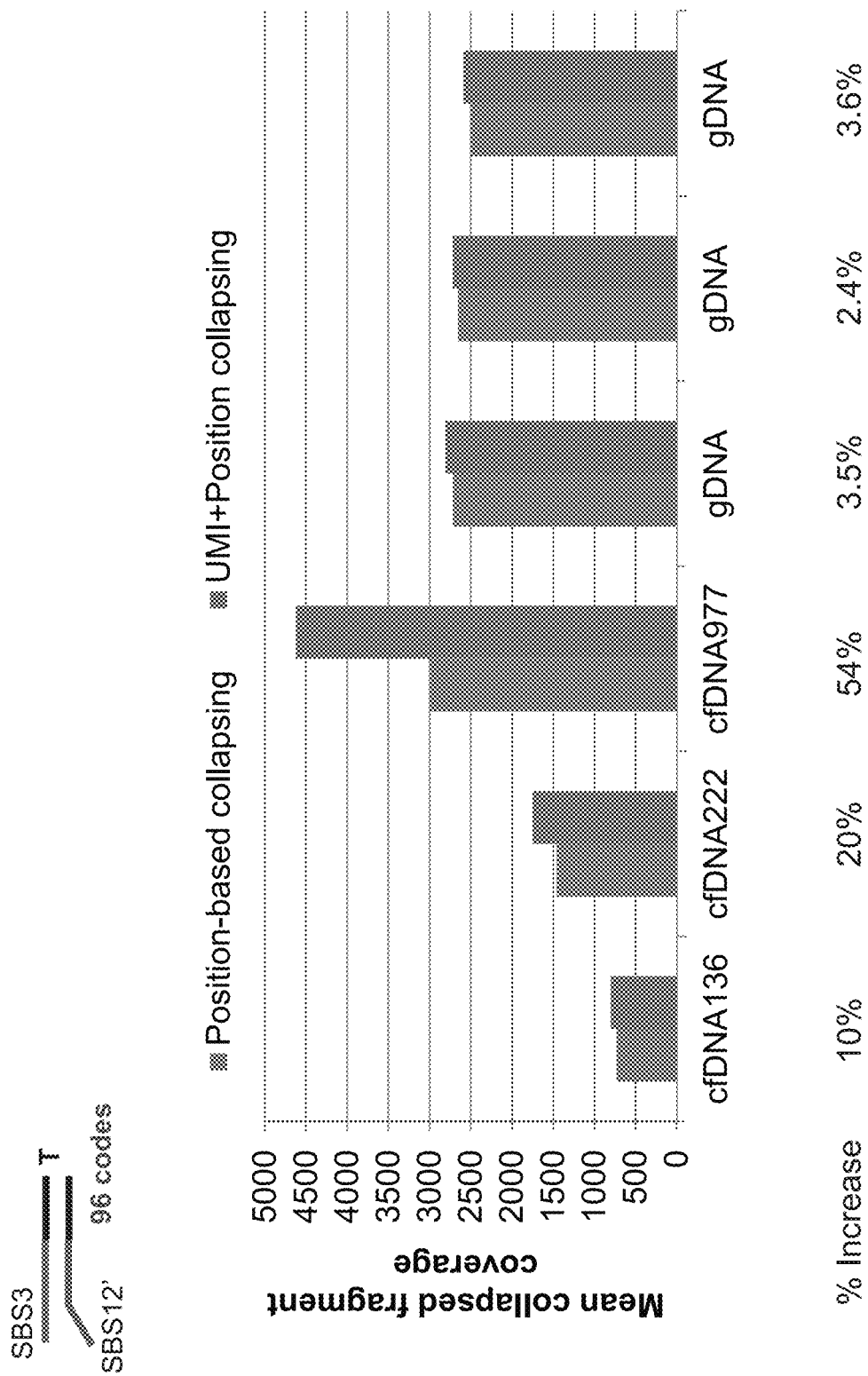
FIG. 9 plots empirical data showing that using nonrandom UMI and position information to collapse reads may provide more accurate estimates of fragments than using position information alone.

FIG. 9 plots empirical data showing that using nonrandom UMI and position information to collapse reads may provide more accurate estimates of fragments than using position information alone. The nonrandom UMI is a 6 bp, duplex UMI located on the double-stranded end of the adapter, the non-random UMI being selected from one of 96 different UMIs. Plotted on the Y axis is the mean collapsed fragment count, with the position-based collapsing method on the left of each pair of bars, and the UMI and position-based collapsing method on the right of each pair of bars. The left three pairs of bars show data for cell free DNA samples of three increasing inputs. The right three pairs of bars show data for three sheared genomic DNA samples. Pairwise comparisons of the two collapsing methods show that UMI and position-based collapsing provides higher estimate of fragment counts than using position alone for collapsing. The comparison of the two collapsing methods shows larger differences for cell free DNA samples than four genomic DNA samples. Furthermore, the difference for cell free DNA samples increases as the sample input increases. The data suggest that collapsing using both nonrandom UMI and position information can correct for read collision and fragment underestimation, especially for cell free DNA.

FIG. 10 shows different errors occur in three samples processed with random UMIs in tabular form. The first three rows of data indicate the percentages of different types of errors 43 samples. The last row shows error rates averaged across the samples. As shown in the table, 97.58% of the UMIs contain no errors, and 1.07% of the UMIs contain one recoverable era. Over 98.65% of all the UMIs are usable for indexing individual DNA fragments. Many of the rest may still be usable when combined with contextual information.

Figure 11A:
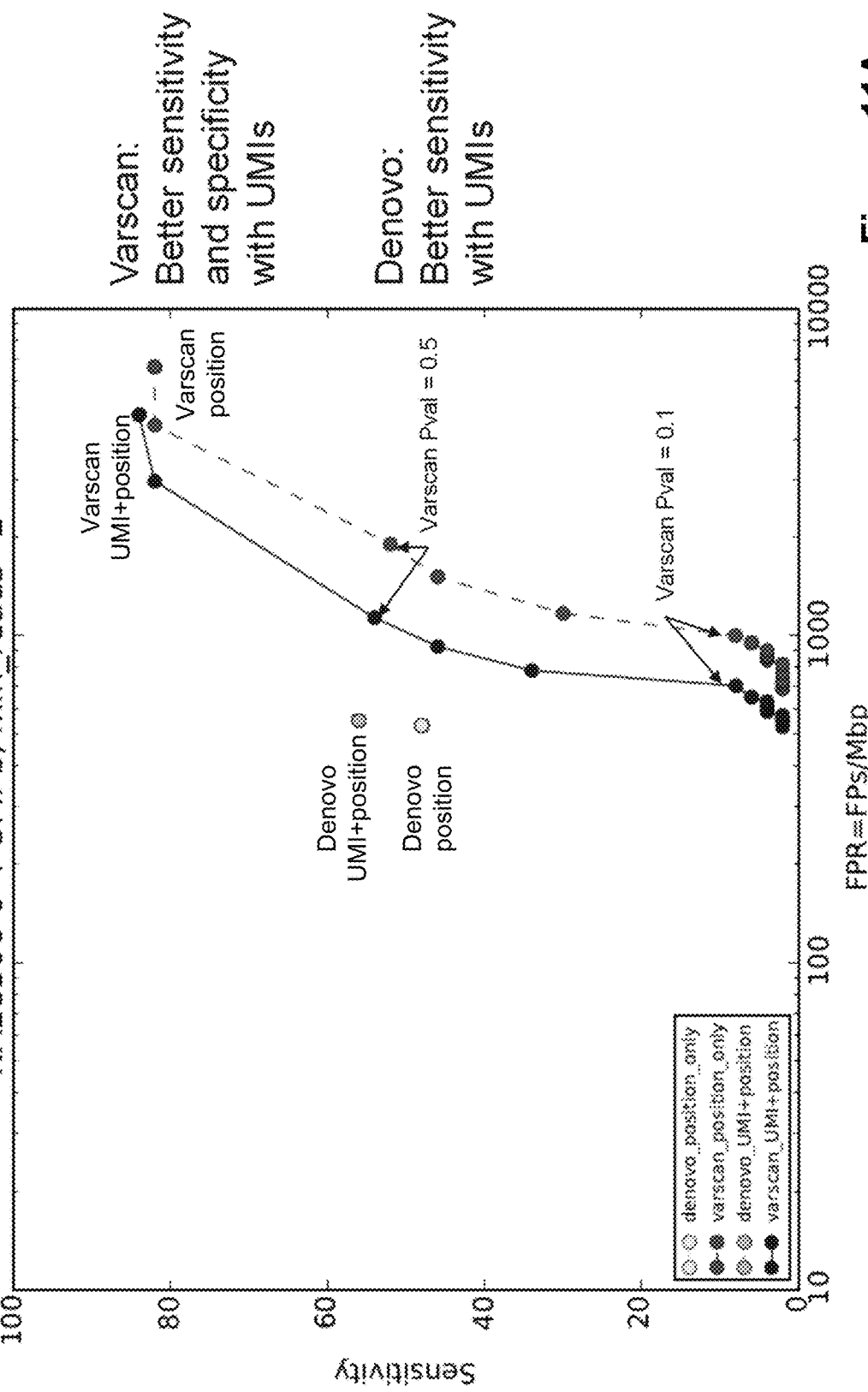
FIG. 11A shows sensitivity and selectivity of calling somatic mutation and CNV in a gDNA sample using the two collapsing methods with two different tools: VarScan and Denovo.

FIG. 11A shows sensitivity and selectivity of calling somatic mutation and CNV in a gDNA sample using the two collapsing methods with two different tools: VarScan and Denovo, Applied with the VarScan tool, collapsing using both UMI and position information provides slightly higher sensitivity and markedly better selectivity (lower false positive rate), as indicated by a shift of the ROC curve to upper left when UMI is used with position. Applied with the Denovo tool, collapsing using both UMI and position information provides markedly higher sensitivity.

Figure 11C:
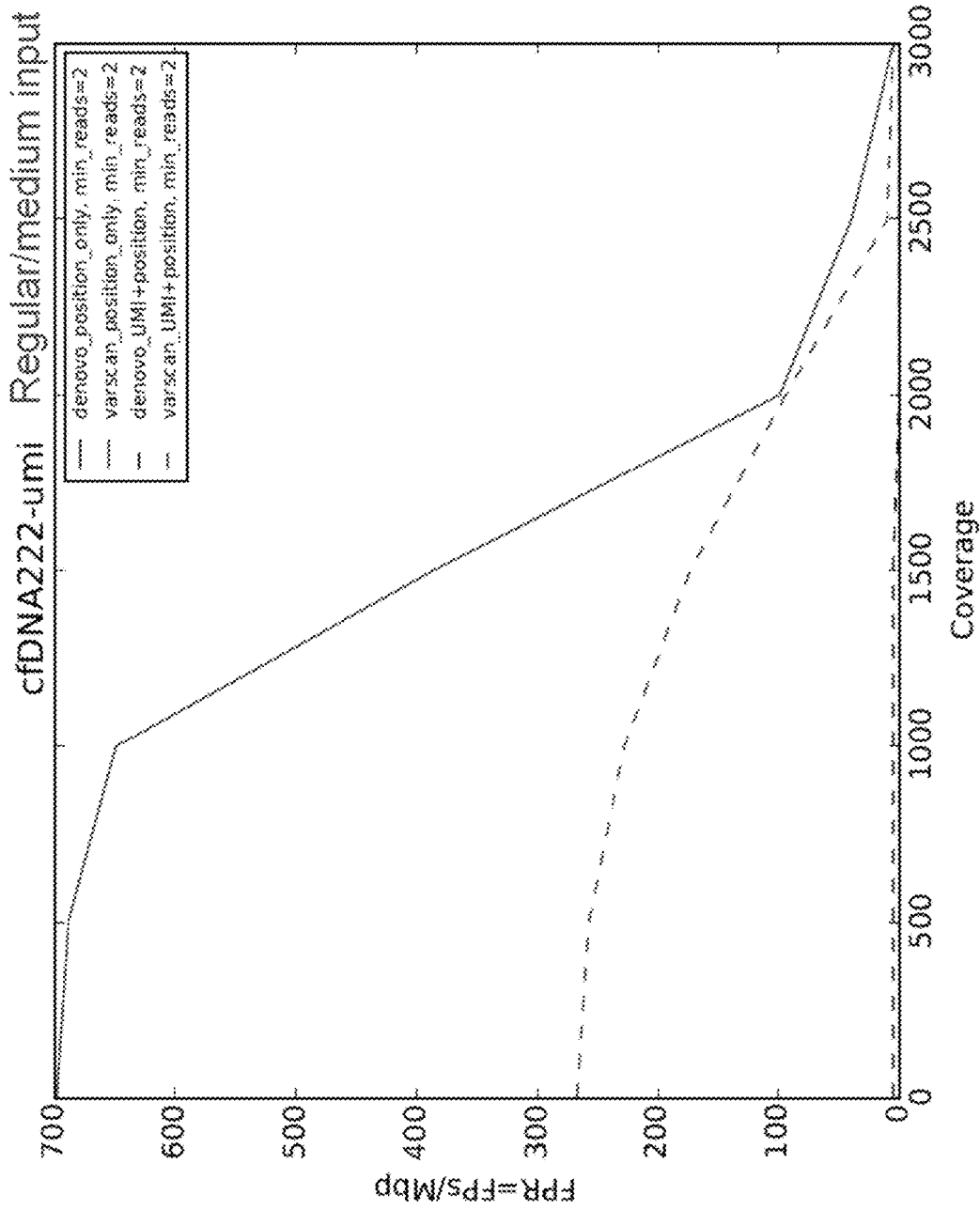

FIGS. 11B-C show selectivity (i.e., false positive rate) of calling somatic mutation and CNV in three cfDNA samples having increasing sample inputs using the two collapsing methods with two different tools: VarScan and Denovo, Applied with the VarScan tool, collapsing using both UMI and position information provides markedly better selectivity (lower false positive rate) for all three samples. Applied with the Denovo tool, collapsing using both UMI and position information provides better selectivity (lower false alarm rate) only in the sample having the largest input.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method for sequencing nucleic acid molecules from a sample using unique molecular indices (UMIs), wherein each unique molecular index (UMI) is an oligonucleotide sequence that can be used to identify an individual molecule of a double-stranded DNA fragment in the sample, comprising (a) applying adapters to both ends of double-stranded DNA fragments in the sample to obtain DNA-adapter products, wherein: each adapter comprises a double-stranded hybridized region, a single-stranded 5' arm, a single-stranded 3' arm, and a physical UMI on one strand or each strand of the adapter, each double-stranded DNA fragment comprises a virtual UMI, and the virtual UMI is a unique sub-sequence in a DNA fragment in the sample, and the plurality of double-stranded DNA fragments is not obtained by restriction endonuclease digestion;

(b) amplifying both strands of the DNA-adapter products to obtain a plurality of amplified polynucleotides;

(c) sequencing the plurality of amplified polynucleotides, thereby obtaining a plurality of reads each comprising a physical UMI sequence corresponding to a physical UMI on an adapter and a virtual UMI sequence corresponding to a virtual UMI on a double-stranded DNA fragment in the sample;

(d) identifying a plurality of physical UMI sequences for the plurality of reads;

(e) identifying a plurality of virtual UMI sequences for the plurality of reads; and (f) determining sequences of the double-stranded DNA fragments in the sample using the plurality of reads obtained in (c), the plurality of physical UMI sequences identified in (d), and the plurality of virtual UMI sequences identified in (e), wherein (f) comprises:

(i) combining, for each double-stranded DNA fragment, a first plurality of reads and a second plurality of reads to determine a consensus nucleotide sequence, each read of the first plurality of reads comprising a first physical UMI sequence of the plurality of physical UMI sequences and a first virtual UMI sequence of the plurality of UMI sequences but not a second physical UMI sequence of the plurality of physical UMI sequences, each read of the second plurality of reads comprising the second physical UMI sequence and the first virtual UMI sequence but not the first physical UMI sequence; and (ii) determining a sequence of the double-stranded DNA fragment using the consensus nucleotide sequence.

2. The method of claim 1, wherein the plurality of physical UMIs includes no more than about 500 unique nonrandom UMIs.

3. The method of claim 1, wherein the plurality of physical UMIs includes fewer than 12 nucleotides.

4. The method of claim 1, wherein the adapters each comprise a read primer sequence on each strand of the double-stranded hybridized region.

5. The method of claim 1, wherein the adapters each comprise a physical UMI on only one strand of the adapters on the single-stranded 5' arm or the single-stranded 3' arm.

6. The method of claim 5, wherein (f) comprises:
(i) collapsing the first plurality of reads into a first group to obtain a first consensus nucleotide sequence;
(ii) collapsing the second plurality of reads into a second group to obtain a second consensus nucleotide sequence; and
(iii) determining, using the first and second consensus nucleotide sequences, a sequence of one of the double-stranded DNA fragments in the sample.

7. The method of claim 6, wherein (iii) comprises: (1) obtaining, using sequence information of the first and second consensus nucleotide sequences, a third consensus nucleotide sequence, and (2) determining, using the third consensus nucleotide sequence, the sequence of one of the double-stranded DNA fragments.

8. The method of claim 1, wherein at least some of the virtual UMIs derive from subsequences at or near the ends of the double-stranded DNA fragments in the sample.

9. The method of claim 1, wherein the plurality of virtual UMIs comprises UMIs of about 6 bp to about 24 bp.

10. The method of claim 1, wherein obtaining the plurality of reads in operation (c) comprises: obtaining two pair-end reads from each of the amplified polynucleotides, wherein the two pair-end reads comprise a long read and a short read, the long read being longer than the short read.

11. The method of claim 10, wherein (f) comprises:
combining read pairs comprising a first physical UMI sequence into a first group and combining read pairs comprising a second physical UMI sequence into a second group, wherein the first and the second physical UMI sequences are uniquely associated with a double-stranded fragment in the sample; and
determining the sequence of the double-stranded fragment in the sample using sequence information of long reads in the first group and sequence information of long reads in the second group.

12. The method of claim 11, wherein the long read has a read length of about 500 bp or more.

13. The method of claim 1, wherein the plurality of amplified polynucleotides includes an allele having an allele frequency lower than about 1%.

14. The method of claim 1, wherein the plurality of amplified polynucleotides includes a cell free DNA molecule originating from a tumor.

* * * * *